US005585233A

United States Patent [19]
Moller et al.

[11] Patent Number: 5,585,233
[45] Date of Patent: Dec. 17, 1996

[54] PTP-S31: A NOVEL PROTEIN TYROSINE PHOSPHATASE

[75] Inventors: Niels P. H. Moller; Karin B. Moller, both of Munich; Axel Ullrich, Martinsried bei Munich, all of Germany

[73] Assignee: Max-Planck Gesellschaft zur Forderung der Wissenschaften E.V., Munich, Germany

[21] Appl. No.: 36,210

[22] Filed: Mar. 23, 1993

[51] Int. Cl.$^6$ .............................. C12Q 1/68; C12P 19/34; C07H 21/04
[52] U.S. Cl. .................. 435/6; 435/91.2; 435/70.3; 435/71.1; 435/240.2; 435/320.1; 435/252.3; 536/23.2; 536/23.5
[58] Field of Search .................. 435/6, 91.2, 320.1, 435/240.2, 252.3, 70.3, 71.1; 536/23.2, 23.5

[56] References Cited

FOREIGN PATENT DOCUMENTS

WO92/01050  1/1992  WIPO.

OTHER PUBLICATIONS

Takekawa et al., Bioch. Biophys. Res. Comm. 189(2), 1223–1230 (1992).
Freeman et al., Identification of a human src homology 2–containing protein–tyrosine–phosphatase:A putative homolog of Drosophila corkscrew, Proc. Natl. Acad. Sci. USA 89:11239–11243 (1992).
Matthews et al., Characterization of hematopoietic intracellular protein tyrosine phoshatases:Description of a phosphatase containing an SH2 domain and another enriched in proline–, glutamic acid–, serine–, and threonine–rich sequences, Mol. Cell. Biol. 12:2396–2405 (1992).
Plutzky et al., Isolation of a src homology 2–containing tyrosine phosphatase, Proc. Natl. Acad. Sci. USA 89:1123–1127 (1992).
Yi et al., Protein tyrosine phosphatase containing SH2 domains:Characterization, preferential expression in hematopoietic cells, and localization to human chromosome 12p12–p13, Mol. Cell. Biol. 12:836–846 (1992).
Gu et al., Identification, cloning, and expression of a cytosolic megakaryocyte protein–tyrosine–phosphatase with sequence homology to cytoskeletal protein 4.1, Proc. Natl. Acad. Sci. USA 88:5867–5871 (1991).
Lombroso et al., Molecular characterization of a protein–tyrosine–phosphatase enriched in striatum, Proc. Natl. Acad. Sci. USA 88:7242–7246 (1991).
Shen et al., A protein–tyrosine phosphatase with sequence similarity to the SH2 domain of the protein–tyrosine kinases, Nature 352:736–739 (1991).
Yang and Tonks, Isolation of a cDNA clone encoding a human protein–tyrosine phosphatase with homology to the cytoskeletal–associated proteins band 4.1, ezrin, and talin, Proc. Natl. Acad. Sci. USA 88:5949–5953 (1991).
Chernoff et al., Cloning of a cDNA for a major human protein–tyrosine–phosphatase, Proc. Natl. Acad. Sci. USA 87:2735–2739 (1990).

Guan et al., Cloning and expression of a protein–tyrosine–phosphatase, Proc. Natl. Acad. Sci. USA 87:1501–1505 (1990).
Tonks et al., CD45, an integral membrane protein tyrosine phosphatase, J. Biol. Chem. 265:10674–10680 (1990).
Charbonneau et al., Human placenta protein–tyrosine–phosphatase: Amino acid sequence and relationship to a family of receptor–like proteins, Proc. Natl. Acad. Sci. USA 86:5252–5256 (1989).
Cool et al., cDNA isolated from a human T–cell library encodes a member of the protein–tyrosine–phosphatase family, Proc. Natl. Acad. Sci. USA 86:5257–5261 (1989).
Pallen et al., Purification of a phosphotyrosine phosphatase that dephosphorylates the epidermal growth factor receptor autophosphorylation sites, Ann. N.Y. Acad. Sci. 551:299–308 (1988).
Tonks et al., Purification of the major protein–tyrosine–phosphatases of human placenta, J. Biol. Chem. 263:6722–6730 (1988).
Tsai et al., Isolation and characterization of temperature–sensitive and thermostable mutants of the human receptor–like protein tyrosine phosphatase LAR, J. Biol. Chem. 266(16):10534–10543 (1991).
Gebbink et al., Cloning, expression and chromosomal localization of a new putative receptor–like protein tyrosine phosphatase, FEBS Lett., 290:123–130 (1991).
Jirik et al., Cloning and chromosomal assignment of a widely expressed human receptor–like protein–tyrosine phosphatase, FEBS Lett 273:239–242 (1990).
Jirik et al., Cloning of a novel receptor–linked protein tyrosine phosphatase from a human hepatoblastoma cell line, FASEB J. 4A: 2082 (Abstr. 2253) (1990).
Kaplan et al., Cloning of three human tyrosine phosphatases reveals a multigene family of receptor–linked protein–tyrosine–phosphatases expressed in brain, Proc. Natl. Acad. Sci. USA 87:7000–7004 (1990).
Streuli et al., Distinct functional roles of two intracellular phosphatase like domains of the receptor–linked protein tyrosine phosphatases LCA and LAR, EMBO Journal 9:2399–2407 (1990).
Krueger et al., Structural diversity and evolution of human receptor–like protein tyrosine phosphatases, EMBO J. 9:3241–3252 (1990).

(List continued on next page.)

*Primary Examiner*—Kenneth R. Horlick
*Attorney, Agent, or Firm*—Pennie & Edmonds

[57] ABSTRACT

A novel protein tyrosine phosphatase designated PTP-S31 and its subfamily are identified, as are nucleic acid molecule coding therefor. Included in this family are PTP-S31 proteins or glycoproteins having one, two, or three identified amino acid changes in previously defined consensus sequences in the catalytic phosphatase domains of known protein tyrosine phosphatases. The PTP-S31 proteins or glycoproteins may be produced by recombinant means. Antibodies to PTP-S31 proteins or glycoproteins and nucleic acid constructs coding therefor, and methods for screening molecules which can bind to PTP-S31 proteins or glycoproteins and inhibit or stimulate their enzymatic activity, are provided.

15 Claims, 29 Drawing Sheets

OTHER PUBLICATIONS

Ohagi et al., Sequence of a cDNA encoding human LRP (leukocyte common antigen–related peptide), Nucl. Acids Res. 18:7159 (1990).

Matthews et al., Identification of an additional member of the protein–tyrosine–phosphatase family:Evidence for alternative splicing in the tyrosine phosphatase domain, Proc. Natl. Acad. Sci. USA 87:4444–4448 (1990).

Mustelin et al., Rapid activation of the T–cell tyrosine protein kinase pp56lck by the CD45 phosphotyrosine phosphatase, Proc. Natl. Acad. Sci. USA 86:6302–6306 (1989).

Ostergaard et al., Expression of CD45 alters phosphorylation of the lck–encoded tyrosine protein kinase in murine lymphoma T–cell lines, Proc. Natl. Acad. Sci. USA 86:8959–8963 (1989).

Streuli et al., A new member of the immunoglobulin superfamily that has a cytoplasmic region homologous to the leukocyte common antigen, J. Exp. Med., 168:1523–1530 (1988).

Ralph et al., Structural variants of human T200 glycoprotein (leukocyte common antigen), EMBO J. 6:1251–1257 (1987).

Hariharan et al., Cloning and characterization of a receptor–class phosphotyrosine phosphatase gene expressed on central nervous system axons in Drosophila melanogaster, Proc. Natl. Acad. Sci. USA 88:11266–11270 (1991).

Streuli et al., A family of receptor–linked protein tyrosine phosphatases in humans and Drosophila, Proc. Natl. Acad. Sci. USA 86:8698–8702 (1989).

Itoh et al., Purification and characterization of the catalytic domains of the human receptor–linked protein tyrosine phosphatases HPTP beta, leukocyte common antigen (LCA), and leukocyte common antigen–related molecule (LAR), J. Biol. Chem. 267:12356–12363 (1992).

Stover et al., Protein–tyrosine–phosphatase CD45 is phosphorylated transiently on tyrosine upon activation of Jurkat T cells, Proc. Natl. Acad. Sci., USA 88:7704–7707 (1991).

Margolis et al., EGF induces tyrosine phosphorylation of phospholipase C–II:A potential mechanism for EGF receptor signaling, Cell 57:1101–1107 (1989).

Morla et al., Reversible tyrosine phosphorylation of cdc2:Dephosphorylation accompanies activation during entry into mitosis, Cell 58:193–203 (1989).

Fantus et al., Pervanadate [Peroxide(s) of vanadate] mimics insulin action in rat adipocytes via activation of the insulin receptor tyrosine kinase, Biochem. 28:8864–8871 (1989).

Miyajima et al., Cytokine receptors and signal transduction, Ann. Rev. Immunol. 10:295-331 (1992).

Patthy, Homology of a domain of the growth hormone/prolactin receptor family with type III modules of fibronectin, Cell 61:13–14 (1990).

Ullrich et al., Insulin–like growth factor I receptor primary structure:comparison with insulin receptor suggests structural determinants that define functional specificity, EMBO J. 5:2503–2512 (1986).

Shier and Watt, Primary structure of a putative receptor for a ligand of the insulin family, J. Biol. Chem. 264:14605–14608 (1989).

Charbonneau and Tonks, 1002 Protein phosphatases?, Ann. Rev. Cell. Biol. 8:463–493 (1992).

Pot and Dixon, A thousand and two protein tyrosine phosphatases, Biochem. Biophys. Acta. 1136:35–43 (1992).

Fischer et al., Protein tyrosine phosphatases: A diverse family of intracellular and transmembrane enzymes, Science 253:401–406 (1991).

Hunter, Protein–tyrosine phosphatases: The other side of the coin, Cell 58, 1013–1016 (1989).

Hunter, A tail of two src's: Mutatis mutandis, Cell 49:1–4 (1987).

```
  1  gaaaccagagcaaaaacattagtaatgctaacacagtgttttgaaaaaggacggatcaga   60
  1   E  T  R  A  K  T  L  V  M  L  T  Q  C  F  E  K  G  R  I  R   20

61  tgccatcagtattggccagaggacaacaagccagttactgtctttggagatagtgatt   120
 21   C  H  Q  Y  W  P  E  D  N  K  P  V  T  V  F  G  D  I  V  I   40

121  acaaagctaatggaggatgttcaaatagattgactatcagggatctgaaaattgaaagg   180
 41   T  K  L  M  E  D  V  Q  I  D  W  T  I  R  D  L  K  I  E  R   60

181  catggggattgcatgactgttcgacagtgtaacttactgcctggccagagcatgggggtt   240
 61   H  G  D  C  M  T  V  R  Q  C  N  F  T  A  W  P  E  H  G  V   80

241  cctgagaacagcgcccctctaattcactttgtgaagttggttcgagcaagcaggcacat   300
 81   P  E  N  S  A  P  L  I  H  F  V  K  L  V  R  A  S  R  A  H   100

301  gacaccacctatgattgtt                                           321
101   D  T  T  P  M  I  V                                         107
```

FIG. 1

```
  1 ETRAKTLVMLTQCFEKGRIRCHQYWPEDNKPVTVFGD..IVITKLMEDVQ  48
    ::.:: .:  .: ||||||||  :: .: ::.  |||
101 EQKSRGVVMLNRVMEKGSLKCAQYWPQKEEKEMIFEDTNLKLTLISEDIK 150

49 IDWTIRDLKIERHG..DCMTVRQCNFTAWPEHGVPENSAPLIHFVKLVR. 95
    :.|:.|:.|:.|    :.:|  ||| |||||||  .:.:|:. |||
151 SYYTVRQLELENLTTQETREILHFHYTTWPDFGVPESPASFLNFLFKVRE 200

96 .ASRAHDTTPMIV.................................... 107
     :: . .: .:|:|
201 SGSLSPEHGPVVHCSAGIGRSGTFCLADTCLLLMDKRKDPSSVDIKKVL  250
```

```
  1       tatttagcttgggaagtaatacggggatatttaactcctggggtttgaaaccatgt              60
 61       cattgagaatgaggccaataagcaagaatcctcctgcaacatgttgaagagctttg            120
 21        M   R   M   R   P   I   S   K   K   S   F   L   Q   H   V   E   E   L   C           40
121       cacaaacaacaacctaaagtttcaagaaTTTCGGAATTACCAAAATTTCTTCAGGA            180
 41        T   N   N   L   K   F   Q   E   E   F   S   E   L   P   K   F   L   Q   D           60
181       TCTTTCTTCAACTGATGCTGATCTGCCTTGGAATAGAGCAAAAAACCGCTTCCCAAACAT        240
 61        L   S   S   T   D   A   D   L   P   W   N   R   A   K   N   R   F   P   N   I        80
241       AAAACCATATAATAATAACAGAGTAAAGctgatagctgacgctagtgttccaggttcgga        300
 81        K   P   Y   N   N   N   R   V   K   L   I   A   D   A   S   V   P   G   S   D       100
301       ttatattaatgccagctatatttctgttatttgtccaatgaatttattgctactca           360
101        Y   I   N   A   S   Y   I   S   G   Y   L   C   P   N   E   F   I   A   T   Q       120
361       aggtccactaccaggaacagttggagattttggagatgtgtgggaaacagagcaaa           420
121        G   P   L   P   G   T   V   G   D   F   W   R   M   V   W   E   T   R   A   K       140
421       aacattagtaatgctaacacagtgtttgaaaaaggacggatcagatgccatcagtattg        480
141        T   L   V   M   L   T   Q   C   F   E   K   G   R   I   R   C   H   Q   Y   W       160
481       gccagaggacaacaagccagttacctgtctttggagatatagtgattacaaagctaatgga      540
161        P   E   D   N   K   P   V   T   V   F   G   D   I   V   I   T   K   L   M   E       180
```

```
541  ggatgttcaaatagattggactatcagggatctgaaaattgaaaggcatgggagattgcat  600
181   D  V  Q  I  D  W  T  I  R  D  L  K  I  E  R  H  G  D  C  M   200

601  gactgttcgacagtgtaacttactgcctgccagagcatgggggttcctgagaacagcgc   660
201   T  V  R  Q  C  N  F  T  A  W  P  E  H  G  V  P  E  N  S  A   220

661  ccctctaattcactttgtgaagttggtcgagcaggcacatgacaccacacctat        720
221   P  L  I  H  F  V  K  L  V  R  A  S  R  A  H  D  T  T  P  M   240

721  gattgttcactgcaggcacagtatatctttttacaccagtgcattctgatctcttatca   780
241   I  V  H  C  R  H  S  I  S  F  Y  T  S  A  F  W  I  S  Y  Q   260

781  aataagggaagtaatcagcccatctgtgttttgttaactattcagcacttcagaagatggac  840
261   I  R  E  V  I  S  P  S  V  L  L  T  I  Q  H  F  R  R  W  T   280

841  tctttggacgccatggaaggtgatgttgagcttgaatgggaagaaaccactatgtaaata   900
281   L  W  T  P  W  K  V  M  L  S  L  N  G  K  K  P  L  C  K  Y   300

901  ttcagaccaaaggatacaattgaagagagattttaaatcccagggcgccaagttacccccc  960
301   S  D  Q  R  I  Q  L  E  E  I  F  K  S  Q  G  P  K  L  P  P   320

961  tcattcttccgaattgaaatgtgcaaccttaaagaaatatctgtcttctctcactgtgc  1020
321   H  S  S  E  L  K  C  A  T  L  K  K  Y  L  C  F  S  H  C  A   340

1021 ctttccaaacgattgaacatttaagactagttcttgaaaatagctaatacagaataat   1080
341   F  P  N  G  L  N  I  L  R  L  V  L  E  N  S  *               355
```

FIG. 3B

```
1081  tatttgttttgtacagaataaatattattatgcatttaaatgcttaagaaaagacatcccat  1140
1141  atgttttgaagtcctccatattttggaataagcccaatagaaaattattatatattag      1200
1201  cattaatgtttcaatgtgaatttccctatgtattggatttaatttgaggacaaaagtt      1260
1261  gtaaatgttgattcagtagtgttgtttggcttacagggtattgatgttcttgtggata      1320
1321  atttccaggactgtcataatgatctgtactccatgtacacccctgttttgaatcctc      1380
1381  tgttttatgagtgctgagatatcatctcatgatcccgaacagctgaacagtaaccccctg   1440
1441  acactgcagggattacttggcctttatacaacacagtagctcttcaggacacttagg      1500
1501  gctatttaatttcgattgtgtcttcagtttgagaacctaaaagaaaattaaaagtgcaa   1560
1561  ttgcacacatgaaattacagagtaccattctagcaaacctacatttgtaaactttaaaac  1620
1621  acaagttttxcccctgtattgtatattcaaatatatagtaaatgtatcagagtattttgc   1680
```

FIG. 3C

```
1681  ccattagatatgatcaacctaatattaacaattctgaagagtttcttcagcaaaatgta  1740
1741  tcaagagtaataaaaacactgtgcgtgtttcaagcttgtaaaccaatgatctgctgctgt  1800
1801  ggtgccaacagagacttccaaatgattatgttaaatggccgtcatttcatttcccaagg  1860
1861  ttgattttgagcagtatacttggtggaactgaaaacaaagaaattaaccatctatagcaa  1920
1921  attcaaggttttctttatagaaaatctttcagcctccatcttattaaatagtgacaatgtg  1980
1981  gtaagttttgaattatatgaactcattttgtcatagatttcaattaagagtaataatag  2040
2041  tattaattatgctctctctatgataagaagtatatcttatgcttattccgctggaacata  2100
2101  tatatatatgaaatgctatggccaataaaattgaattttaatgaaaaaaaaaaaaaaa  2160
2161  aaaaaaaaaaaa  2173
```

FIG. 3D

```
  1  MRMRPISKKSFLQHVEELCTNNNLKFQEEFSELPKFLQDLSSTDADLPWN   50
        : .. .:: ::  :.: :: :: .:-:-:--:-
  1  ..........MEMEKEFEQI..DKSGSWAAIYQDIRHEASDFPCRVAKLPKN   40

51  RAKNRFPNIKPYNNNRVKLIADASVPGSDYINASYISGYLCPNEFIATQG  100
       :: :.::.::.:-:::-:::    .:-:::::::::::---:::-
 41  KNRNRYRDVSPFDHSRIKLHQE.....DNDYINASLIKMEEAQRSYILTQG   86

101  PLPGTVGDFWRMVWETRAKTLVMLTQCFEKGRIRCHQYWPEDNKPVTVFG  150
     ::: :.:-::::-:::: ::-::::-: :.:::::-:::::::.: ::
 87  PLPNTCGHFWEMVWEQKSRGVVMLNRVMEKGSLKCAQYWPQKEEKEMIFE  136

151  D..IVITKLMEDVQIDWTIRDLKIERHG..DCMTVRQCNFTAWPEHGVPE  196
      :  :::.:: -.-:.:-:- :: :.:    :::-:::::::-:.:.:::
137  DTNLKLTLISEDIKSYYTVRQLELENLTTQETREILHFHYTTWPDFGVPE  186
```

FIG. 4A

```
197  NSAPLIHFVKLVR..ASRAHDTTPMIVHCRHSI.......SFYTSAFWISY  238
       ..:::.. ::  .:..::.::::  .:: :::
187  SPASFLNFLFKVRESGSLSPEHGPVVHCSAGIGRSGTFCLADTCLLLMD    236

239  QIREVIS...PSVLLTIQHFRRWTLWTPWKVMLSLNGKKPLCKY.......  279
     . :::     . :::..:: ::  :: .: .:.::    :.:
237  KRKDPSSVDIKKVLLEMRKFRMGLIQTADQLRFSYLAVIEGAKFIMGDSS   286

280  .SDQRIQL.EEIFKSQGPKLPPHSSELKCATLKKYLCFSHCAFPNGLNIL   327
      ::  ::  --  :.::::.. ::.    .:.  :.  ::  ---
287  VQDQWKELSHEDLEPPPEHIPPPRPPK.RILEPHNGKCREFFPNHQWVK    335

328  RLVLENS............................................  334
     :::
336  EETQEDKDCPIKEEKGSPLNAAPYGIESMSQDTEVRSRVVGGSLRGAQAA   385
```

FIG. 4B

```
  1  acaacaagccagttactgtctttggagatatagtgattacaagctaatggagatgttc   60
  1   N  K  P  V  T  V  F  G  D  I  V  I  T  K  L  M  E  D  V  Q   20

61  aaatagattggactatcaggatctgaaaattgaaggcatgggattgcatgactgtgttc  120
 21   I  D  W  T  I  R  D  L  K  I  E  R  H  G  D  C  M  T  V  R   40

121  gacagtgtaacttactgcctgccagagacatgggttcctgagaacagcgcccctctaa  180
 41   Q  C  N  F  T  A  W  P  E  H  G  V  P  E  N  S  A  P  L  I   60

181  ttcactttgtgaagttggttcgagcaagcaggcacatgacaccacacctatgattgttc  240
 61   H  F  V  K  L  V  R  A  S  R  A  H  D  T  T  P  M  I  V  H   80

241  actgcagtgctggagttggaagaactggagttttattgctctctgaccatttaacacaac  300
 81   C  S  A  G  V  G  R  T  G  V  F  I  A  L  D  H  L  T  Q  H  100
```

FIG. 5A

```
301  atataaatgaccatgattttgtgtggatatatggactagtgaactgagaagtgaaa    360
101   I  N  D  H  D  F  V  D  I  Y  G  L  V  A  E  L  R  S  E  R   120

361  gaatgtgcatggtgcagaatctggcacagtatatctttttacaccagtgcattctggatc    420
121   M  C  M  V  Q  N  L  A  Q  Y  I  F  L  H  Q  C  I  L  D  L   140

421  tcttatcaaataaggggaagtaatcagcccatctgttttgttaactattcagcacttcaga    480
141   L  S  N  K  G  S  N  Q  P  I  C  F  V  N  Y  S  A  L  Q  K   160

481  agatggactctttggacgccatggaaggtgatgttgagcttgaatgggaaga    532
161   M  D  S  L  D  A  M  E  G  D  V  E  L  E  W  E       177
```

FIG. 5B

```
  1  tattttagcttgggaagtaatacggggatatttaactcccttgggtttgaaaccatgt              60
 61  cattatgagaatgaggccaataagcaagaaatccttcctgcaacatgttgaagactttg             120
 21        M  R  M  R  P  I  S  K  K  S  F  L  Q  H  V  E  E  L  C           40
121  cacaaacaacaacctaaagtttcaagaagaaTTTTCGGAATTACCAAAATTTCTTCAGGA             180
 41   T  N  N  N  L  K  F  Q  E  E  F  S  E  L  P  K  F  L  Q  D            60
181  TCTTTCTTCAACTGATGCTGATCTGCCTTGGAATAGAGCAAAAAACCGCTTCCCAAACAT             240
 61   L  S  S  T  D  A  D  L  P  W  N  R  A  K  N  R  F  P  N  I            80
241  AAAACCATATAATAATAACAGAGTAAAGctgatagctgacgctagtgttccaggttcgga             300
 81   K  P  Y  N  N  N  R  V  K  L  I  A  D  A  S  V  P  G  S  D           100
301  ttatattaatgccagctatattctgttattctgtccaaatgaatttattgctactca               360
101   Y  I  N  A  S  Y  I  S  G  Y  L  C  P  N  E  F  I  A  T  Q           120
361  aggtccactaccaggaacagttggagattttggagaatgtgtgggaaaccagagcaaa              420
121   G  P  L  P  G  T  V  G  D  F  W  R  M  V  W  E  T  R  A  K           140
421  aacattagtaatgctaacacagtgttttgaaaaggacgatcagatgccatcagtattg              480
141   T  L  V  M  L  T  Q  C  F  E  K  G  R  I  R  C  H  Q  Y  W           160
481  gccagaggacaacaagccagttactgtctttggagatatagtgattacaaagctaatgga            540
161   P  E  D  N  K  P  V  T  V  F  G  D  I  V  I  T  K  L  M  E           180
541  ggatgttcaaatagattggactatcaggatctgaaaattgaaaggcatgggattgcat              600
181   D  V  Q  I  D  W  T  I  R  D  L  K  I  E  R  H  G  D  C  M           200
```

FIG. 6A

| | | | |
|---|---|---|---|
| 601 | gactgttcgacagtgtaacttactgcctggcagagcatggggttcctgagaacagcgc | 660 | |
| 201 | T V R Q C N F T A W P E H G V P E N S A | 220 | |
| 661 | ccctctaattcactttgtgaagttggttcgagcaagcaggcacatgacacaccacctat | 720 | |
| 221 | P L I H F V K L V R A S R A H D T T P M | 240 | |
| 721 | gattgttcactgcagtgctggagagttggaagaactggagttttattgctctgaccattt | 780 | |
| 241 | I V H C S A G V G R T G V F I A L D H L | 260 | |
| 781 | aacacaacatataaatgaccatgattttgtggatatatggactagtagctgaactgag | 840 | |
| 261 | T Q H I N D H D F V D I Y G L V A E L R | 280 | |
| 841 | aagtgaaagaatgtgcatggtgcagaatctggcacagtatatctttttacaccagtgcat | 900 | |
| 281 | S E R M C M V Q N L A Q Y I F L H Q C I | 300 | |
| 901 | tctggatctcttatcaaatagggaagtaatcagcccatctgttttgttaactattcagc | 960 | |
| 301 | L D L L S N K G S N Q P I C F V N Y S A | 320 | |
| 961 | acttcagaagatgggactctttggacgccatggaaggtgatgttgagcttgaatgggaaga | 1020 | |
| 321 | L Q K M D S L D A M E G D V E L E W E E | 340 | |
| 1021 | aaccactatgtaaatattcagaccaaaggatacaattggaagagatttttaaatcccagg | 1080 | |
| 341 | T T M * | 343 | |
| 1081 | ggccaaagttaccccctcattcttccgaattgaatgtgcaaccttaaagaatatctat | 1140 | |
| 1141 | gcttctctcactgtgcctttccaaacgattgaacatttaagactagttcttgaaata | 1200 | |

FIG. 6B

```
1201  gctaatacagaataattattgttttgtacagaataatattatgcattttaaatgctta  1260
1261  agaaaagacatcccatatgttttttgaagtcctccatatttgaataagccaaatagaaa  1320
1321  attattattatattagcattaatgtttcaatgtattccctatgtattggatttaat    1380
1381  tttgaggacaaaagttgtaaatgttgattcagtagtgttgttttggcttacagggtattg  1440
1441  atgtttcttgtggataattccaggactgtcataatgatctgtacttccatgatcccc    1500
1501  tgtgttttgaatcctctgttttatgagtgctgagatatcatcatgatcccgaacagct   1560
1561  gaacagtaaccccctgacactgcaggattactggcctttatacaacacagtagctc     1620
1621  ttcaggacacttaggctattaattcgattgtgtcttcagtttgagaaccttaaaag     1680
1681  aaaattaaaagtgcaattgcacacacatgaaattacagagtaccattctagcaaacctacat 1740
1741  ttgtaactttaaaacacaagttttxcccctgtattgtatattcaaatatatagtaaat   1800
```

FIG. 6C

```
1801  gtatcagagtatttgcccattagatatgatcaacctaatattaacaattctgaagagttt  1860
1861  cttcagcaaaaatgtatcaagagtaataaaaacactgtgcgtgttcaagcttgtaaacc   1920
1921  aatgatctgctgtggtgcaacagagacttccaaatgattatgttaaatggccgtc       1980
1981  atttcatttcccaaggttgattttgagcagtatacttggtggaactgaaacaaagaaat   2040
2041  taaccatctatagcaaattcaaggtttcttttatagaaaatctttcagcctccatcttatt 2100
2101  aaatagtgacaatgtggtaagttttgaattatatgaactcatttgtcatagatttcaat   2160
2161  taagagtaataaaatagtattaattatgctctcctatgataagagtatatcttatgctta  2220
2221  tttccgctggaacatatatatatgaaatgctatggccaataaattgaattttaatga     2280
2281  aaaaaaaaaaaaaaaaaaaaaaaaaaaaa                                 2309
```

FIG. 6D

```
CD45-D1    MNVEP-IHADILLETYKRKIADEGRLFLAEFQSIPRVFSKFPIKEARKPFNQNKNRYVDI
LAR-D1     MRDHPPIPITDLADNIERLKANDGLKFSQEYESIDPG-QQFTWENSNLEVNKPKNRYANV
PTP-18     MEME----------KEFEQI--DKSGSWAAIYQDIRHEASDFPCRVAKLPKNKNRNRYRDV
PTP-S31-D  MRMRP-ISKKSFLQHVEELCTNNNLKFQEEFSELPKFLQDLSSTDADLPWNRAKNRFPNI
              *                .              . *.  .**. ..

CD45-D1    LPYDYNRVELSEINGDAGSNYINASYIDGFKEPRKYIAAQGPRDETVDDFWRMIWEQKAT
LAR-D1     IAYDHSRVILTSIDCVPGSDYINANYIDGYRKQNAYIATQGPLPETMGDFWRMVWEQRTA
PTP-18     SPFDHSRIKLHQEDN------DYINASLIKMEEAQRSYILTQGPLPNTCGHFWEMVWEQKSR
PTP-S31-D  KPYNNNRVKLIADASVPGSDYINASYISGYLCPNEFIATQGPLPGTVGDFWRMVWETRAK
              ... .*. *        .****. *    .* .*** * ..** *.** ..

CD45-D1    VIVMVTRCEEGNRNKCAEYWPSMEEGTRAFGD--VVVKINQHKRCPDYIIQKLNIVNKKE
LAR-D1     TVVMMTRLEEKSRVKCDQYWPAR--GTETCGL--IQVTLLDTVELATYTVRTFAL-HKSG
PTP-18     GVVMLNRVMEKGSLKCAQYWPQKEEKEMIFEDTNLKLTLISEDIKSYYTVRQLELENLTT
PTP-S31-D  TLVMLTQCFEKGRIRCHQYWPEDNKPVTVFGD--IVITKLMEDVQIDWTIRDLKIERHGD
              .**. . *    .* .***              . .           ....  .

CD45-D1    KATGREVTHIQFTSWPDHGVPEDPHLLLKLRRRVNAFSNFFS--GPIVVHCSAGVGRTGT
LAR-D1     SSEKRELRQFQFMAWPDHGVPEYPTPILAFLRRVKACNPLDA--GPMVVHCSAGVGRTGC
PTP-18     -QETREILHFHYTTWPDFGVPESPASFLNFLFKVRESGSLSPEHGPVVVHCSAGIGRSGT
PTP-S31-D  CMT--VRQCNFTAWPEHGVPENSAPLIHFVKLVRASRAHDT--TPMIVHCSAGVGRTGV
              . ... .**. **** . .. *    *..******.**.*

CD45-D1    YIGIDA----MLEGLEAENKVDVYGYVVKLRRQRCLMVQVEAQYILIHQALVEYNQFGETE
LAR-D1     FIVIDA----MLERMKHEKTVDIYGHVTCMRSQRNYMVQTEDQYVF HEALLEAATCGHTE
PTP-18     FCLADTCLLLMDKRKDPSSVDIKKVLLEMRKFRMGLIQTADQLRFSYLAVIEGAKFIMGD
PTP-S31-D  FIALDH----LTQHINDHDFVDIYGLVAELRSERMCMVQNLAQYIFLHQCILDLLSNKGSN
              *        **.  . .* * ..*  *  .    ...

FIG.7
```

```
  1        gccttcgtcaactaattctctcttaaatttagaacttcatcccaataacttattagaaaaa   60
 61        aaagaaagtagaataggttctatggaattaaaacaagaaaaagaagtcgagtagctataa   120
 21                           N  K  K  K  K  K  S  S  S  Y  K           40
121        atttgcaacatattcagagaggtgattttaacaaggaaattatttgactaaatgtcttta   180
 41         F  A  T  Y  S  E  R                                         60
181        cttaaaagaaaactaaacctaattttatatactttgtgaaactccttcttggactt      240
241        tactccgcttgtttagaattcgacagaggtggcacatactctcctcag              300
 81              I  R  Q  K  Q  K  E  G  G  T  Y  S  P  Q              100
301        gatgcagaaattattgacactaaattgaagctggatcagctcatcacagtggcagacctg   360
101         D  A  E  I  I  D  T  K  L  K  L  D  Q  L  I  T  V  A  D  L 120
361        gaactgaaggacgagagattaacgcgatactcttcattttcttttagacgcaaggagatt   420
121         E  L  K  D  E  R  L  T  R  Y  S  S  F  F  F  R  R  K  E  I 140
421        tttgtcatccagttacttagttatagaaatccatcaagcaataagcaagaaatccttc    480
141         F  V  I  Q  L  L  S  Y  R  K  S  I  K  P  I  S  K  K  S  F 160
481        ctgcaacatgttgaagagctttgcacaaacaacctaagtttcaagaagaatttcg        540
161         L  Q  H  V  E  E  L  C  T  N  N  N  L  K  F  Q  E  E  F  S 180
541        gaattaccaaaatttcttcaggatctgtcttcaactgatgctgatctgccttggaataga   600
181         E  L  P  K  F  L  Q  D  L  S  S  T  D  A  D  L  P  W  N  R 200
```

FIG. 9A

| | | |
|---|---|---|
| 601 | gcaaaaaccgcttcccaaacatataaaccatataataacagagtaaagctgatagct | 660 |
| 201 | A K N R F P N I K P Y N N N R V K L I A | 220 |
| 661 | gacgctagtgttccaggttcggattatattaatgccagctatattctggttattatgt | 720 |
| 221 | D A S V P G S D Y I N A S Y I S G Y L C | 240 |
| 721 | ccaaatgaatttattgctactcaaggtccactccaggaacagttggagattttggaga | 780 |
| 241 | P N E F I A T Q G P L P G T V G D F W R | 260 |
| 781 | atggtgtgggaaaccagagcaaaaacattagtaatgctaacacagtgttttgaaaaagga | 840 |
| 261 | M V W E T R A K T L V M L T Q C F E K G | 280 |
| 841 | cggatcagatgccatcagtattggccagaggacaacaagccagttactgtctttggagat | 900 |
| 281 | R I R C H Q Y W P E D N K P V T V F G D | 300 |
| 901 | atagtgattacaaagctaatggaggatgttcaaatagattggactatcaggatctgaaa | 960 |
| 301 | I V I T K L M E D V Q I D W T I R D L K | 320 |
| 961 | attgaaaggcatggggattgcatgactgttcgacagtgtaacttttactgcctggccagag | 1020 |
| 321 | I E R H G D C M T V R Q C N F T A W P E | 340 |
| 1021 | catgggttcctgagaacagcgcccctctaattcactttgtgaagttggttcgagcaagc | 1080 |
| 341 | H G V P E N S A P L I H F V K L V R A S | 360 |
| 1081 | agggcacatgacaccacctatgattgttcactgcagtgctgagtttggaagaactgga | 1140 |
| 361 | R A H D T T P M I V H C S A G V G R T G | 380 |

FIG. 9B

```
1141  gttttattgctctggaccatttaacacaacatataaatgaccatgatttttgtggatata   1200
 381   V  F  I  A  L  D  H  L  T  Q  H  I  N  D  H  D  F  V  D  I     400

1201  tatggactagtagctgaactgagaagtgaaagaatgtgcatggtgcagaatctggcacag   1260
 401   Y  G  L  V  A  E  L  R  S  E  R  M  C  M  V  Q  N  L  A  Q     420

1261  tatatcttttacaccagtgcattctggatctcttatcaataagggaagtaatcagccc     1320
 421   Y  I  F  L  H  Q  C  I  L  D  L  L  S  N  K  G  S  N  Q  P     440

1321  atctgttttgttaactattcagcacttcagaagatggactctttggacgccatggaaggt   1380
 441   I  C  F  V  N  Y  S  A  L  Q  K  M  D  S  L  D  A  M  E  G     460

1381  gatgttgagcttgaatgggaagaaaccactatgtaaatattcagaccaaaggatacaatt   1440
 461   D  V  E  L  E  W  E  E  T  T  M  *                             471

1441  ggaagagatttttaaatcccagggccaaagttaccccctcattcttccgaattgaaatg   1500

1501  tgcaaccttaaagaaatatctatgcttctctcactgtgcctttccaaacgattgaacat    1560

1561  tttaagactagtcttgaaatagctaatacagaataattatttgttttgtacagaataa    1620
```

FIG. 9C

```
1621  atattatgcatttaaagaaaagacatcccatatgttttgaagtcctccata  1680
1681  ttttgaataagccaaatagaaaattattattagcattaatgtttcaatgtttcatgtgaat  1740
1741  tttccctatgtattggatttaatttgaggacaaagttgtaaatgttgattcagtagtg  1800
1801  ttgttttggcttacagggtattgatgttcttcttgtggataattcaggactgtcataatg  1860
1861  atctgtacttccatgtacaccccctgtttgaatcctctgttttatgagtgctgagata  1920
1921  tcatctcatgatcccgaacagctgaacagtaaccccctgacactgcagggattacttggc  1980
1981  ctttatacaacacacagtagctcttcaggacacttaggctatttaatttcgattgtgt  2040
2041  cttcagtttgagaacctaaaagaaattaaaagtgcaattgcacacatgaaattacaga  2100
2101  gtaccattctagcaaacctacatttgtaaactttaaaacacaagttttxcccctgtatt  2160
2161  gtatattcaaatatatagtaaatgtatcagagtatttgcccattagatatgatcaaccta  2220
2221  atattaacaattctgaagagtttcttcagcaaaatgtatcaagagtaataaaacactg  2280
```

FIG. 9D

| | | |
|---|---|---|
| 2281 | tgcgtgtttcaagcttgtaaaccaatgatctgtctgctgtggtgccaacagagacttccaa | 2340 |
| 2341 | atggattatgttaaatggccgtcatttcatttcccaaggttgattttgagcagtatactt | 2400 |
| 2401 | ggtggaactgaaacaaagaaattaaccatctatagcaaattcaaggtttctttatagaa | 2460 |
| 2461 | aatctttcagcctccatcttattaaatagtgacaatgtggtaagttttgaattatatgaa | 2520 |
| 2521 | ctcattttgtcatagatttcaattaagagtaataaatagtattattatgctctttctatg | 2580 |
| 2581 | ataagaagtatatcttatgcttattccgctggaacatatatatatgaaatgctatgg | 2640 |
| 2641 | ccaataaaattgaattttaatgaaaaaaaaaaaaaaaaaaaaaaaaa | 2692 |

FIG. 9E

```
S31-14    ------------------IRQKQKEGGTYSPQDAEIIDTKLKLDQLITVADLELKDERLTR----
S31-2     ------------------IRQKQKEGGTYSPQDAEIIDTKLKLDQLITVADLELKDERLTR----
S31-5     ------------------IRQKQKEGGTYSPQDAEIIDTKLKLDQLITVADLELKDERLTRYSSF
S31-63    KSSSYKFATYSERIRQKQKEGGTYSPQDAEIIDTKLKLDQLITVADLELKDERLTRYSSF
S31-III   EKQ-------VTTIRQKQKEGGTYSPQDAEIIDTKLKLDQLITVADLELKDERLTRYSSF
                     ******.***************************************

S31-14    ----------------PISKK
S31-2     ----------LLSYRKSIKPISKK
S31-5     FFRRKEIFVIQLLSYRKSIKPISKK
S31-63    FFRRKEIFVIQLLSYRKSIKPISKK
S31-III   FFRRKEIFVIQLLSYRKSIKPISKK
                              *****
```

```
  1    ggaaggtctggagccagtacctgtggatacaaagttcccagtgttcccacaaatattgcttttctgatgttcagtcaactagtgca    90
  1    G  R  S  G  S  Q  Y  P  V  D  T  K  V  P  S  V  P  T  N  I  A  F  S  D  V  Q  S  T  S  A    30

91    acattgacatggataagacctgacactatccttggctacttcaaaattaccaactcgtgctcaaaaatgcaaagaa              180
 31    T  L  T  W  I  R  P  D  T  I  L  G  Y  F  Q  N  Y  K  I  T  T  Q  L  R  A  Q  K  C  K  E    60

181    tgggaatccgaagaatgtgttgaatatcaaaaaattcaatacctctatgagctcactgaaggagacagtatggattaaggaa         270
 61    W  E  S  E  E  C  V  E  Y  Q  K  I  Q  Y  L  Y  E  A  H  L  T  E  E  T  V  Y  G  L  K  K    90

271    tttagatggtatagattccaagtggctgccagcaccaatgctatggcaatgcttcaaactggattttctacaaaactctgcctggc   360
 91    F  R  W  Y  R  F  Q  V  A  A  S  T  N  A  G  Y  G  N  A  S  N  W  I  S  T  K  T  L  P  G   120

361    cctccagatggtcctcctgaaaatgttcatgtagtagcaacatcacctttagcatcagcataagctggagtgacataagctggagt   450
121    P  P  D  G  P  P  E  N  V  H  V  V  A  T  S  P  F  S  I  S  W  S  E  P  A  V  I  T         150

451    ggaccaacatgttatctgattgatgtcaaatcggtagataatgaatttaatatctcttcatcaagtcaaatgaagaaataaaacc    540
151    G  P  T  C  Y  L  I  D  V  K  S  V  D  N  D  E  F  N  I  S  F  I  K  S  N  E  E  N  K  T   180

541    atagaaattaaagatttagaaatattcacaagatattcacactcttagatgatcactgggaacattagtgctgacattgtgaaggg   630
181    I  E  I  K  D  L  E  I  F  T  R  Y  S  V  V  I  T  A  F  T  G  N  I  S  A  A  Y  V  E  G   210

631    aagtcaagtgctgaatgattgttactcttcctctccaacctaatgaaatatccagtatatcaagctctggtttaccagaagatgaa    720
211    K  S  S  A  E  M  I  V  T  T  L  E  S  A  P  K  D  P  P  N  N  M  T  F  Q  K  I  P  D  E   240

721    gttacaaaatttcaattaacgttcctccttcctccttcaacctaatgaaatatccagtatatcaagctctggtttaccagaagatgat    810
241    V  T  K  F  Q  L  T  F  L  P  P  S  Q  P  N  G  N  I  Q  V  Y  Q  A  L  V  Y  R  E  D  D   270

811    cctactgtctgtccagattcacaacctcagtattatacagaaaccaacacattcgtcattgcaatgctagaaggactaaaggtggacat    900
271    P  T  A  V  Q  I  H  N  L  S  I  I  Q  K  T  N  T  F  V  I  A  M  L  E  G  L  K  G  G  H   300
```

```
 901  acatacaatcagtgtttacgcagtcaatagtgctgatgcaggtccaaggttccgatgagaataaccatgagaataaccatgagaataccatcaagctccagca  990
 301   T  Y  N  I  S  V  Y  Y  A  V  N  S  A  G  A  G  P  K  V  P  M  R  I  T  M  D  I  K  A  P  A   330

991  cgaccaaaaccaaccaccctatttatgatgccacaggaaaactgcttgtgacttcaacaacaattacaatcagaatgcaatatgt  1080
 331   R  P  K  T  K  P  T  P  I  Y  D  A  T  G  K  L  L  V  T  S  T  T  I  T  I  R  M  P  I  C   360

1081  tactacagtgatgatcatggaccaataaaaatgtacaagtgctacaagtgttgacagaacaggagctcagcatgatgaaatgtaacaaggtgg  1170
 361   Y  Y  S  D  D  H  G  P  I  K  N  V  Q  V  L  V  T  E  T  G  A  Q  H  D  G  N  V  T  K  W   390

1171  tatgatgcatatttaataagcaaggccatatttacaaatgaaggctttcctaaccctccatgtcagaggaagacaaagttagt  1260
 391   Y  D  A  Y  F  N  K  A  R  P  Y  F  T  N  E  G  F  P  N  P  P  C  T  E  G  K  T  K  F  S   420

1261  ggcaatgaagaaatctacatcattagagctacaaatatcatggtgctgataatgcatgatcctgcaatgaagacaaatttgcaatgaccactgaacca  1350
 421   G  N  E  E  I  Y  I  I  G  A  D  N  A  C  M  I  P  G  N  E  D  K  I  C  N  G  P  L  K  P   450

1351  aaaagcaatacttattaaattagagctacaaatattatggacaattactgactctgattattctgacctgttaagacttaggg  1440
 451   K  K  Q  Y  L  F  K  F  R  A  T  N  I  M  G  Q  F  T  D  S  D  Y  S  D  P  V  K  T  L  G   480

1441  gaaggacttcagaagaaccgtagagtagaagatcattcttccgtcacttgtatcctttcaataattctcttgaacagctattttgca  1530
 481   E  G  L  S  E  R  T  V  E  I  I  L  S  V  T  L  C  I  L  S  I  I  L  L  G  T  A  I  F  A   510

1531  tttgcaagaattcgacagaagcaggaactgaggacgagaagaaggtggcacatactctcctcaggatgcagaaattattgacactaaattgaagctggatcag  1620
 511   F  A  R  I  R  Q  K  Q  K  E  G  G  T  Y  S  P  Q  D  A  E  I  I  D  T  K  L  K  L  D  Q   540

1621  ctcatcacagtggcagacctggaactgaaggacgagagattaacgcgatactcttcatttttcttagagcaaggagattttgtcatc  1710
 541   L  I  T  V  A  D  L  E  L  K  D  E  R  L  T  R  Y  S  S  F  F  F  R  R  K  E  I  F  V  I   570

1711  cagttacttagttataagaaatccatcaagcaagaaatcctcctgcaacatgttgaagagctttgcacaaacaacaaccta  1800
 571   Q  L  L  S  Y  R  K  S  I  K  P  I  S  K  K  S  F  L  Q  H  V  E  E  L  C  T  N  N  N  L   600
```

FIG.12B

```
1801  aagtttcaagagagaatttcggaattaccaaaatttcttcaactgatgatgcttcttcaggatctttcttcaactgatgctgatctgccttggaatagagcaaaaac  1890
 601   K  F  Q  E  E  F  S  E  L  P  K  F  L  Q  D  L  S  S  T  D  A  D  L  P  W  N  R  A  K  N              630

1891  cgcttcccaaacataaacatataataacagagtaacgctgacgctagtgacgctagtgttccaggttcggattatattaatgccagc                     1980
 631   R  F  P  N  I  K  P  Y  N  N  N  R  V  K  L  I  A  D  A  S  V  P  G  S  D  Y  I  N  A  S              660

1981  tatatttctgttattatgtccaatgaatttattgctactcaaggtccactaccaggacagttggagattttggagatggtgtgg                        2070
 661   Y  I  S  G  Y  L  C  P  N  E  F  I  A  T  Q  G  P  L  P  G  T  V  G  D  F  W  R  M  V  W              690

2071  gaaccagagcaaaacattagtaatgctaacacagtgtttgaaaaaggacagatgccatcagtattggccagagacaacaag                           2160
 691   E  T  R  A  K  T  L  V  M  L  T  Q  C  F  E  K  G  R  I  R  C  H  Q  Y  W  P  E  D  N  K              720

2161  ccagttactgtctttggagatatagtgattacagcagtgttcaaatagattggactatcaggatctgaaattgaaagg                              2250
 721   P  V  T  V  F  G  D  I  V  I  T  K  L  M  E  D  V  Q  I  D  W  T  I  R  D  L  K  I  E  R              750

2251  catggggattgcatgactgcttgcagagacagtgggttcctgccagagcatggtgtcctgagaacagcgccctctaattcacttt                       2340
 751   H  G  D  C  M  T  V  R  Q  C  N  F  T  A  W  P  E  H  G  V  P  E  N  S  A  P  L  I  H  F              780

2341  gtgaagttggttcgagcaagcaggcacatgacttgttcactgcagtgttgaagaactggagttgaggactggagttttatt                           2430
 781   V  K  L  V  R  A  S  R  A  H  D  T  T  P  M  I  V  H  C  S  A  G  V  G  R  T  G  V  F  I              810

2431  gctctggaccattaacacaacacatataatgaccatgatttgtggatatatatggactagtgctgaactgagaagtgaaagaatgc                      2520
 811   A  L  D  H  L  T  Q  H  I  N  D  H  D  F  V  D  I  Y  G  L  V  A  E  L  R  S  E  R  M  C              840

2521  atggtgcagaatctggcacagtatatctttttacaccagtgcattctggatctcttatcaaataagggagtaataatcagccatctgtttt                 2610
 841   M  V  Q  N  L  A  Q  Y  I  F  L  H  Q  C  I  L  D  L  L  S  N  K  G  S  N  Q  P  I  C  F              870

2611  gttaactattcagcacttcagaagatggactctttggacgccatggaagtgatgttgagcttgaatgggagaaacactatgtaaata                     2700
 871   V  N  Y  S  A  L  Q  K  M  D  S  L  D  A  M  E  G  D  V  E  L  E  W  E  E  T  T  M  *               900
```

FIG.12C

```
2701  ttcagaccaaggatacaattggaagagatttttaaatcccagggccaaagttacccctccttcttccgaattgaaatgtcaaccttt  2790
2791  aagaaatatctatgcttctctcactgtgccttccaaacggattgaacattttaagactagttcttgaaaatagctaatacagaataat  2790
2881  tatttgttttgtacagaataatattatgcattttaaatgcttaagaaagacatccatatgttttgaagtcctccatatttttggaat  2970
2971  aagccaaatagaaaattattattatatattagcattaatgtgttccatgttcaatgttcaatttgaatttccctatgtattaatttgaggacaaaagtt  3060
3061  gtaaatgttgattcagtagtgttgttttggcttacagggtattgatgttcttgtggataattccaggactgtcataatgatctgtact  3150
3151  tccatgtacccccctgtgtttgaatcctctgttttatggtgctgagatatcatctcatgatccgaacagctgaacagtaaccccctg  3240
3241  acactgcaggattacttggcctttatacaacacacagtagctcttcaggacacttaggctattttaattcgattgtgtcttcagttt  3330
3331  gagaacctaaaagaaattaaaagtgcaattgcacacatgaaattacagagtaccattctagcaaactacattgtaaactttaaaac  3420
3421  acaagtttxcccctgtattgtatattcagcaaaatgtatcaagagtaataaaacactgtgcgtgtttcaagcttgtaaaccaatgatctgctgctgt  3510
3511  attctgaagagttcttcagcaaaatggattatgttaatggccgtcatttcattcccaaggttgatttgacagtatactggtggaact  3600
3601  ggtgccaacagagacttccaaatggatctagcaaattcaggtttctttatttatgagcctccatcttattaaatagtgacaatgtg  3690
3691  gaaaacaaagaaattaaccatctatagcaaattaaccatctatagcaaatttcaggtttcttatttatgaaaatctttcagcctccatcttattaaatagtattaattatgctctctctatgtataagaagt  3780
3781  gtaagtttgaattatatgaactcattttgtcatagatttcaattaagagtaataaataatatatatgctctctctatgtataagaagt  3870
3871  atatcttatgcttattccgctggaacatatatatatgaaatgctatggccaataaattgaatttaatgaaaaaaaaaaaaa  3960
3961  aaaaaaaaaa  3973
```

FIG.12D

```
PTP-S31      GNEDKICNGPLPKPKKQYLFKFRATNIMCQFTD.SDYSDPVK
             ::.:||.:.||||..||.|||..:||.|.:||:.||:||||
IL2R-beta 188 .QKQEWICLETLTPDTQYEFQVRVKPLQGEFTTWSPWSQPLA 228
```

FIG.13

```
S31-FN-4           PSV    PT N IA F SD V QST    SA TLT W IRPDTILGYFQN Y KITTQ LRAQKCKEWESEECVEYQKIQYLYEAHLTEETVYG
S31-FN-3   GPPDG P PE N VH V VA T SPF           SI SIS W SEPAVITGPTC Y LIDVK SVDNDEFNISFIKSNEENKTIEIKD
S31-FN-2   APKD P PN N MT F QK I PDEVT           KF QLT F LPPSQPNGNIQV Y QALVY REDDPTAVQIHNLSIIQKTNTFVIAMLEG
S31-FN-1         P IK N VQ V LV T ETGAQHD GN VTK W YDAYFNKARP    Y FTNEG FPNPPCTEGKTKFSGNEEIYIIGADNACMIPGNEDKICNGP
FN-III           LS P PT N LH L EA N PDTG   VL TVS W ERSTTPDITG     Y RITTI PTMGQQGNSLEEVVHADQSSCTPDN

S31-FN-4   L K KF RW Y RFQ V A A S T  N AGYGNASNWISTKTLP
S31-FN-3   L E IF TR Y SVV I T A F TG N ISAAYVEGKSSAEMIVTTLES
S31-FN-2   L K GG HT Y NIS V Y A V    N SAGAGPKVPMRITMQIKAPARPKTKPTP
S31-FN-1   L K PK KQ Y LFK F R A T    N IMGQFTDSDYSDPVKTLGEGLSERTVE
FN-III     L S PG LE Y NVS V Y T V KD D KESVPISDTIIP
```

FIG.14

| | |
|---|---|
| IGF1R | LHGLKPWTQYAVYVKAVTLTMVENDHIRGAKSEILYIRTNASVPSIPLDVLS |
| IR | MRGLKPWTQYAIFVKTL—VTFSDERRTYGAKSDIIYVQTDATNPSVPLDPIS |
| IRR | LASLKPWTQYAVFVRAITLTTEEDSPHQGAQSPIVYLRTLPAAPTVPQDVIS |
| PTPS31 | IKDLEIFTRYSVVITAFT—GNISAAYVEGKSSAEMIVTTLESAPKGPPNNMT |
| | . *. *. . * . . |

| | |
|---|---|
| IGF1R | ——ASNSSSQLIVKWNPPSLPNGNLSYY—IVRWQRQPQDGYLYRHNYCSKD |
| IR | ——VSNSSSQIILKWKPPSDPNGNITHY—LVFWERQAEDSELFELDYCLKG |
| IRR | ——TSNSSSHLLVRWKPPTQRNGNLTYY—LVLWQRLAEDGDLYLNDYCHRG |
| PTPS31 | FQKIPDEVTKFQLTFLPPSQPNGNIQVYQALVYREDDPTAVQIHNLSIIQKT |

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 7 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:1:

Lys Cys Xaa Xaa Tyr Trp Pro
1               5

( 2 ) INFORMATION FOR SEQ ID NO:2:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: unknown ( i i ) MOLECULE TYPE: peptide ( x i ) SEQUENCE DESCRIPTION: SEQ ID NO:2:

```
His  Cys  Ser  Xaa  Gly  Xaa  Gly  Arg  Xaa  Gly
 1              5                        10
```

( 2 ) INFORMATION FOR SEQ ID NO:3:

( i ) SEQUENCE CHARACTERISTICS:
       ( A ) LENGTH: 321 base pairs
       ( B ) TYPE: nucleic acid
       ( C ) STRANDEDNESS: double
       ( D ) TOPOLOGY: unknown ( i i ) MOLECULE TYPE: cDNA ( x i ) SEQUENCE DESCRIPTION: SEQ ID NO:3:

```
GAAACCAGAG  CAAAAACATT  AGTAATGCTA  ACACAGTGTT  TTGAAAAAGG  ACGGATCAGA         60

TGCCATCAGT  ATTGGCCAGA  GGACAACAAG  CCAGTTACTG  TCTTTGGAGA  TATAGTGATT        120

ACAAAGCTAA  TGGAGGATGT  TCAAATAGAT  TGGACTATCA  GGGATCTGAA  AATTGAAAGG        180

CATGGGGATT  GCATGACTGT  TCGACAGTGT  AACTTTACTG  CCTGGCCAGA  GCATGGGGTT        240

CCTGAGAACA  GCGCCCCTCT  AATTCACTTT  GTGAAGTTGG  TTCGAGCAAG  CAGGGCACAT        300

GACACCACAC  CTATGATTGT  T                                                    321
```

( 2 ) INFORMATION FOR SEQ ID NO:4:

( i ) SEQUENCE CHARACTERISTICS:
       ( A ) LENGTH: 107 amino acids
       ( B ) TYPE: amino acid
       ( C ) STRANDEDNESS: single
       ( D ) TOPOLOGY: unknown ( i i ) MOLECULE TYPE: protein ( x i ) SEQUENCE DESCRIPTION: SEQ ID NO:4:

```
Glu  Thr  Arg  Ala  Lys  Thr  Leu  Val  Met  Leu  Thr  Gln  Cys  Phe  Glu  Lys
 1              5                        10                       15

Gly  Arg  Ile  Arg  Cys  His  Gln  Tyr  Trp  Pro  Glu  Asp  Asn  Lys  Pro  Val
           20                        25                       30

Thr  Val  Phe  Gly  Asp  Ile  Val  Ile  Thr  Lys  Leu  Met  Glu  Asp  Val  Gln
               35                   40                   45

Ile  Asp  Trp  Thr  Ile  Arg  Asp  Leu  Lys  Ile  Glu  Arg  His  Gly  Asp  Cys
          50                   55                   60

Met  Thr  Val  Arg  Gln  Cys  Asn  Phe  Thr  Ala  Trp  Pro  Glu  His  Gly  Val
 65                   70                        75                            80

Pro  Glu  Asn  Ser  Ala  Pro  Leu  Ile  His  Phe  Val  Lys  Leu  Val  Arg  Ala
                    85                   90                        95

Ser  Arg  Ala  His  Asp  Thr  Thr  Pro  Met  Ile  Val
                    100                  105
```

( 2 ) INFORMATION FOR SEQ ID NO:5:

( i ) SEQUENCE CHARACTERISTICS:
       ( A ) LENGTH: 385 amino acids
       ( B ) TYPE: amino acid ( C ) STRANDEDNESS: single
( D ) TOPOLOGY: unknown ( i i ) MOLECULE TYPE: protein ( x i ) SEQUENCE DESCRIPTION: SEQ ID NO:5:

```
Met  Glu  Met  Glu  Lys  Glu  Phe  Glu  Gln  Ile  Asp  Lys  Ser  Gly  Ser  Trp
 1              5                       10                       15
Ala  Ala  Ile  Tyr  Gln  Asp  Ile  Arg  His  Glu  Ala  Ser  Asp  Phe  Pro  Cys
               20                       25                  30
Arg  Val  Ala  Lys  Leu  Pro  Lys  Asn  Lys  Asn  Arg  Asn  Arg  Tyr  Arg  Asp
          35                       40                  45
Val  Ser  Pro  Phe  Asp  His  Ser  Arg  Ile  Lys  Leu  His  Gln  Glu  Asp  Asn
     50                  55                       60
Asp  Tyr  Ile  Asn  Ala  Ser  Leu  Ile  Lys  Met  Glu  Glu  Ala  Gln  Arg  Ser
65                       70                  75                            80
Tyr  Ile  Leu  Thr  Gln  Gly  Pro  Leu  Pro  Asn  Thr  Cys  Gly  His  Phe  Trp
                    85                       90                            95
Glu  Met  Val  Trp  Glu  Gln  Lys  Ser  Arg  Gly  Val  Val  Met  Leu  Asn  Arg
                    100                      105                 110
Val  Met  Glu  Lys  Gly  Ser  Leu  Lys  Cys  Ala  Gln  Tyr  Trp  Pro  Gln  Lys
               115                      120                 125
Glu  Glu  Lys  Glu  Met  Ile  Phe  Glu  Asp  Thr  Asn  Leu  Lys  Leu  Thr  Leu
          130                      135                 140
Ile  Ser  Glu  Asp  Ile  Lys  Ser  Tyr  Tyr  Thr  Val  Arg  Gln  Leu  Glu  Leu
145                      150                      155                      160
Glu  Asn  Leu  Thr  Thr  Gln  Glu  Thr  Arg  Glu  Ile  Leu  His  Phe  His  Tyr
                    165                      170                 175
Thr  Thr  Trp  Pro  Asp  Phe  Gly  Val  Pro  Glu  Ser  Pro  Ala  Ser  Phe  Leu
                    180                      185                 190
Asn  Phe  Leu  Phe  Lys  Val  Arg  Glu  Ser  Gly  Ser  Leu  Ser  Pro  Glu  His
               195                      200                 205
Gly  Pro  Val  Val  His  Cys  Ser  Ala  Gly  Ile  Gly  Arg  Ser  Gly  Thr
          210                      215                 220
Phe  Cys  Leu  Ala  Asp  Thr  Cys  Leu  Leu  Leu  Met  Asp  Lys  Arg  Lys  Asp
225                      230                      235                      240
Pro  Ser  Ser  Val  Asp  Ile  Lys  Lys  Val  Leu  Leu  Glu  Met  Arg  Lys  Phe
                    245                      250                 255
Arg  Met  Gly  Leu  Ile  Gln  Thr  Ala  Asp  Gln  Leu  Arg  Phe  Ser  Tyr  Leu
               260                      265                 270
Ala  Val  Ile  Glu  Gly  Ala  Lys  Phe  Ile  Met  Gly  Asp  Ser  Ser  Val  Gln
          275                      280                 285
Asp  Gln  Trp  Lys  Glu  Leu  Ser  His  Glu  Asp  Leu  Glu  Pro  Pro  Pro  Glu
     290                      295                 300
His  Ile  Pro  Pro  Pro  Arg  Pro  Pro  Lys  Arg  Ile  Leu  Glu  Pro  His
305                      310                      315                      320
Asn  Gly  Lys  Cys  Arg  Glu  Phe  Phe  Pro  Asn  His  Gln  Trp  Val  Lys  Glu
               325                      330                 335
Glu  Thr  Gln  Glu  Asp  Lys  Asp  Cys  Pro  Ile  Lys  Glu  Glu  Lys  Gly  Ser
          340                      345                 350
Pro  Leu  Asn  Ala  Ala  Pro  Tyr  Gly  Ile  Glu  Ser  Met  Ser  Gln  Asp  Thr
          355                      360                 365
Glu  Val  Arg  Ser  Arg  Val  Val  Gly  Gly  Ser  Leu  Arg  Gly  Ala  Gln  Ala
     370                      375                 380
Ala
```

( 2 ) INFORMATION FOR SEQ ID NO:6:

( i ) SEQUENCE CHARACTERISTICS:
        ( A ) LENGTH: 2173 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: misc_feature
        ( B ) LOCATION: 1630
        ( D ) OTHER INFORMATION: /note= "N=x=unknown nucleotide"

( x i ) SEQUENCE DESCRIPTION: SEQ ID NO:6:

```
TATTTTAGCT  TGGGAAGTAA  TACGGGGATA  TTTAAACTCC  TTGGGGTTTG  AAAACCATGT    60
CATTATGAGA  ATGAGGCCAA  TAAGCAAGAA  ATCCTTCCTG  CAACATGTTG  AAGAGCTTTG   120
CACAAACAAC  AACCTAAAGT  TTCAAGAAGA  ATTTTCGGAA  TTACCAAAAT  TTCTTCAGGA   180
TCTTTCTTCA  ACTGATGCTG  ATCTGCCTTG  GAATAGAGCA  AAAAACCGCT  TCCCAAACAT   240
AAAACCATAT  AATAATAACA  GAGTAAAGCT  GATAGCTGAC  GCTAGTGTTC  CAGGTTCGGA   300
TTATATTAAT  GCCAGCTATA  TTTCTGGTTA  TTTATGTCCA  AATGAATTTA  TTGCTACTCA   360
AGGTCCACTA  CCAGGAACAG  TTGGAGATTT  TTGGAGAATG  GTGTGGGAAA  CCAGAGCAAA   420
AACATTAGTA  ATGCTAACAC  AGTGTTTTGA  AAAAGGACGG  ATCAGATGCC  ATCAGTATTG   480
GCCAGAGGAC  AACAAGCCAG  TTACTGTCTT  TGGAGATATA  GTGATTACAA  AGCTAATGGA   540
GGATGTTCAA  ATAGATTGGA  CTATCAGGGA  TCTGAAAATT  GAAAGGCATG  GGGATTGCAT   600
GACTGTTCGA  CAGTGTAACT  TTACTGCCTG  GCCAGAGCAT  GGGGTTCCTG  AGAACAGCGC   660
CCCTCTAATT  CACTTTGTGA  AGTTGGTTCG  AGCAAGCAGG  GCACATGACA  CCACACCTAT   720
GATTGTTCAC  TGCAGGCACA  GTATATCTTT  TTACACCAGT  GCATTCTGGA  TCTCTTATCA   780
AATAAGGGAA  GTAATCAGCC  CATCTGTTTT  GTTAACTATT  CAGCACTTCA  GAAGATGGAC   840
TCTTTGGACG  CCATGGAAGG  TGATGTTGAG  CTTGAATGGG  AAGAAACCAC  TATGTAAATA   900
TTCAGACCAA  AGGATACAAT  TGGAAGAGAT  TTTTAAATCC  CAGGGGCCAA  AGTTACCCCC   960
TCATTCTTCC  GAATTGAAAT  GTGCAACCTT  AAAGAAATAT  CTATGCTTCT  CTCACTGTGC  1020
CTTTCCAAAC  GGATTGAACA  TTTTAAGACT  AGTTCTTGAA  AATAGCTAAT  ACAGAATAAT  1080
TATTTGTTTT  GTACAGAATA  AATATTATGC  ATTTTAAATG  CTTAAGAAAA  GACATCCCAT  1140
ATGTTTTTGA  AGTCCTCCAT  ATTTGGAAT   AAGCCAAATA  GAAAATTATT  ATTATATTAG  1200
CATTAATGTT  TCAATGTGAA  TTTTCCCTAT  GTATTGGATT  TAATTTTGAG  GACAAAAGTT  1260
GTAAATGTTG  ATTCAGTAGT  GTTGTTTTGG  CTTACAGGGT  ATTGATGTTT  CTTGTGGATA  1320
ATTTCCAGGA  CTGTCATAAT  GATCTGTACT  TCCATGTACA  CCCCTGTGTT  TTGAATCCTC  1380
TGTTTTATGA  GTGCTGAGAT  ATCATCTCAT  GATCCCGAAC  AGCTGAACAG  TAACCCCCTG  1440
ACACTGCAGG  GATTACTTGG  CCTTTATACA  ACACACAGTA  GCTCTTCAGG  GACACTTAGG  1500
GCTATTTAAT  TTCGATTGTG  TCTTCAGTTT  GAGAACCTTA  AAAGAAAATT  AAAAGTGCAA  1560
TTGCACACAT  GAAATTACAG  AGTACCATTC  TAGCAAACCT  ACATTTGTAA  ACTTTAAAAC  1620
ACAAGTTTTN  CCCCCTGTAT  TGTATATTCA  AATATATAGT  AAATGTATCA  GAGTATTTGC  1680
CCATTAGATA  TGATCAACCT  AATATTAACA  ATTCTGAAGA  GTTTCTTCAG  CAAAAATGTA  1740
TCAAGAGTAA  TAAAAACACT  GTGCGTGTTT  CAAGCTTGTA  AACCAATGAT  CTGCTGCTGT  1800
```

```
GGTGCCAACA GAGACTTCCA AATGGATTAT GTTAAATGGC CGTCATTTCA TTTCCCAAGG    1860

TTGATTTTGA GCAGTATACT TGGTGGAACT GAAAACAAAG AAATTAACCA TCTATAGCAA    1920

ATTCAAGGTT TCTTTATAGA AAATCTTTCA GCCTCCATCT TATTAAATAG TGACAATGTG    1980

GTAAGTTTTG AATTATATGA ACTCATTTTG TCATAGATTT CAATTAAGAG TAATAAATAG    2040

TATTAATTAT GCTCTTCTAT GATAAGAAGT ATATCTTATG CTTATTCCG CTGGAACATA     2100

TATATATATG AAATGCTATG GCCAATAAAA TTGAATTTTA ATGAAAAAAA AAAAAAAAA     2160

AAAAAAAAAA AAA                                                       2173
```

( 2 ) INFORMATION FOR SEQ ID NO:7:

( i ) SEQUENCE CHARACTERISTICS:
        ( A ) LENGTH: 334 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:7:

```
Met Arg Met Arg Pro Ile Ser Lys Lys Ser Phe Leu Gln His Val Glu
 1               5                  10                  15

Glu Leu Cys Thr Asn Asn Asn Leu Lys Phe Gln Glu Glu Phe Ser Glu
                20                  25                  30

Leu Pro Lys Phe Leu Gln Asp Leu Ser Ser Thr Asp Ala Asp Leu Pro
            35                  40                  45

Trp Asn Arg Ala Lys Asn Arg Phe Pro Asn Ile Lys Pro Tyr Asn Asn
        50                  55                  60

Asn Arg Val Lys Leu Ile Ala Asp Ala Ser Val Pro Gly Ser Asp Tyr
 65                 70                  75                  80

Ile Asn Ala Ser Tyr Ile Ser Gly Tyr Leu Cys Pro Asn Glu Phe Ile
                85                  90                  95

Ala Thr Gln Gly Pro Leu Pro Gly Thr Val Gly Asp Phe Trp Arg Met
               100                 105                 110

Val Trp Glu Thr Arg Ala Lys Thr Leu Val Met Leu Thr Gln Cys Phe
           115                 120                 125

Glu Lys Gly Arg Ile Arg Cys His Gln Tyr Trp Pro Glu Asp Asn Lys
       130                 135                 140

Pro Val Thr Val Phe Gly Asp Ile Val Ile Thr Lys Leu Met Glu Asp
145                 150                 155                 160

Val Gln Ile Asp Trp Thr Ile Arg Asp Leu Lys Ile Glu Arg His Gly
               165                 170                 175

Asp Cys Met Thr Val Arg Gln Cys Asn Phe Thr Ala Trp Pro Glu His
           180                 185                 190

Gly Val Pro Glu Asn Ser Ala Pro Leu Ile His Phe Val Lys Leu Val
       195                 200                 205

Arg Ala Ser Arg Ala His Asp Thr Thr Pro Met Ile Val His Cys Arg
   210                 215                 220

His Ser Ile Ser Phe Tyr Thr Ser Ala Phe Trp Ile Ser Tyr Gln Ile
225                 230                 235                 240

Arg Glu Val Ile Ser Pro Ser Val Leu Leu Thr Ile Gln His Phe Arg
               245                 250                 255

Arg Trp Thr Leu Trp Thr Pro Trp Lys Val Met Leu Ser Leu Asn Gly
           260                 265                 270

Lys Lys Pro Leu Cys Lys Tyr Ser Asp Gln Arg Ile Gln Leu Glu Glu
       275                 280                 285
```

```
        Ile  Phe  Lys  Ser  Gln  Gly  Pro  Lys  Leu  Pro  Pro  His  Ser  Ser  Glu  Leu
             290                      295                      300

Lys  Cys  Ala  Thr  Leu  Lys  Lys  Tyr  Leu  Cys  Phe  Ser  His  Cys  Ala  Phe
        305                      310                      315                      320

Pro  Asn  Gly  Leu  Asn  Ile  Leu  Arg  Leu  Val  Leu  Glu  Asn  Ser
                            325                      330
```

( 2 ) INFORMATION FOR SEQ ID NO:8:

( i ) SEQUENCE CHARACTERISTICS:
        ( A ) LENGTH: 532 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:8:

```
ACAACAAGCC  AGTTACTGTC  TTTGGAGATA  TAGTGATTAC  AAAGCTAATG  GAGGATGTTC    60

AAATAGATTG  GACTATCAGG  GATCTGAAAA  TTGAAAGGCA  TGGGGATTGC  ATGACTGTTC   120

GACAGTGTAA  CTTTACTGCC  TGGCCAGAGC  ATGGGGTTCC  TGAGAACAGC  GCCCCTCTAA   180

TTCACTTTGT  GAAGTTGGTT  CGAGCAAGCA  GGGCACATGA  CACCACACCT  ATGATTGTTC   240

ACTGCAGTGC  TGGAGTTGGA  AGAACTGGAG  TTTTTATTGC  TCTGGACCAT  TAACACAAC    300

ATATAAATGA  CCATGATTTT  GTGGATATAT  ATGGACTAGT  AGCTGAACTG  AGAAGTGAAA   360

GAATGTGCAT  GGTGCAGAAT  CTGGCACAGT  ATATCTTTTT  ACACCAGTGC  ATTCTGGATC   420

TCTTATCAAA  TAAGGGAAGT  AATCAGCCCA  TCTGTTTTGT  TAACTATTCA  GCACTTCAGA   480

AGATGGACTC  TTTGGACGCC  ATGGAAGGTG  ATGTTGAGCT  TGAATGGGAA  GA           532
```

( 2 ) INFORMATION FOR SEQ ID NO:9:

( i ) SEQUENCE CHARACTERISTICS:
        ( A ) LENGTH: 176 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:9:

```
        Asn  Lys  Pro  Val  Thr  Val  Phe  Gly  Asp  Ile  Val  Ile  Thr  Lys  Leu  Met
        1              5                        10                       15

Glu  Asp  Val  Gln  Ile  Asp  Trp  Thr  Ile  Arg  Asp  Leu  Lys  Ile  Glu  Arg
                            20                       25                       30

His  Gly  Asp  Cys  Met  Thr  Val  Arg  Gln  Cys  Asn  Phe  Thr  Ala  Trp  Pro
                       35                       40                       45

Glu  His  Gly  Val  Pro  Glu  Asn  Ser  Ala  Pro  Leu  Ile  His  Phe  Val  Lys
             50                       55                       60

Leu  Val  Arg  Ala  Ser  Arg  Ala  His  Asp  Thr  Thr  Pro  Met  Ile  Val  His
        65                       70                       75                       80

Cys  Ser  Ala  Gly  Val  Gly  Arg  Thr  Gly  Val  Phe  Ile  Ala  Leu  Asp  His
                            85                       90                       95

Leu  Thr  Gln  His  Ile  Asn  Asp  His  Asp  Phe  Val  Asp  Ile  Tyr  Gly  Leu
                       100                      105                      110

Val  Ala  Glu  Leu  Arg  Ser  Glu  Arg  Met  Cys  Met  Val  Gln  Asn  Leu  Ala
                  115                      120                      125

Gln  Tyr  Ile  Phe  Leu  His  Gln  Cys  Ile  Leu  Asp  Leu  Leu  Ser  Asn  Lys
             130                      135                      140
```

|  |  |  |  |  |  |  |  |  |  |  |  |  |  |  |
|---|---|---|---|---|---|---|---|---|---|---|---|---|---|---|
| Gly | Ser | Asn | Gln | Pro | Ile | Cys | Phe | Val | Asn | Tyr | Ser | Ala | Leu | Gln | Lys |
| 145 | | | | 150 | | | | | 155 | | | | | 160 |
| Met | Asp | Ser | Leu | Asp | Ala | Met | Glu | Gly | Asp | Val | Glu | Leu | Glu | Trp | Glu |
| | | | | 165 | | | | | 170 | | | | | 175 |

( 2 ) INFORMATION FOR SEQ ID NO:10:

( i ) SEQUENCE CHARACTERISTICS:
        ( A ) LENGTH: 2309 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: misc_feature
        ( B ) LOCATION: 1766
        ( D ) OTHER INFORMATION: /note= "N=x=unknown nucleotide"

( x i ) SEQUENCE DESCRIPTION: SEQ ID NO:10:

```
TATTTTAGCT  TGGGAAGTAA  TACGGGGATA  TTTAAACTCC  TTGGGGTTTG  AAAACCATGT      60
CATTATGAGA  ATGAGGCCAA  TAAGCAAGAA  ATCCTTCCTG  CAACATGTTG  AAGAGCTTTG     120
CACAAACAAC  AACCTAAAGT  TTCAAGAAGA  ATTTTCGGAA  TTACCAAAAT  TTCTTCAGGA     180
TCTTTCTTCA  ACTGATGCTG  ATCTGCCTTG  GAATAGAGCA  AAAAACCGCT  TCCCAAACAT     240
AAAACCATAT  AATAATAACA  GAGTAAAGCT  GATAGCTGAC  GCTAGTGTTC  AGGTTCGGA      300
TTATATTAAT  GCCAGCTATA  TTTCTGGTTA  TTTATGTCCA  AATGAATTTA  TTGCTACTCA     360
AGGTCCACTA  CCAGGAACAG  TTGGAGATTT  TTGGAGAATG  GTGTGGGAAA  CCAGAGCAAA     420
AACATTAGTA  ATGCTAACAC  AGTGTTTTGA  AAAAGGACGG  ATCAGATGCC  ATCAGTATTG     480
GCCAGAGGAC  AACAAGCCAG  TTACTGTCTT  TGGAGATATA  GTGATTACAA  AGCTAATGGA     540
GGATGTTCAA  ATAGATTGGA  CTATCAGGGA  TCTGAAAATT  GAAAGGCATG  GGGATTGCAT     600
GACTGTTCGA  CAGTGTAACT  TTACTGCCTG  GCCAGAGCAT  GGGGTTCCTG  AGAACAGCGC     660
CCCTCTAATT  CACTTTGTGA  AGTTGGTTCG  AGCAAGCAGG  GCACATGACA  CCACACCTAT     720
GATTGTTCAC  TGCAGTGCTG  GAGTTGGAAG  AACTGGAGTT  TTTATTGCTC  TGGACCATTT     780
AACACAACAT  ATAAATGACC  ATGATTTTGT  GGATATATAT  GGACTAGTAG  CTGAACTGAG     840
AAGTGAAAGA  ATGTGCATGG  TGCAGAATCT  GGCACAGTAT  ATCTTTTTAC  ACCAGTGCAT     900
TCTGGATCTC  TTATCAAATA  AGGGAAGTAA  TCAGCCCATC  TGTTTTGTTA  ACTATTCAGC     960
ACTTCAGAAG  ATGGACTCTT  GGACGCCAT   GGAAGGTGAT  GTTGAGCTTG  AATGGGAAGA    1020
AACCACTATG  TAAATATTCA  GACCAAAGGA  TACAATTGGA  AGAGATTTTT  AAATCCCAGG    1080
GGCCAAAGTT  ACCCCCTCAT  TCTTCCGAAT  TGAAATGTGC  AACCTTAAAG  AAATATCTAT    1140
GCTTCTCTCA  CTGTGCCTTT  CCAAACGGAT  TGAACATTTT  AAGACTAGTT  CTTGAAAATA    1200
GCTAATACAG  AATAATTATT  TGTTTGTAC   AGAATAAATA  TTATGCATTT  TAAATGCTTA    1260
AGAAAAGACA  TCCCATATGT  TTTTGAAGTC  CTCCATATTT  TGGAATAAGC  CAAATAGAAA    1320
ATTATTATTA  TATTAGCATT  AATGTTTCAA  TGTGAATTTT  CCCTATGTAT  TGGATTTAAT    1380
TTTGAGGACA  AAAGTTGTAA  ATGTTGATTC  AGTAGTGTTG  TTTTGGCTTA  CAGGGTATTG    1440
ATGTTTCTTG  TGGATAATTT  CCAGGACTGT  CATAATGATC  TGTACTTCCA  TGTACACCCC    1500
TGTGTTTTGA  ATCCTCTGTT  TTATGAGTGC  TGAGATATCA  TCTCATGATC  CCGAACAGCT    1560
GAACAGTAAC  CCCCTGACAC  TGCAGGGATT  ACTTGGCCTT  TATACAACAC  ACAGTAGCTC    1620
TTCAGGGACA  CTTAGGGCTA  TTTAATTTCG  ATTGTGTCTT  CAGTTTGAGA  ACCTTAAAAG    1680
```

-continued

```
AAAATTAAAA GTGCAATTGC ACACATGAAA TTACAGAGTA CCATTCTAGC AAACCTACAT      1740

TTGTAAACTT TAAAACACAA GTTTTNCCCC CTGTATTGTA TATTCAAATA TATAGTAAAT      1800

GTATCAGAGT ATTTGCCCAT TAGATATGAT CAACCTAATA TTAACAATTC TGAAGAGTTT      1860

CTTCAGCAAA AATGTATCAA GAGTAATAAA AACACTGTGC GTGTTTCAAG CTTGTAAACC      1920

AATGATCTGC TGCTGTGGTG CCAACAGAGA CTTCCAAATG GATTATGTTA AATGGCCGTC      1980

ATTTCATTTC CCAAGGTTGA TTTTGAGCAG TATACTTGGT GGAACTGAAA ACAAAGAAAT      2040

TAACCATCTA TAGCAAATTC AAGGTTTCTT TATAGAAAAT CTTTCAGCCT CCATCTTATT      2100

AAATAGTGAC AATGTGGTAA GTTTTGAATT ATATGAACTC ATTTTGTCAT AGATTTCAAT      2160

TAAGAGTAAT AAATAGTATT AATTATGCTC TTCTATGATA AGAAGTATAT CTTATGCTTA      2220

TTTCCGCTGG AACATATATA TATATGAAAT GCTATGGCCA ATAAAATTGA ATTTTAATGA      2280

AAAAAAAAAA AAAAAAAAAA AAAAAAAA                                         2309
```

( 2 ) INFORMATION FOR SEQ ID NO:11:

( i ) SEQUENCE CHARACTERISTICS:
        ( A ) LENGTH: 322 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:11:

```
Met Arg Met Arg Pro Ile Ser Lys Lys Ser Phe Leu Gln His Val Glu
 1               5                  10                  15

Glu Leu Cys Thr Asn Asn Asn Leu Lys Phe Gln Glu Glu Phe Ser Glu
                20                  25                  30

Leu Pro Lys Phe Leu Gln Asp Leu Ser Ser Thr Asp Ala Asp Leu Pro
            35                  40                  45

Trp Asn Arg Ala Lys Asn Arg Phe Pro Asn Ile Lys Pro Tyr Asn Asn
        50                  55                  60

Asn Arg Val Lys Leu Ile Ala Asp Ala Ser Val Pro Gly Ser Asp Tyr
 65                 70                  75                  80

Ile Asn Ala Ser Tyr Ile Ser Gly Tyr Leu Cys Pro Asn Glu Phe Ile
                85                  90                  95

Ala Thr Gln Gly Pro Leu Pro Gly Thr Val Gly Asp Phe Trp Arg Met
            100                 105                 110

Val Trp Glu Thr Arg Ala Lys Thr Leu Val Met Leu Thr Gln Cys Phe
        115                 120                 125

Glu Lys Gly Arg Ile Arg Cys His Gln Tyr Trp Pro Glu Asp Asn Lys
    130                 135                 140

Pro Val Thr Val Phe Gly Asp Ile Val Ile Thr Lys Leu Met Glu Asp
145                 150                 155                 160

Val Gln Ile Asp Trp Thr Ile Arg Asp Leu Lys Ile Glu Arg His Gly
                165                 170                 175

Asp Cys Met Thr Val Arg Gln Cys Asn Phe Thr Ala Trp Pro Glu His
            180                 185                 190

Gly Val Pro Glu Asn Ser Ala Pro Leu Ile His Phe Val Lys Leu Val
        195                 200                 205

Arg Ala Ser Arg Ala His Asp Thr Thr Pro Met Ile Val His Cys Ser
    210                 215                 220

Ala Gly Val Gly Arg Thr Gly Val Phe Ile Ala Leu Asp His Leu Thr
225                 230                 235                 240
```

```
Gln His Ile Asn Asp His Asp Phe Val Asp Ile Tyr Gly Leu Val Ala
                245                 250                 255

Glu Leu Arg Ser Glu Arg Met Cys Met Val Gln Asn Leu Ala Gln Tyr
            260                 265                 270

Ile Phe Leu His Gln Cys Ile Leu Asp Leu Leu Ser Asn Lys Gly Ser
        275                 280                 285

Asn Gln Pro Ile Cys Phe Val Asn Tyr Ser Ala Leu Gln Lys Met Asp
    290                 295                 300

Ser Leu Asp Ala Met Glu Gly Asp Val Glu Leu Glu Trp Glu Glu Thr
305                 310                 315                 320

Thr Met
```

( 2 ) INFORMATION FOR SEQ ID NO:12:

( i ) SEQUENCE CHARACTERISTICS:
        ( A ) LENGTH: 292 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:12:

```
Met Asn Val Glu Pro Ile His Ala Asp Ile Leu Leu Glu Thr Tyr Lys
1               5                   10                  15

Arg Lys Ile Ala Asp Glu Gly Arg Leu Phe Leu Ala Glu Phe Gln Ser
            20                  25                  30

Ile Pro Arg Val Phe Ser Lys Phe Pro Ile Lys Glu Ala Arg Lys Pro
        35                  40                  45

Phe Asn Gln Asn Lys Asn Arg Tyr Val Asp Ile Leu Pro Tyr Asp Tyr
    50                  55                  60

Asn Arg Val Glu Leu Ser Glu Ile Asn Gly Asp Ala Gly Ser Asn Tyr
65                  70                  75                  80

Ile Asn Ala Ser Tyr Ile Asp Gly Phe Lys Glu Pro Arg Lys Tyr Ile
                85                  90                  95

Ala Ala Gln Gly Pro Arg Asp Glu Thr Val Asp Asp Phe Trp Arg Met
            100                 105                 110

Ile Trp Glu Gln Lys Ala Thr Val Ile Val Met Val Thr Arg Cys Glu
        115                 120                 125

Glu Gly Asn Arg Asn Lys Cys Ala Glu Tyr Trp Pro Ser Met Glu Glu
    130                 135                 140

Gly Thr Arg Ala Phe Gly Asp Val Val Lys Ile Asn Gln His Lys Lys
145                 150                 155                 160

Arg Cys Pro Asp Tyr Ile Ile Gln Lys Leu Asn Ile Val Asn Lys Lys
                165                 170                 175

Glu Lys Ala Thr Gly Arg Glu Val Thr His Ile Gln Phe Thr Ser Trp
            180                 185                 190

Pro Asp His Gly Val Pro Glu Asp Pro His Leu Leu Leu Lys Leu Arg
        195                 200                 205

Arg Arg Val Asn Ala Phe Ser Asn Phe Phe Ser Gly Pro Ile Val Val
    210                 215                 220

His Cys Ser Ala Gly Val Gly Arg Thr Gly Thr Tyr Ile Gly Ile Asp
225                 230                 235                 240

Ala Met Leu Glu Gly Leu Glu Ala Glu Asn Lys Val Asp Val Tyr Gly
                245                 250                 255

Tyr Val Val Lys Leu Arg Arg Gln Arg Cys Leu Met Val Gln Val Glu
```

|     |     |     |     | 260 |     |     |     |     | 265 |     |     |     |     | 270 |     |
| --- | --- | --- | --- | --- | --- | --- | --- | --- | --- | --- | --- | --- | --- | --- | --- |
| Ala | Gln | Tyr | Ile | Leu | Ile | His | Gln | Ala | Leu | Val | Glu | Tyr | Asn | Gln | Phe |
|     |     |     | 275 |     |     |     |     | 280 |     |     |     |     | 285 |     |     |
| Gly | Glu | Thr | Glu |
|     |     |     | 290 |

(2) INFORMATION FOR SEQ ID NO:13:

(i) SEQUENCE CHARACTERISTICS:
       (A) LENGTH: 289 amino acids
       (B) TYPE: amino acid
       (C) STRANDEDNESS: single
       (D) TOPOLOGY: unknown (ii) MOLECULE TYPE: protein (xi) SEQUENCE DESCRIPTION: SEQ ID NO:13:

| Met | Arg | Asp | His | Pro | Pro | Ile | Pro | Ile | Thr | Asp | Leu | Ala | Asp | Asn | Ile |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Glu | Arg | Leu | Lys | Ala | Asn | Asp | Gly | Leu | Lys | Phe | Ser | Gln | Glu | Tyr | Glu |
|     |     |     | 20  |     |     |     |     | 25  |     |     |     |     | 30  |     |     |
| Ser | Ile | Asp | Pro | Gly | Gln | Gln | Phe | Thr | Trp | Glu | Asn | Ser | Asn | Leu | Glu |
|     |     | 35  |     |     |     |     | 40  |     |     |     |     | 45  |     |     |     |
| Val | Asn | Lys | Pro | Lys | Asn | Arg | Tyr | Ala | Asn | Val | Ile | Ala | Tyr | Asp | His |
|     | 50  |     |     |     |     | 55  |     |     |     |     | 60  |     |     |     |     |
| Ser | Arg | Val | Ile | Leu | Thr | Ser | Ile | Asp | Gly | Val | Pro | Gly | Ser | Asp | Tyr |
| 65  |     |     |     |     | 70  |     |     |     |     | 75  |     |     |     |     | 80  |
| Ile | Asn | Ala | Asn | Tyr | Ile | Asp | Gly | Tyr | Arg | Lys | Gln | Asn | Ala | Tyr | Ile |
|     |     |     |     | 85  |     |     |     |     | 90  |     |     |     |     | 95  |     |
| Ala | Thr | Gln | Gly | Pro | Leu | Pro | Glu | Thr | Met | Gly | Asp | Phe | Trp | Arg | Met |
|     |     |     | 100 |     |     |     |     | 105 |     |     |     |     | 110 |     |     |
| Val | Trp | Glu | Gln | Arg | Thr | Ala | Thr | Val | Val | Met | Met | Thr | Arg | Leu | Glu |
|     |     |     | 115 |     |     |     |     | 120 |     |     |     |     | 125 |     |     |
| Glu | Lys | Ser | Arg | Val | Lys | Cys | Asp | Gln | Tyr | Trp | Pro | Ala | Arg | Gly | Thr |
|     | 130 |     |     |     |     | 135 |     |     |     |     | 140 |     |     |     |     |
| Glu | Thr | Cys | Gly | Leu | Ile | Gln | Val | Thr | Leu | Leu | Asp | Thr | Val | Glu | Leu |
| 145 |     |     |     |     | 150 |     |     |     |     | 155 |     |     |     |     | 160 |
| Ala | Thr | Tyr | Thr | Val | Arg | Thr | Phe | Ala | Leu | His | Lys | Ser | Gly | Ser | Ser |
|     |     |     |     | 165 |     |     |     |     | 170 |     |     |     |     | 175 |     |
| Glu | Lys | Arg | Glu | Leu | Arg | Gln | Phe | Gln | Phe | Met | Ala | Trp | Pro | Asp | His |
|     |     |     | 180 |     |     |     |     | 185 |     |     |     |     | 190 |     |     |
| Gly | Val | Pro | Glu | Tyr | Pro | Thr | Pro | Ile | Leu | Ala | Phe | Leu | Arg | Arg | Val |
|     |     |     | 195 |     |     |     |     | 200 |     |     |     |     | 205 |     |     |
| Lys | Ala | Cys | Asn | Pro | Leu | Asp | Ala | Gly | Pro | Met | Val | Val | His | Cys | Ser |
|     | 210 |     |     |     |     | 215 |     |     |     |     | 220 |     |     |     |     |
| Ala | Gly | Val | Gly | Arg | Thr | Gly | Cys | Phe | Ile | Val | Ile | Asp | Ala | Met | Leu |
| 225 |     |     |     |     | 230 |     |     |     |     | 235 |     |     |     |     | 240 |
| Glu | Arg | Met | Lys | His | Glu | Lys | Thr | Val | Asp | Ile | Tyr | Gly | His | Val | Thr |
|     |     |     |     | 245 |     |     |     |     | 250 |     |     |     |     | 255 |     |
| Cys | Met | Arg | Ser | Gln | Arg | Asn | Tyr | Met | Val | Gln | Thr | Glu | Asp | Gln | Tyr |
|     |     |     | 260 |     |     |     |     | 265 |     |     |     |     | 270 |     |     |
| Val | Phe | Ile | His | Glu | Ala | Leu | Leu | Glu | Ala | Ala | Thr | Cys | Gly | His | Thr |
|     |     |     | 275 |     |     |     |     | 280 |     |     |     |     | 285 |     |     |
| Glu |

(2) INFORMATION FOR SEQ ID NO:14:

( i ) SEQUENCE CHARACTERISTICS:
   ( A ) LENGTH: 2692 base pairs
   ( B ) TYPE: nucleic acid
   ( C ) STRANDEDNESS: double
   ( D ) TOPOLOGY: unknown ( i i ) MOLECULE TYPE: cDNA ( i x ) FEATURE:
   ( A ) NAME/KEY: misc_feature
   ( B ) LOCATION: 2149
   ( D ) OTHER INFORMATION: /note= "N=x=unknown nucleotide"

( x i ) SEQUENCE DESCRIPTION: SEQ ID NO:14:

| | | | | | | |
|---|---|---|---|---|---|---|
| GCCTTCGTCA | ACTAATTCTT | CTTAAATTTA | GAACTTCATC | CCAATAACTT | ATTAGAAAAA | 60 |
| AAAGAAAGTA | GAATAGGTTC | TATGGAATTA | AAACAAGAAA | AAGAAGTCGA | GTAGCTATAA | 120 |
| ATTTGCAACA | TATTCAGAGA | GGTGATTTTA | ACAAGGAAAT | TATTTGACTA | AATGTCTTTA | 180 |
| CTTAAAAAGA | AAACTAAACC | TAATTTTATA | TACTTTGTGT | GAAACTCCCT | TCTTGGACTT | 240 |
| TACTCCGCTT | GTTTTAGAAT | TCGACAGAAG | CAGAAAGAAG | GTGGCACATA | CTCTCCTCAG | 300 |
| GATGCAGAAA | TTATTGACAC | TAAATTGAAG | CTGGATCAGC | TCATCACAGT | GGCAGACCTG | 360 |
| GAACTGAAGG | ACGAGAGATT | AACGCGATAC | TCTTCATTTT | TCTTTAGACG | CAAGGAGATT | 420 |
| TTTGTCATCC | AGTTACTTAG | TTATAGAAAA | TCCATCAAGC | CAATAAGCAA | GAAATCCTTC | 480 |
| CTGCAACATG | TTGAAGAGCT | TTGCACAAAC | AACAACCTAA | AGTTTCAAGA | AGAATTTTCG | 540 |
| GAATTACCAA | AATTTCTTCA | GGATCTTTCT | TCAACTGATG | CTGATCTGCC | TTGGAATAGA | 600 |
| GCAAAAAACC | GCTTCCCAAA | CATAAAACCA | TATAATAATA | ACAGAGTAAA | GCTGATAGCT | 660 |
| GACGCTAGTG | TTCCAGGTTC | GGATTATATT | AATGCCAGCT | ATATTTCTGG | TTATTTATGT | 720 |
| CCAAATGAAT | TTATTGCTAC | TCAAGGTCCA | CTACCAGGAA | CAGTTGGAGA | TTTTTGGAGA | 780 |
| ATGGTGTGGG | AAACCAGAGC | AAAAACATTA | GTAATGCTAA | CACAGTGTTT | TGAAAAAGGA | 840 |
| CGGATCAGAT | GCCATCAGTA | TTGGCCAGAG | GACAACAAGC | CAGTTACTGT | CTTTGGAGAT | 900 |
| ATAGTGATTA | CAAAGCTAAT | GGAGGATGTT | CAAATAGATT | GGACTATCAG | GGATCTGAAA | 960 |
| ATTGAAAGGC | ATGGGGATTG | CATGACTGTT | CGACAGTGTA | ACTTTACTGC | CTGGCCAGAG | 1020 |
| CATGGGGTTC | CTGAGAACAG | CGCCCCTCTA | ATTCACTTTG | TGAAGTTGGT | TCGAGCAAGC | 1080 |
| AGGGCACATG | ACACCACACC | TATGATTGTT | CACTGCAGTG | CTGGAGTTGG | AAGAACTGGA | 1140 |
| GTTTTTATTG | CTCTGGACCA | TTTAACACAA | CATATAAATG | ACCATGATTT | TGTGGATATA | 1200 |
| TATGGACTAG | TAGCTGAACT | GAGAAGTGAA | AGAATGTGCA | TGGTGCAGAA | TCTGGCACAG | 1260 |
| TATATCTTTT | TACACCAGTG | CATTCTGGAT | CTCTTATCAA | ATAAGGGAAG | TAATCAGCCC | 1320 |
| ATCTGTTTTG | TTAACTATTC | AGCACTTCAG | AAGATGGACT | CTTTGGACGC | CATGGAAGGT | 1380 |
| GATGTTGAGC | TTGAATGGGA | AGAAACCACT | ATGTAAATAT | TCAGACCAAA | GGATACAATT | 1440 |
| GGAAGAGATT | TTTAAATCCC | AGGGGCCAAA | GTTACCCCCT | CATTCTTCCG | AATTGAAATG | 1500 |
| TGCAACCTTA | AAGAAATATC | TATGCTTCTC | TCACTGTGCC | TTTCCAAACG | GATTGAACAT | 1560 |
| TTTAAGACTA | GTTCTTGAAA | ATAGCTAATA | CAGAATAATT | ATTTGTTTTG | TACAGAATAA | 1620 |
| ATATTATGCA | TTTTAAATGC | TTAAGAAAAG | ACATCCCATA | TGTTTTGAA | GTCCTCCATA | 1680 |
| TTTTGGAATA | AGCCAAATAG | AAAATTATTA | TTATATTAGC | ATTAATGTTT | CAATGTGAAT | 1740 |
| TTTCCCTATG | TATTGGATTT | AATTTTGAGG | ACAAAGTTG | TAAATGTTGA | TTCAGTAGTG | 1800 |
| TTGTTTTGGC | TTACAGGGTA | TTGATGTTTC | TTGTGGATAA | TTTCCAGGAC | TGTCATAATG | 1860 |
| ATCTGTACTT | CCATGTACAC | CCCTGTGTTT | TGAATCCTCT | GTTTTATGAG | TGCTGAGATA | 1920 |
| TCATCTCATG | ATCCCGAACA | GCTGAACAGT | AACCCCCTGA | CACTGCAGGG | ATTACTTGGC | 1980 |

```
CTTTATACAA CACACAGTAG CTCTTCAGGG ACACTTAGGG CTATTTAATT TCGATTGTGT    2040

CTTCAGTTTG AGAACCTTAA AAGAAAATTA AAAGTGCAAT TGCACACATG AAATTACAGA    2100

GTACCATTCT AGCAAACCTA CATTTGTAAA CTTTAAAACA CAAGTTTTNC CCCCTGTATT    2160

GTATATTCAA ATATATAGTA AATGTATCAG AGTATTTGCC CATTAGATAT GATCAACCTA    2220

ATATTAACAA TTCTGAAGAG TTTCTTCAGC AAAAATGTAT CAAGAGTAAT AAAAACACTG    2280

TGCGTGTTTC AAGCTTGTAA ACCAATGATC TGCTGCTGTG GTGCCAACAG AGACTTCCAA    2340

ATGGATTATG TTAAATGGCC GTCATTTCAT TTCCCAAGGT TGATTTGAG CAGTATACTT     2400

GGTGGAACTG AAAACAAAGA AATTAACCAT CTATAGCAAA TTCAAGGTTT CTTTATAGAA    2460

AATCTTTCAG CCTCCATCTT ATTAAATAGT GACAATGTGG TAAGTTTTGA ATTATATGAA    2520

CTCATTTTGT CATAGATTTC AATTAAGAGT AATAAATAGT ATTAATTATG CTCTTCTATG    2580

ATAAGAAGTA TATCTTATGC TTATTTCCGC TGGAACATAT ATATATATGA AATGCTATGG    2640

CCAATAAAAT TGAATTTTAA TGAAAAAAAA AAAAAAAAAA AAAAAAAAAA AA            2692
```

(2) INFORMATION FOR SEQ ID NO:15:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:15:

```
Asn Lys Lys Lys Lys Ser Ser Ser Tyr Lys Phe Ala Thr Tyr Ser Glu
 1               5                  10                  15

Arg Ile Arg Gln Lys Gln Lys Glu Gly Gly Thr Tyr Ser Pro Gln Asp
                20                  25                  30

Ala Glu Ile Ile Asp Thr Lys Leu Lys Leu Asp Gln Leu Ile Thr Val
            35                  40                  45

Ala Asp Leu Glu Leu Lys Asp Glu Arg Leu Thr Arg Tyr Ser Ser Phe
        50                  55                  60

Phe Phe Arg Arg Lys Glu Ile Phe Val Ile Gln Leu Leu Ser Tyr Arg
65                  70                  75                  80

Lys Ser Ile Lys Pro Ile Ser Lys Lys Ser Phe Leu Gln His Val Glu
                85                  90                  95

Glu Leu Cys Thr Asn Asn Asn Leu Lys Phe Gln Glu Glu Phe Ser Glu
            100                 105                 110

Leu Pro Lys Phe Leu Gln Asp Leu Ser Ser Thr Asp Ala Asp Leu Pro
        115                 120                 125

Trp Asn Arg Ala Lys Asn Arg Phe Pro Asn Ile Lys Pro Tyr Asn Asn
130                 135                 140

Asn Arg Val Lys Leu Ile Ala Asp Ala Ser Val Pro Gly Ser Asp Tyr
145                 150                 155                 160

Ile Asn Ala Ser Tyr Ile Ser Gly Tyr Leu Cys Pro Asn Glu Phe Ile
                165                 170                 175

Ala Thr Gln Gly Pro Leu Pro Gly Thr Val Gly Asp Phe Trp Arg Met
            180                 185                 190

Val Trp Glu Thr Arg Ala Lys Thr Leu Val Met Leu Thr Gln Cys Phe
        195                 200                 205

Glu Lys Gly Arg Ile Arg Cys His Gln Tyr Trp Pro Glu Asp Asn Lys
210                 215                 220

Pro Val Thr Val Phe Gly Asp Ile Val Ile Thr Lys Leu Met Glu Asp
```

```
                 225                           230                          235                           240
Val  Gln  Ile  Asp  Trp  Thr  Ile  Arg  Asp  Leu  Lys  Ile  Glu  Arg  His  Gly
                         245                          250                         255

Asp  Cys  Met  Thr  Val  Arg  Gln  Cys  Asn  Phe  Thr  Ala  Trp  Pro  Glu  His
               260                           265                         270

Gly  Val  Pro  Glu  Asn  Ser  Ala  Pro  Leu  Ile  His  Phe  Val  Lys  Leu  Val
               275                          280                    285

Arg  Ala  Ser  Arg  Ala  His  Asp  Thr  Thr  Pro  Met  Ile  Val  His  Cys  Ser
          290                         295                   300

Ala  Gly  Val  Gly  Arg  Thr  Gly  Val  Phe  Ile  Ala  Leu  Asp  His  Leu  Thr
305                           310                         315                           320

Gln  His  Ile  Asn  Asp  His  Asp  Phe  Val  Asp  Ile  Tyr  Gly  Leu  Val  Ala
                    325                         330                           335

Glu  Leu  Arg  Ser  Glu  Arg  Met  Cys  Met  Val  Gln  Asn  Leu  Ala  Gln  Tyr
               340                         345                         350

Ile  Phe  Leu  His  Gln  Cys  Ile  Leu  Asp  Leu  Leu  Ser  Asn  Lys  Gly  Ser
               355                         360                    365

Asn  Gln  Pro  Ile  Cys  Phe  Val  Asn  Tyr  Ser  Ala  Leu  Gln  Lys  Met  Asp
     370                         375                         380

Ser  Leu  Asp  Ala  Met  Glu  Gly  Asp  Val  Glu  Leu  Glu  Trp  Glu  Glu  Thr
385                           390                         395                           400

Thr  Met ( 2 ) INFORMATION FOR SEQ ID NO:16:

( i ) SEQUENCE CHARACTERISTICS:
               ( A ) LENGTH: 48 amino acids
               ( B ) TYPE: amino acid
               ( C ) STRANDEDNESS: single
               ( D ) TOPOLOGY: unknown ( i i ) MOLECULE TYPE: protein ( x i ) SEQUENCE DESCRIPTION: SEQ ID NO:16:

Ile  Arg  Gln  Lys  Gln  Lys  Glu  Gly  Gly  Thr  Tyr  Ser  Pro  Gln  Asp  Ala
       1                    5                              10                          15

Glu  Ile  Ile  Asp  Thr  Lys  Leu  Lys  Leu  Asp  Gln  Leu  Ile  Thr  Val  Ala
                           20                         25                    30

Asp  Leu  Glu  Leu  Lys  Asp  Glu  Arg  Leu  Thr  Arg  Pro  Ile  Ser  Lys  Lys
                    35                         40                    45

( 2 ) INFORMATION FOR SEQ ID NO:17:

( i ) SEQUENCE CHARACTERISTICS:
               ( A ) LENGTH: 57 amino acids
               ( B ) TYPE: amino acid
               ( C ) STRANDEDNESS: single
               ( D ) TOPOLOGY: unknown ( i i ) MOLECULE TYPE: protein ( x i ) SEQUENCE DESCRIPTION: SEQ ID NO:17:

Ile  Arg  Gln  Lys  Gln  Lys  Glu  Gly  Gly  Thr  Tyr  Ser  Pro  Gln  Asp  Ala
       1                    5                              10                          15

Glu  Ile  Ile  Asp  Thr  Lys  Leu  Lys  Leu  Asp  Gln  Leu  Ile  Thr  Val  Ala
                           20                         25                    30

Asp  Leu  Glu  Leu  Lys  Asp  Glu  Arg  Leu  Thr  Arg  Leu  Leu  Ser  Tyr  Arg
                    35                         40                    45

Lys  Ser  Ile  Lys  Pro  Ile  Ser  Lys  Lys
             50                    55
```

(2) INFORMATION FOR SEQ ID NO:18:

(i) SEQUENCE CHARACTERISTICS:
        (A) LENGTH: 72 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:18:

```
Ile Arg Gln Lys Gln Lys Gln Gly Gly Thr Tyr Ser Pro Gln Asp Ala
 1               5                  10                  15
Glu Ile Ile Asp Thr Lys Leu Lys Leu Asp Gln Leu Ile Thr Val Ala
             20                  25                  30
Asp Leu Glu Leu Lys Asp Glu Arg Leu Thr Arg Tyr Ser Ser Phe Phe
         35                  40                  45
Phe Arg Arg Lys Glu Ile Phe Val Ile Gln Leu Leu Ser Tyr Arg Lys
     50                  55                  60
Ser Ile Lys Pro Ile Ser Lys Lys
 65                  70
```

(2) INFORMATION FOR SEQ ID NO:19:

(i) SEQUENCE CHARACTERISTICS:
        (A) LENGTH: 85 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:19:

```
Lys Ser Ser Ser Tyr Lys Phe Ala Thr Tyr Ser Glu Arg Ile Arg Gln
 1               5                  10                  15
Lys Gln Lys Glu Gly Gly Thr Tyr Ser Pro Gln Asp Ala Glu Ile Ile
             20                  25                  30
Asp Thr Lys Leu Lys Leu Asp Gln Leu Ile Thr Val Ala Asp Leu Glu
         35                  40                  45
Leu Lys Asp Glu Arg Leu Thr Arg Tyr Ser Ser Phe Phe Arg Arg
     50                  55                  60
Lys Glu Ile Phe Val Ile Gln Leu Leu Ser Tyr Arg Lys Ser Ile Lys
 65                  70                  75                  80
Pro Ile Ser Lys Lys
             85
```

(2) INFORMATION FOR SEQ ID NO:20:

(i) SEQUENCE CHARACTERISTICS:
        (A) LENGTH: 78 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:20:

```
Glu Lys Gln Val Thr Thr Ile Arg Gln Lys Gln Lys Glu Gly Gly Thr
 1               5                  10                  15
Tyr Ser Pro Gln Asp Ala Glu Ile Ile Asp Thr Lys Leu Lys Leu Asp
             20                  25                  30
Gln Leu Ile Thr Val Ala Asp Leu Glu Leu Lys Asp Glu Arg Leu Thr
```

```
                3 5                        4 0                            4 5
        Arg  Tyr  Ser  Ser  Phe  Phe  Phe  Arg  Arg  Lys  Glu  Ile  Phe  Val  Ile  Gln
             5 0                        5 5                        6 0

Leu  Leu  Ser  Tyr  Arg  Lys  Ser  Ile  Lys  Pro  Ile  Ser  Lys  Lys
        6 5                        7 0                        7 5
```

( 2 ) INFORMATION FOR SEQ ID NO:21:

( i ) SEQUENCE CHARACTERISTICS:
        ( A ) LENGTH: 3973 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: misc_feature
        ( B ) LOCATION: 3430
        ( D ) OTHER INFORMATION: /note= "N=x=unknown nucleotide"

( x i ) SEQUENCE DESCRIPTION: SEQ ID NO:21:

```
GGAAGGTCTG  GGAGCCAGTA  CCCTGTGGAT  ACAAAGTTC   CCAGTGTTCC  CACAAATATT      60
GCTTTTTCTG  ATGTTCAGTC  AACTAGTGCA  ACATTGACAT  GGATAAGACC  TGACACTATC     120
CTTGGCTACT  TTCAAAATTA  CAAAATTACC  ACTCAACTTC  GTGCTCAAAA  ATGCAAAGAA     180
TGGGAATCCG  AAGAATGTGT  TGAATATCAA  AAAATTCAAT  ACCTCTATGA  AGCTCACTTA     240
ACTGAAGAGA  CAGTATATGG  ATTAAAGAAA  TTTAGATGGT  ATAGATTCCA  AGTGGCTGCC     300
AGCACCAATG  CTGGCTATGG  CAATGCTTCA  AACTGGATTT  CTACAAAAAC  TCTGCCTGGC     360
CCTCCAGATG  GTCCTCCTGA  AAATGTTCAT  GTAGTAGCAA  CATCACCTTT  TAGCATCAGC     420
ATAAGCTGGA  GTGAACCTGC  TGTCATTACT  GGACCAACAT  GTTATCTGAT  TGATGTCAAA     480
TCGGTAGATA  ATGATGAATT  TAATATATCC  TTCATCAAGT  CAAATGAAGA  AAATAAAACC     540
ATAGAAATTA  AGATTTAGA   AATATTCACA  AGGTATTCTG  TAGTGATCAC  TGCATTTACT     600
GGGAACATTA  GTGCTGCATA  TGTAGAAGGG  AAGTCAAGTG  CTGAAATGAT  TGTTACTACT     660
TTAGAATCAG  CCCCAAAGGA  CCCACCTAAC  AACATGACAT  TCAGAAGAT   ACCAGATGAA     720
GTTACAAAAT  TTCAATTAAC  GTTCCTTCCT  CCTTCTCAAC  CTAATGGAAA  TATCCAAGTA     780
TATCAAGCTC  TGGTTTACCG  AGAAGATGAT  CCTACTGCTG  TCCAGATTCA  CAACCTCAGT     840
ATTATACAGA  AAACCAACAC  ATTCGTCATT  GCAATGCTAG  AAGGACTAAA  AGGTGGACAT     900
ACATACAATA  TCAGTGTTTA  CGCAGTCAAT  AGTGCTGGTG  CAGGTCCAAA  GGTTCGATG     960
AGAATAACCA  TGGATATCAA  AGCTCCAGCA  CGACCAAAAA  CCAAACCAAC  CCCTATTTAT    1020
GATGCCACAG  GAAAACTGCT  TGTGACTTCA  ACAACAATTA  CAATCAGAAT  GCCAATATGT    1080
TACTACAGTG  ATGATCATGG  ACCAATAAAA  AATGTACAAG  TGCTTGTGAC  AGAAACAGGA    1140
GCTCAGCATG  ATGGAAATGT  AACAAAGTGG  TATGATGCAT  ATTTTAATAA  AGCAAGGCCA    1200
TATTTTACAA  ATGAAGGCTT  TCCTAACCCT  CCATGTACAG  AAGGAAAGAC  AAAGTTTAGT    1260
GGCAATGAAG  AAATCTACAT  CATAGGTGCT  GATAATGCAT  GCATGATTCC  TGGCAATGAA    1320
GACAAAATTT  GCAATGGACC  ACTGAAACCA  AAAAAGCAAT  ACTTATTTAA  ATTTAGAGCT    1380
ACAAATATTA  TGGGACAATT  TACTGACTCT  GATTATTCTG  ACCCTGTTAA  GACTTTAGGG    1440
GAAGGACTTT  CAGAAAGAAC  CGTAGAGATC  ATTCTTTCCG  TCACTTTGTG  TATCCTTTCA    1500
ATAATTCTCC  TTGGAACAGC  TATTTTTGCA  TTTGCAAGAA  TTCGACAGAA  GCAGAAAGAA    1560
GGTGGCACAT  ACTCTCCTCA  GGATGCAGAA  ATTATTGACA  CTAAATTGAA  GCTGGATCAG    1620
```

| | | | | | |
|---|---|---|---|---|---|
| CTCATCACAG | TGGCAGACCT | GGAACTGAAG | GACGAGAGAT | TAACGCGATA | CTCTTCATTT | 1680 |
| TTCTTTAGAC | GCAAGGAGAT | TTTTGTCATC | CAGTTACTTA | GTTATAGAAA | ATCCATCAAG | 1740 |
| CCAATAAGCA | AGAAATCCTT | CCTGCAACAT | GTTGAAGAGC | TTTGCACAAA | CAACAACCTA | 1800 |
| AAGTTTCAAG | AAGAATTTTC | GGAATTACCA | AAATTTCTTC | AGGATCTTTC | TTCAACTGAT | 1860 |
| GCTGATCTGC | CTTGGAATAG | AGCAAAAAAC | CGCTTCCCAA | ACATAAAACC | ATATAATAAT | 1920 |
| AACAGAGTAA | AGCTGATAGC | TGACGCTAGT | GTTCCAGGTT | CGGATTATAT | TAATGCCAGC | 1980 |
| TATATTTCTG | GTTATTTATG | TCCAAATGAA | TTTATTGCTA | CTCAAGGTCC | ACTACCAGGA | 2040 |
| ACAGTTGGAG | ATTTTTGGAG | AATGGTGTGG | GAAACCAGAG | CAAAACATT | AGTAATGCTA | 2100 |
| ACACAGTGTT | TTGAAAAAGG | ACGGATCAGA | TGCCATCAGT | ATTGGCCAGA | GGACAACAAG | 2160 |
| CCAGTTACTG | TCTTTGGAGA | TATAGTGATT | ACAAAGCTAA | TGGAGGATGT | TCAAATAGAT | 2220 |
| TGGACTATCA | GGGATCTGAA | AATTGAAAGG | CATGGGGATT | GCATGACTGT | TCGACAGTGT | 2280 |
| AACTTTACTG | CCTGGCCAGA | GCATGGGGTT | CCTGAGAACA | GCGCCCCTCT | AATTCACTTT | 2340 |
| GTGAAGTTGG | TTCGAGCAAG | CAGGGCACAT | GACACCACAC | CTATGATTGT | TCACTGCAGT | 2400 |
| GCTGGAGTTG | AAGAACTGG | AGTTTTTATT | GCTCTGGACC | ATTTAACACA | ACATATAAAT | 2460 |
| GACCATGATT | TTGTGGATAT | ATATGGACTA | GTAGCTGAAC | TGAGAAGTGA | AAGAATGTGC | 2520 |
| ATGGTGCAGA | ATCTGGCACA | GTATATCTTT | TTACACCAGT | GCATTCTGGA | TCTCTTATCA | 2580 |
| AATAAGGGAA | GTAATCAGCC | CATCTGTTTT | GTTAACTATT | CAGCACTTCA | GAAGATGGAC | 2640 |
| TCTTTGGACG | CCATGGAAGG | TGATGTTGAG | CTTGAATGGG | AAGAAACCAC | TATGTAAATA | 2700 |
| TTCAGACCAA | AGGATACAAT | TGGAAGAGAT | TTTTAAATCC | CAGGGGCCAA | AGTTACCCCC | 2760 |
| TCATTCTTCC | GAATTGAAAT | GTGCAACCTT | AAAGAAATAT | CTATGCTTCT | CTCACTGTGC | 2820 |
| CTTTCCAAAC | GGATTGAACA | TTTTAAGACT | AGTTCTTGAA | AATAGCTAAT | ACAGAATAAT | 2880 |
| TATTTGTTTT | GTACAGAATA | AATATTATGC | ATTTTAAATG | CTTAAGAAAA | GACATCCCAT | 2940 |
| ATGTTTTGA | AGTCCTCCAT | ATTTTGGAAT | AAGCCAAATA | GAAAATTATT | ATTATATTAG | 3000 |
| CATTAATGTT | TCAATGTGAA | TTTTCCCTAT | GTATTGGATT | TAATTTTGAG | GACAAAAGTT | 3060 |
| GTAAATGTTG | ATTCAGTAGT | GTTGTTTTGG | CTTACAGGGT | ATTGATGTTT | CTTGTGGATA | 3120 |
| ATTTCCAGGA | CTGTCATAAT | GATCTGTACT | TCCATGTACA | CCCCTGTGTT | TTGAATCCTC | 3180 |
| TGTTTTATGA | GTGCTGAGAT | ATCATCTCAT | GATCCCGAAC | AGCTGAACAG | TAACCCCCTG | 3240 |
| ACACTGCAGG | GATTACTTGG | CCTTTATACA | ACACACAGTA | GCTCTTCAGG | GACACTTAGG | 3300 |
| GCTATTTAAT | TTCGATTGTG | TCTTCAGTTT | GAGAACCTTA | AAGAAAATT | AAAAGTGCAA | 3360 |
| TTGCACACAT | GAAATTACAG | AGTACCATTC | TAGCAAACCT | ACATTTGTAA | ACTTTAAAAC | 3420 |
| ACAAGTTTTN | CCCCCTGTAT | TGTATATTCA | AATATATAGT | AAATGTATCA | GAGTATTTGC | 3480 |
| CCATTAGATA | TGATCAACCT | AATATTAACA | ATTCTGAAGA | GTTTCTTCAG | CAAAAATGTA | 3540 |
| TCAAGAGTAA | TAAAAACACT | GTGCGTGTTT | CAAGCTTGTA | AACCAATGAT | CTGCTGCTGT | 3600 |
| GGTGCCAACA | GAGACTTCCA | AATGGATTAT | GTTAAATGGC | CGTCATTTCA | TTTCCCAAGG | 3660 |
| TTGATTTTGA | GCAGTATACT | TGGTGGAACT | GAAAACAAAG | AAATTAACCA | TCTATAGCAA | 3720 |
| ATTCAAGGTT | TCTTTATAGA | AAATCTTTCA | GCCTCCATCT | TATTAAATAG | TGACAATGTG | 3780 |
| GTAAGTTTTG | AATTATATGA | ACTCATTTTG | TCATAGATTT | CAATTAAGAG | TAATAAATAG | 3840 |
| TATTAATTAT | GCTCTTCTAT | GATAAGAAGT | ATATCTTATG | CTTATTTCCG | CTGGAACATA | 3900 |
| TATATATATG | AAATGCTATG | GCCAATAAAA | TTGAATTTTA | ATGAAAAAAA | AAAAAAAAA | 3960 |
| AAAAAAAAAA | AAA | | | | | 3973 |

( 2 ) INFORMATION FOR SEQ ID NO:22:

( i ) SEQUENCE CHARACTERISTICS:
        ( A ) LENGTH: 898 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:22:

```
Gly Arg Ser Gly Ser Gln Tyr Pro Val Asp Thr Lys Val Pro Ser Val
 1               5                  10                  15

Pro Thr Asn Ile Ala Phe Ser Asp Val Gln Ser Thr Ser Ala Thr Leu
                20                  25                  30

Thr Trp Ile Arg Pro Asp Thr Ile Leu Gly Tyr Phe Gln Asn Tyr Lys
            35                  40                  45

Ile Thr Thr Gln Leu Arg Ala Gln Lys Cys Lys Glu Trp Glu Ser Glu
        50                  55                  60

Glu Cys Val Glu Tyr Gln Lys Ile Gln Tyr Leu Tyr Glu Ala His Leu
65                  70                  75                  80

Thr Glu Glu Thr Val Tyr Gly Leu Lys Lys Phe Arg Trp Tyr Arg Phe
                85                  90                  95

Gln Val Ala Ala Ser Thr Asn Ala Gly Tyr Gly Asn Ala Ser Asn Trp
                100                 105                 110

Ile Ser Thr Lys Thr Leu Pro Gly Pro Pro Asp Gly Pro Pro Glu Asn
            115                 120                 125

Val His Val Val Ala Thr Ser Pro Phe Ser Ile Ser Ile Ser Trp Ser
        130                 135                 140

Glu Pro Ala Val Ile Thr Gly Pro Thr Cys Tyr Leu Ile Asp Val Lys
145                 150                 155                 160

Ser Val Asp Asn Asp Glu Phe Asn Ile Ser Phe Ile Lys Ser Asn Glu
                165                 170                 175

Glu Asn Lys Thr Ile Glu Ile Lys Asp Leu Glu Ile Phe Thr Arg Tyr
                180                 185                 190

Ser Val Val Ile Thr Ala Phe Thr Gly Asn Ile Ser Ala Ala Tyr Val
            195                 200                 205

Glu Gly Lys Ser Ser Ala Glu Met Ile Val Thr Thr Leu Glu Ser Ala
        210                 215                 220

Pro Lys Asp Pro Pro Asn Asn Met Thr Phe Gln Lys Ile Pro Asp Glu
225                 230                 235                 240

Val Thr Lys Phe Gln Leu Thr Phe Leu Pro Pro Ser Gln Pro Asn Gly
                245                 250                 255

Asn Ile Gln Val Tyr Gln Ala Leu Val Tyr Arg Glu Asp Asp Pro Thr
                260                 265                 270

Ala Val Gln Ile His Asn Leu Ser Ile Ile Gln Lys Thr Asn Thr Phe
            275                 280                 285

Val Ile Ala Met Leu Glu Gly Leu Lys Gly Gly His Thr Tyr Asn Ile
        290                 295                 300

Ser Val Tyr Ala Val Asn Ser Ala Gly Ala Gly Pro Lys Val Pro Met
305                 310                 315                 320

Arg Ile Thr Met Asp Ile Lys Ala Pro Ala Arg Pro Lys Thr Lys Pro
                325                 330                 335

Thr Pro Ile Tyr Asp Ala Thr Gly Lys Leu Leu Val Thr Ser Thr Thr
                340                 345                 350

Ile Thr Ile Arg Met Pro Ile Cys Tyr Tyr Ser Asp Asp His Gly Pro
```

```
                    355                           360                            365
Ile  Lys  Asn  Val  Gln  Val  Leu  Val  Thr  Glu  Thr  Gly  Ala  Gln  His  Asp
     370                 375                           380
Gly  Asn  Val  Thr  Lys  Trp  Tyr  Asp  Ala  Tyr  Phe  Asn  Lys  Ala  Arg  Pro
385                      390                      395                      400
Tyr  Phe  Thr  Asn  Glu  Gly  Phe  Pro  Asn  Pro  Pro  Cys  Thr  Glu  Gly  Lys
                    405                 410                           415
Thr  Lys  Phe  Ser  Gly  Asn  Glu  Glu  Ile  Tyr  Ile  Ile  Gly  Ala  Asp  Asn
               420                      425                      430
Ala  Cys  Met  Ile  Pro  Gly  Asn  Glu  Asp  Lys  Ile  Cys  Asn  Gly  Pro  Leu
          435                      440                      445
Lys  Pro  Lys  Lys  Gln  Tyr  Leu  Phe  Lys  Phe  Arg  Ala  Thr  Asn  Ile  Met
     450                      455                      460
Gly  Gln  Phe  Thr  Asp  Ser  Asp  Tyr  Ser  Asp  Pro  Val  Lys  Thr  Leu  Gly
465                      470                      475                      480
Glu  Gly  Leu  Ser  Glu  Arg  Thr  Val  Glu  Ile  Ile  Leu  Ser  Val  Thr  Leu
               485                      490                      495
Cys  Ile  Leu  Ser  Ile  Ile  Leu  Leu  Gly  Thr  Ala  Ile  Phe  Ala  Phe  Ala
               500                      505                      510
Arg  Ile  Arg  Gln  Lys  Gln  Lys  Glu  Gly  Gly  Thr  Tyr  Ser  Pro  Gln  Asp
          515                      520                      525
Ala  Glu  Ile  Ile  Asp  Thr  Lys  Leu  Lys  Leu  Asp  Gln  Leu  Ile  Thr  Val
     530                      535                      540
Ala  Asp  Leu  Glu  Leu  Lys  Asp  Glu  Arg  Leu  Thr  Arg  Tyr  Ser  Ser  Phe
545                      550                      555                      560
Phe  Phe  Arg  Arg  Lys  Glu  Ile  Phe  Val  Ile  Gln  Leu  Leu  Ser  Tyr  Arg
                    565                      570                      575
Lys  Ser  Ile  Lys  Pro  Ile  Ser  Lys  Lys  Ser  Phe  Leu  Gln  His  Val  Glu
               580                      585                      590
Glu  Leu  Cys  Thr  Asn  Asn  Asn  Leu  Lys  Phe  Gln  Glu  Glu  Phe  Ser  Glu
          595                      600                      605
Leu  Pro  Lys  Phe  Leu  Gln  Asp  Leu  Ser  Ser  Thr  Asp  Ala  Asp  Leu  Pro
     610                      615                      620
Trp  Asn  Arg  Ala  Lys  Asn  Arg  Phe  Pro  Asn  Ile  Lys  Pro  Tyr  Asn  Asn
625                      630                      635                      640
Asn  Arg  Val  Lys  Leu  Ile  Ala  Asp  Ala  Ser  Val  Pro  Gly  Ser  Asp  Tyr
                    645                      650                      655
Ile  Asn  Ala  Ser  Tyr  Ile  Ser  Gly  Tyr  Leu  Cys  Pro  Asn  Glu  Phe  Ile
               660                      665                      670
Ala  Thr  Gln  Gly  Pro  Leu  Pro  Gly  Thr  Val  Gly  Asp  Phe  Trp  Arg  Met
          675                      680                      685
Val  Trp  Glu  Thr  Arg  Ala  Lys  Thr  Leu  Val  Met  Leu  Thr  Gln  Cys  Phe
     690                      695                      700
Glu  Lys  Gly  Arg  Ile  Arg  Cys  His  Gln  Tyr  Trp  Pro  Glu  Asp  Asn  Lys
705                      710                      715                      720
Pro  Val  Thr  Val  Phe  Gly  Asp  Ile  Val  Ile  Thr  Lys  Leu  Met  Glu  Asp
                    725                      730                      735
Val  Gln  Ile  Asp  Trp  Thr  Ile  Arg  Asp  Leu  Lys  Ile  Glu  Arg  His  Gly
               740                      745                      750
Asp  Cys  Met  Thr  Val  Arg  Gln  Cys  Asn  Phe  Thr  Ala  Trp  Pro  Glu  His
          755                      760                      765
Gly  Val  Pro  Glu  Asn  Ser  Ala  Pro  Leu  Ile  His  Phe  Val  Lys  Leu  Val
     770                      775                      780
```

```
Arg  Ala  Ser  Arg  Ala  His  Asp  Thr  Thr  Pro  Met  Ile  Val  His  Cys  Ser
785                 790                      795                           800

Ala  Gly  Val  Gly  Arg  Thr  Gly  Val  Phe  Ile  Ala  Leu  Asp  His  Leu  Thr
                    805                      810                      815

Gln  His  Ile  Asn  Asp  His  Asp  Phe  Val  Asp  Ile  Tyr  Gly  Leu  Val  Ala
               820                      825                      830

Glu  Leu  Arg  Ser  Glu  Arg  Met  Cys  Met  Val  Gln  Asn  Leu  Ala  Gln  Tyr
          835                      840                      845

Ile  Phe  Leu  His  Gln  Cys  Ile  Leu  Asp  Leu  Leu  Ser  Asn  Lys  Gly  Ser
          850                 855                      860

Asn  Gln  Pro  Ile  Cys  Phe  Val  Asn  Tyr  Ser  Ala  Leu  Gln  Lys  Met  Asp
865                      870                      875                      880

Ser  Leu  Asp  Ala  Met  Glu  Gly  Asp  Val  Glu  Leu  Glu  Trp  Glu  Glu  Thr
               885                      890                      895

Thr  Met
```

( 2 ) INFORMATION FOR SEQ ID NO:23:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:23:

```
Gln  Lys  Gln  Glu  Trp  Ile  Cys  Leu  Glu  Thr  Leu  Thr  Pro  Asp  Thr  Gln
1                   5                        10                       15

Tyr  Glu  Phe  Gln  Val  Arg  Val  Lys  Pro  Leu  Gln  Gly  Glu  Phe  Thr  Thr
               20                       25                       30

Trp  Ser  Pro  Trp  Ser  Gln  Pro  Leu  Ala
               35                  40
```

( 2 ) INFORMATION FOR SEQ ID NO:24:

( i ) SEQUENCE CHARACTERISTICS:
        ( A ) LENGTH: 92 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:24:

```
Leu  Ser  Pro  Pro  Thr  Asn  Leu  His  Leu  Glu  Ala  Asn  Pro  Asp  Thr  Gly
1                   5                        10                       15

Val  Leu  Thr  Val  Ser  Trp  Glu  Arg  Ser  Thr  Thr  Pro  Asp  Ile  Thr  Gly
               20                       25                       30

Tyr  Arg  Ile  Thr  Thr  Thr  Pro  Thr  Asn  Gly  Gln  Gln  Gly  Asn  Ser  Leu
          35                       40                       45

Glu  Glu  Val  Val  His  Ala  Asp  Gln  Ser  Ser  Cys  Thr  Phe  Asp  Asn  Leu
     50                       55                       60

Ser  Pro  Gly  Leu  Glu  Tyr  Asn  Val  Ser  Val  Tyr  Thr  Val  Lys  Asp  Asp
65                       70                       75                       80

Lys  Glu  Ser  Val  Pro  Ile  Ser  Asp  Thr  Ile  Ile  Pro
                    85                       90
```

( 2 ) INFORMATION FOR SEQ ID NO:25:

( i ) SEQUENCE CHARACTERISTICS:

(A) LENGTH: 98 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:25:

Met Arg Gly Leu Lys Pro Trp Thr Gln Tyr Ala Ile Phe Val Lys Thr
1               5                   10                  15

Leu Val Thr Phe Ser Asp Glu Arg Arg Thr Tyr Gly Ala Lys Ser Asp
            20                  25                  30

Ile Ile Tyr Val Gln Thr Asp Ala Thr Asn Pro Ser Val Pro Leu Asp
        35                  40                  45

Pro Ile Ser Val Ser Asn Ser Ser Gln Ile Ile Leu Lys Trp Lys
    50                  55                  60

Pro Pro Ser Asp Pro Asn Gly Asn Ile Thr His Tyr Leu Val Phe Trp
65                  70                  75                  80

Glu Arg Gln Ala Glu Asp Ser Glu Leu Phe Glu Leu Asp Tyr Cys Leu
                85                  90                  95

Lys Gly (2) INFORMATION FOR SEQ ID NO:26:

(i) SEQUENCE CHARACTERISTICS:
        (A) LENGTH: 99 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:26:

Leu His Gly Leu Lys Pro Trp Thr Gln Tyr Ala Val Tyr Val Lys Ala
1               5                   10                  15

Val Thr Leu Thr Met Val Glu Asn Asp His Ile Arg Gly Ala Lys Ser
            20                  25                  30

Glu Ile Leu Tyr Ile Arg Thr Asn Ala Ser Val Pro Ser Ile Pro Leu
        35                  40                  45

Asp Val Leu Ser Ala Ser Asn Ser Ser Ser Gln Leu Ile Val Lys Trp
    50                  55                  60

Asn Pro Pro Ser Leu Pro Asn Gly Asn Leu Ser Tyr Tyr Ile Val Arg
65                  70                  75                  80

Trp Gln Arg Gln Pro Gln Asp Gly Tyr Leu Tyr Arg His Asn Tyr Cys
                85                  90                  95

Ser Lys Asp (2) INFORMATION FOR SEQ ID NO:27:

(i) SEQUENCE CHARACTERISTICS:
        (A) LENGTH: 99 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:27:

Leu Ala Ser Leu Lys Pro Trp Thr Gln Tyr Ala Val Phe Val Arg Ala
1               5                   10                  15

Ile Thr Leu Thr Thr Glu Glu Asp Ser Pro His Gln Gly Ala Gln Ser
            20                  25                  30

```
            Pro  Ile  Val  Tyr  Leu  Arg  Thr  Leu  Pro  Ala  Ala  Pro  Thr  Val  Pro  Gln
                      35                      40                     45

Asp  Val  Ile  Ser  Thr  Ser  Asn  Ser  Ser  Ser  His  Leu  Leu  Val  Arg  Trp
                 50                       55                      60

Lys  Pro  Pro  Thr  Gln  Arg  Asn  Gly  Asn  Leu  Thr  Tyr  Tyr  Leu  Val  Leu
            65                      70                      75                          80

Trp  Gln  Arg  Leu  Ala  Glu  Asp  Gly  Asp  Leu  Tyr  Leu  Asn  Asp  Tyr  Cys
                                85                       90                      95

His  Arg  Gly
```

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

AYTTYTGGVR RATGRTNTGG                                  20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

CCNAYDCCHG CRCTRCAGTG                                  20

( 2 ) INFORMATION FOR SEQ ID NO:30:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:30:

```
            Arg  Cys  Xaa  Xaa  Tyr  Trp  Pro
            1                   5
```

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:31:

CCATCAGTAT TGGCCAGAGG                                  20

( 2 ) INFORMATION FOR SEQ ID NO:32:

( i ) SEQUENCE CHARACTERISTICS:

(A) LENGTH: 10 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:32:

```
His Cys Ser Xaa Gly Xaa Gly Arg Xaa Gly
1               5                   10
```

(2) INFORMATION FOR SEQ ID NO:33:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:33:

GACGGATCCG ATGCCATCAG TATTGG    26

(2) INFORMATION FOR SEQ ID NO:34:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:34:

TGGTCTAGAT ATTTACATAG TGGTT    25

(2) INFORMATION FOR SEQ ID NO:35:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:35:

CCATCAGTAT TGGCCAGAGG    20

(2) INFORMATION FOR SEQ ID NO:36:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:36:

CAAGCTCAAC ATCACCTTCC A    21

(2) INFORMATION FOR SEQ ID NO:37:

(i) SEQUENCE CHARACTERISTICS:
(A) LENGTH: 32 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:37:

CGGGATCCAT CATGAGAATG AGGCCAATAA GC　　　　　　　　　　　　　　32

( 2 ) INFORMATION FOR SEQ ID NO:38:

( i ) SEQUENCE CHARACTERISTICS:
　　　　( A ) LENGTH: 30 base pairs
　　　　( B ) TYPE: nucleic acid
　　　　( C ) STRANDEDNESS: single
　　　　( D ) TOPOLOGY: linear ( i i ) MOLECULE TYPE: DNA ( x i ) SEQUENCE DESCRIPTION: SEQ ID NO:38:

GCTCTAGAGC TTGTAATCAC TATATCTCCA　　　　　　　　　　　　　　　　30

( 2 ) INFORMATION FOR SEQ ID NO:39:

( i ) SEQUENCE CHARACTERISTICS:
　　　　( A ) LENGTH: 40 base pairs
　　　　( B ) TYPE: nucleic acid
　　　　( C ) STRANDEDNESS: single
　　　　( D ) TOPOLOGY: linear ( i i ) MOLECULE TYPE: DNA ( x i ) SEQUENCE DESCRIPTION: SEQ ID NO:39:

GATCTCCGAA TTCCATGGAT CCAGGCCTCT AGAAGCTTAC　　　　　　　　　　40

( 2 ) INFORMATION FOR SEQ ID NO:40:

( i ) SEQUENCE CHARACTERISTICS:
　　　　( A ) LENGTH: 40 base pairs
　　　　( B ) TYPE: nucleic acid
　　　　( C ) STRANDEDNESS: single
　　　　( D ) TOPOLOGY: linear ( i i ) MOLECULE TYPE: DNA ( x i ) SEQUENCE DESCRIPTION: SEQ ID NO:40:

AGGCTTAAGG TACCTAGGTC CGGAGATCTT CGAATGTTAA　　　　　　　　　　40

( 2 ) INFORMATION FOR SEQ ID NO:41:

( i ) SEQUENCE CHARACTERISTICS:
　　　　( A ) LENGTH: 7 amino acids
　　　　( B ) TYPE: amino acid
　　　　( C ) STRANDEDNESS: single
　　　　( D ) TOPOLOGY: unknown ( i i ) MOLECULE TYPE: peptide ( i x ) FEATURE:
　　　　( A ) NAME/KEY: Modified-site
　　　　( B ) LOCATION: 6
　　　　( D ) OTHER INFORMATION: /note= "Xaa=Ser or Ile or Val"

( x i ) SEQUENCE DESCRIPTION: SEQ ID NO:41:

His　Cys　Ser　Ala　Gly　Xaa　Gly
　　1　　　　　　　　　　5

( 2 ) INFORMATION FOR SEQ ID NO:42:

( i ) SEQUENCE CHARACTERISTICS:
　　　　( A ) LENGTH: 6 amino acids
　　　　( B ) TYPE: amino acid
　　　　( C ) STRANDEDNESS: single

```
        ( D ) TOPOLOGY: unknown ( i i ) MOLECULE TYPE: peptide ( x i ) SEQUENCE DESCRIPTION: SEQ ID NO:42:

His  Gln  Tyr  Trp  Pro  Glu
    1                    5

( 2 ) INFORMATION FOR SEQ ID NO:43:

( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: unknown ( i i ) MOLECULE TYPE: peptide ( i x ) FEATURE:
            ( A ) NAME/KEY: Modified-site
            ( B ) LOCATION: 2
            ( D ) OTHER INFORMATION: /note= "Xaa=Lys or Arg"

( x i ) SEQUENCE DESCRIPTION: SEQ ID NO:43:

Asn  Xaa  Xaa  Xaa  Xaa  Asn  Arg
    1                    5

( 2 ) INFORMATION FOR SEQ ID NO:44:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: unknown ( i i ) MOLECULE TYPE: peptide ( x i ) SEQUENCE DESCRIPTION: SEQ ID NO:44:

Gln  Tyr  Ile  Phe  Xaa  Xaa  Xaa  Xaa  Xaa  Xaa  Asp
    1                    5                         1 0

( 2 ) INFORMATION FOR SEQ ID NO:45:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: unknown ( i i ) MOLECULE TYPE: peptide ( x i ) SEQUENCE DESCRIPTION: SEQ ID NO:45:

His  Cys  Ser  Xaa  Gly  Xaa  Gly  Arg
    1                    5
```

| | . ** *.* *** *.* . . . |

PTP-S31: A NOVEL PROTEIN TYROSINE PHOSPHATASE

1. INTRODUCTION

The invention, in the fields of biochemistry and cell and molecular biology, relates to a novel protein tyrosine phosphatase (PTPase or PTP) protein or glycoprotein, termed PTP-S31, the use of such molecule in pharmaceutical preparations, and pharmaceutical compositions comprising PTP-S31 or functional derivatives thereof. This invention is also directed to nucleic acid molecules encoding the PTP-S31 protein or functional derivative, recombinant expression vectors carrying the nucleic acid molecules, cells containing the recombinant expression vectors, methods for production and identification of PTP-S31 or the DNA coding therefor, antibodies specific for PTP-S31, and methods for screening compounds capable of binding to and inhibiting or stimulating protein tyrosine phosphatase enzymatic activity of PTP-S31.

2. BACKGROUND OF THE INVENTION

Phosphorylation of proteins is a fundamental mechanism for regulating diverse cellular processes. While the majority of protein phosphorylation occurs at serine and threonine residues, phosphorylation at tyrosine residues is attracting a great deal of interest since the discovery that many oncogene products and growth factor receptors possess intrinsic protein tyrosine kinase activity. The importance of protein tyrosine phosphorylation in growth factor signal transduction, cell cycle progression and neoplastic transformation is now well established (Hunter et al., *Ann. Rev. Biochem.* 54:987–930 (1985), Ullrich et al., *Cell* 61:203–212 (1990), Nurse, *Nature* 344:503–508 (1990), Cantley et al., *Cell* 64:281–302 (1991)).

Biochemical studies have shown that phosphorylation on tyrosine residues of a variety of cellular proteins is a dynamic process involving competing phosphorylation and dephosphorylation reactions. The regulation of protein tyrosine phosphorylation is mediated by the reciprocal actions of protein tyrosine kinases (PTKases or PTKs) and protein tyrosine phosphatases (PTPs). The tyrosine phosphorylation reactions are catalyzed by PTKs. Tyrosine phosphorylated proteins can be specifically dephosphorylated through the action of PTPs. The level of protein tyrosine phosphorylation of intracellular substances is determined by the balance of PTK and PTP activities. (Hunter, T., *Cell* 58:1013–1016 (1989)).

2.1. PTKs

The protein tyrosine kinases (PTKs; ATP:protein-tyrosine O-phosphotransferase, EC 2.7.1.112) are a large family of proteins that includes many growth factor receptors and potential oncogenes. (Hanks et al., *Science* 241:42–52 (1988)). Many PTKs have been linked to initial signals required for induction of the cell cycle (Weaver et al., *Mol. and Cell. Biol.* 11(9):4415–4422 (1991)). PTKs comprise a discrete family of enzymes having common ancestry with, but major differences from, serine/threonine-specific protein kinases (Hanks et al., supra). The mechanisms leading to changes in activity of PTKs are best understood in the case of receptor-type PTKs having a transmembrane topology (Ullrich et al. (1990) supra). The binding of specific ligands to the extracellular domain of members of receptor-type PTKs is thought to induce their oligomerization leading to an increase in tyrosine kinase activity and activation of the signal transduction pathways (Ullrich et al., (1990) supra). Deregulation of kinase activity through mutation or overexpression is a well-established mechanism for cell transformation (Hunter et al., (1985) supra; Ullrich et al., (1990) supra).

2.2. PTPs

The protein phosphatases are composed of at least two separate and distinct families (Hunter, T.(1989) supra) the protein serine/threonine phosphatases and the protein tyrosine phosphatases (PTPs; protein-tyrosine-phosphate phosphohydrolase, EC 3.13.48)). The PTPs are a family of proteins that have been classified into two subgroups. The first subgroup is made up of the low molecular weight, intracellular enzymes that contain a single conserved catalytic phosphatase domain. All known intracellular type PTPs contain a single conserved catalytic phosphatase domain. Examples of the first group of PTPs include (1) placental PTP 1B (Charbonneau et al., *Proc. Natl. Acad. Sci. USA* 86:5252–5256 (1989); Chernoff et al., *Proc. Natl. Acad. Sci. USA* 87:2735–2789 (1990)), (2) T-cell PTP (Cool et al. *Proc. Natl. Acad. Sci. USA* 86:5257–5261 (1989)), (3) rat brain PTP (Guan et al., *Proc. Natl. Acad. Sci. USA* 87:1501–1502 (1990)), (4) neuronal phosphatase (STEP) (Lombroso et al., *Proc. Natl. Acad. Sci. USA* 88:7242–7246 (1991)), and (5) cytoplasmic phosphatases that contain a region of homology to cytoskeletal proteins (Guet al., *Proc. Natl. Acad. Sci. USA* 88:5867–57871 (1991); Yang et al., *Proc. Natl. Acad. Sci. USA* 88:5949–5953 (1991)).

The second subgroup is made up of the high molecular weight, receptor-linked PTPs, termed RPTPs. RPTPs consist of (a) an intracellular catalytic region, (b) a single transmembrane segment, and (c) a putative ligand-binding extracellular domain. The structures and sizes of the putative ligand-binding extracellular "receptor" domains of RPTPs are quite divergent. In contrast, the intracellular catalytic regions of RPTPs are highly homologous. All RPTPs have two tandemly duplicated catalytic phosphatase homology domains, with the prominent exception of an RPTP termed HPTPβ, which has only one catalytic phosphatase domain. (Tsai et al., *J. Biol. Chem.* 266:10534–10543 (1991)).

One example of RPTPs is a family of proteins termed leukocyte common antigens (LCA) (Ralph, S. J., *EMBO J.* 6:1251–1257 (1987)) which are high molecular weight glycoproteins expressed on the surface of all leukocytes and their hemopoietic progenitors (Thomas, *Ann. Rev. Immunol.* 7:339–369 (1989)). A remarkable degree of similarity exists in the sequences of LCA from several species (Charbonneau et al., *Proc. Natl. Acad. Sci. USA* 85:7182–7186 (1988)). LCA has been referred to in the literature by different names, including T200 (Trowbridge et al., *Eur. J. Immunol.* 6:557–562 (1962)), B220 for the B lymphocyte form (Coffman et al., *Nature* 289:681–683 (1981)), the mouse allotypic marker Ly-5 (Komuro et al., *Immunogenetics* 1:452–456 (1975)), and more recently CD45 (Cobbold et al., *Leucocyte Typing III*, A. J. McMichael et al., eds., pp. 788–803 (1987)).

CD45 appears to play a critical role in T cell activation (reviewed in Weiss A., *Ann. Rev. Genet.* 25:487–510 (1991)). For example, T-cell clones that were chemically mutagenized and selected for their failure to express CD45 had impaired responses to T-cell receptor stimuli (Weaver et al., supra). These T-cell clones were functionally defective in their responses to signals transmitted through the T cell antigen receptor, including cytolysis of appropriate targets, proliferation, and lymphokine production (Weaver et al., supra). Other studies indicate that the PTP activity of CD45 plays a role in the activation of pp56$^{lck}$, a lymphocyte-specific PTK (Mustelin et al., *Proc. Natl. Acad. Sci. USA* 86:6302–6306 (1989); Ostergaard et al., *Proc. Natl. Acad. Sci. USA* 86:8959–8963 (1989)). These authors hypothesized that the phosphatase activity of CD45 activates pp56$^{lck}$ by dephosphorylation of a C-terminal tyrosine residue, which may, in turn, be related to T-cell activation.

Another example of an RPTP is the leukocyte common antigen related molecule (LAR), initially identified as a homologue of LCA (Streuli et al., *J. Exp. Med.* 168:1523–1530 (1988)). Although the intracellular catalytic region of the LAR molecule contains two catalytic phosphatase homology domains (domain I and domain II), mutational analyses suggested that only domain I had catalytic phosphatase activity, whereas domain II was enzymatically inactive (Streuli et al., *EMBO J.* 9(8):2399–2407 (1990)). Chemically induced LAR mutants having tyrosine at amino acid position 1379 changed to a phenylalanine were temperature-sensitive (Tsai et al., *J. Biol. Chem.* 266(16):10534–10543 (1991)).

A recently cloned mouse RPTP, designated mRPTPμ, was found to have an extracellular domain that shared some structural motifs with LAR. (Gebbink, M. F. B. G. et al., *FEBS Lett.* 290:123–130 (1991). These authors also cloned a human homologue of RPTPμ and localized the gene on human chromosome 18.

Two Drosophila PTPs, termed DLAR and DPTP, have been predicted based on the sequences of cDNA clones (Streuli et al., *Proc. Natl. Acad. Sci. USA* 86:8698–8702 (1989)). cDNAs coding for another Drosophila RPTP, termed DPTP 99A, have been cloned and characterized (Hariharan et al., *Proc. Natl. Acad. Sci. USA* 88:11266–11270 (1991)).

Other examples of RPTPs include RPTP-α, β, γ, and ζ (Krueger et al., *EMBO J.* 9:3241–3252 (1990), Sap et al. *Proc. Natl. Acad. Sci. USA* 87::6112–6116 (1990), Kaplan et al., *Proc. Natl. Acad. Sci. USA* 87:7000–7004 (1990), Jirik et al., *FEBS Lett.* 273:239–242 (1990), Mathews et al., *Proc. Natl. Acad. Sci. USA* 87:4444–4448 (1990), Ohagi et al., *Nucl. Acids Res.* 18:7159 (1990)). Schlessinger, PCT Publication WO92/01050 (23 Jan. 1992) disclosed human RPTP-α, β and γ, and described the nature of the structural homologies among the conserved domains of these three RPTPs and other members of this protein family. The murine RPTP-α has 794 amino acids, whereas the human RPTP-α has 802 amino acids. RPTP-α has an intracellular domain homologous to the catalytic domains of other tyrosine phosphatases. The 142 amino acid extracellular domain (including signal peptide of RPTP-α) has a high serine and threonine content (32%) and 8 potential N-glycosylation sites. cDNA clones have been produced that code for the RPTP-α, and RPTP-α has been expressed from eukaryotic hosts. Northern analysis was used to identify the natural expression of RPTP-α in various cells and tissues. A polyclonal antibody to RPTP-α, produced by immunization with a synthetic peptide of RPTP-α, identifies a 130 kDa protein in cells transfected with a cDNA clone encoding a portion of RPTP-α.

Another RPTP, HePTP (Jirik et al., *FASEB J.* 82082 (1990) Abstract 2253) was discovered by screening a cDNA library derived from a hepatoblastoma cell line, HepG2, with a probe encoding the two PTP domains of LCA. The HePTP gene appeared to be expressed in a variety of human and murine cell lines and tissues.

Since the initial purification, sequencing, and cloning of a PTP, additional potential PTPs have been identified at a rapid pace. The number of different PTPs that have been identified is increasing steadily, leading to speculations that this family may be as large as the PTK family (Hunter (1989) supra).

Conserved amino acid sequences designated "consensus sequences" have been identified in the catalytic domains of known PTPs (Krueger et al., *EMBO J.* 9:3241–3252 (1990) and Yi et al., *Mol. Cell. Biol.* 12:836–846 (1992), which are incorporated herein by reference). Yi et al. aligned the catalytic phosphatase domain sequences of the following PTPs: LCA, PTP1B, TCPTP, LAR, DLAR, and HPTPα, HPTPβ, and HPTPγ. This alignment includes the following "consensus sequences" (Yi et al., supra, FIG. 2(A)):

1. K C X X Y W P [SEQ ID NO:1]
2. HCS X G X G RX G [SEQ ID NO:2]

Krueger et al., aligned the catalytic phosphatase domain sequences of PTP1B, TCPTP, LAR, LCA, HPTPα, β, 8, ε and ζ, and DLAR and DPTP. This alignment includes the following "consensus sequences: (Krueger et al., supra, FIG. 7):

1. K C X X Y W P [SEQ ID NO:1]
2. HCS X G X G RX G [SEQ ID NO:2]

It is becoming clear that dephosphorylation of tyrosine residues can by itself function as an important regulatory mechanism. Dephosphorylation of a C-terminal tyrosine residue has been shown to activate tyrosine kinase activity in the src family of tyrosine kinases (Hunter, *T. Cell* 49:1–4 (1987)). Tyrosine dephosphorylation has been suggested to be an obligatory step in the mitotic activation of the maturation-promoting factor (MPF) kinase (Morla et al., *Cell* 58:193–203 (1989)). These observations point out the need in the art for understanding the mechanisms that regulate tyrosine phosphatase activity.

It is clear that further analysis of structure-function relationships among PTPs are needed to gain important understanding of the mechanisms of signal transduction, cell cycle progression and cell growth, and neoplastic transformation. Such understanding will also provide useful agents for regulating these processes and for treating diseases associated with their dysregulation.

3. SUMMARY OF THE INVENTION

The inventors describe herein the identification of a novel PTP, termed PTP S31. This novel PTP differs significantly in structure from previously reported PTPs. Further, several variants of this PTP have been identified. The present invention thus provides a PTP-S31 protein or glycoprotein which is a PTP or contain structural features known to be found in PTPs, as well as variants thereof.

When a PTP-S31 protein or glycoprotein of the present invention is one which occurs in nature, it is substantially free of other proteins or glycoproteins with which it is natively associated. A substantially pure PTP-S31 protein or glycoprotein of the invention may be produced by biochemical purification, by chemical means or by recombinant means in a prokaryotic or eukaryotic host, and is provided substantially free of other proteins with which it is natively associated. The PTP-S31 may have modified amino acids.

The invention is further directed to:

(1) a fragment of a PTP-S31 protein or glycoprotein;

(2) a PTP-S31 protein or glycoprotein having additional amino acids;

(3) a PTP-S31 protein or glycoprotein having substituted amino acids; and (4) a PTP-S31 protein or glycoprotein having any combination of deleted, additional, or substituted amino acids.

In all cases the modified PTP-S31 protein or glycoprotein, or fragment thereof, possesses the desired biological activity.

The invention is further directed to a nucleic acid molecule comprising a nucleotide sequence encoding a PTP-S31 protein according to the invention. The nucleic acid molecule may be cDNA, genomic DNA or RNA. The invention is further directed to a nucleic acid construct in the form of an expression vehicle. Also provided are prokaryotic and eukaryotic host cells containing the expression vehicle.

Also included in the present invention is a process for preparing a PTP-S31 protein or glycoprotein of this invention, comprising:

(a) culturing a host capable of expressing a PTP-S31 protein or glycoprotein under culturing conditions, (b) expressing the PTP-S31 protein or glycoprotein; and (c) recovering the PTP-S31 protein or glycoprotein from the culture.

The invention is also directed to a polyclonal, monoclonal or chimeric antibody specific for a PTP-S31 protein or glycoprotein or for an epitope of a PTP-S31 protein or glycoprotein.

The invention is further directed to a method for detecting the presence, or measuring the quantity, of a PTP-S31 protein or glycoprotein in a sample, preferably a cell or a biological sample from a subject, comprising:

(a) contacting the sample, such as a preparation of cells or an extract thereof, with an antibody specific for an epitope of a PTP-S31 protein or glycoprotein; and (b) detecting the binding of the antibody to sample material, or measuring the quantity of antibody bound, thereby detecting the presence or measuring the quantity of the PTP-S31 protein or glycoprotein.

The invention is also directed to a method for detecting the presence of a nucleic acid encoding a normal or mutant PTP-S31 protein or glycoprotein in a sample, preferably a cell or biological sample of a subject, comprising:

(a) contacting the sample, such as a cell or an extract thereof, with an oligonucleotide probe encoding at least a portion of a normal or mutant PTP-S31 protein or glycoprotein under hybridizing conditions; and (b) measuring the hybridization of the probe to nucleic acid of the cell, thereby detecting the presence of the nucleic acid. The nucleic acid of the sample can be selectively amplified, for example, by using the polymerase chain reaction, prior to assay.

The present invention is also directed to a method for identifying or isolating in a sample, preferably a chemical or biological sample, a compound capable of binding to a PTP-S31 protein or glycoprotein, the method comprising:

(a) attaching a PTP-S31 protein or glycoprotein or the compound-binding portion thereof to a solid phase matrix or carrier;

(b) contacting the sample with the PTP-S31 bound to the solid phase matrix, allowing any compound to bind to said PTP-S31, and washing away any unbound material;

(c) detecting the presence of the compound bound to the solid phase.

For purposes of isolation, the bound compound is subjected to the additional step of (d) eluting the bound compound, thereby isolating the compound.

The invention includes a method for identifying an agent molecule capable of stimulating or inhibiting the enzymatic activity of PTP-S31, comprising:

(a) contacting the agent with a PTP-S31 protein or glycoprotein, or a fragment thereof, which PTP-S31 may be in pure form, in a membrane preparation, or in a whole live or fixed cell;

(b) incubating the mixture of step (a) for a sufficient interval;

(c) measuring the enzymatic activity of the PTP-S31;

(d) comparing the enzymatic activity to that of the PTP-S31 protein or glycoprotein incubated without the agent, thereby determining whether the agent stimulates or inhibits the enzymatic activity.

In addition, the present invention provides methods for identifying agonists or antagonists of PTP-S31 action based on the ability of such agents to modulate interactions between (a) PTP-S31 and its target molecules or (b) PTP-S31 and molecules which regulate its enzymatic activity. Compounds identified by such methods may be useful to treat diseases associated with PTP-S31 dysfunction or with disordered signal transduction.

4. DESCRIPTION OF THE FIGURES

FIG. 1 presents the partial cDNA sequence [SEQ ID NO:3] and the deduced amino acid sequence [SEQ ID NO:4] of PTP-S31, which is a PCR fragment.

FIG. 2 shows a comparison of the deduced amino acid sequences of the PTP-S31 PCR fragment [SEQ ID NO:4] shown in FIG. 1 with the amino acid sequence of PTP 1B [SEQ ID NO:5] (Chernoff et al., supra). The GAP alignment method is used (Needleman et al., *J. Mol. Biol.* 48:443–453 (1970)).

FIGS. 3A–3D present the cDNA sequence [SEQ ID NO:6] and the deduced amino acid sequence [SEQ ID NO:7] of PTP-S31C, a cDNA clone (1.20.4) obtained from an RD cell cDNA library (#1). This partial cDNA sequence includes the cDNA sequence of the PCR fragment shown in FIG. 1.

FIGS. 4A–4B show a comparison of the deduced amino acid sequence of the PTP-S31C cDNA clone shown in FIGS. 3A–3D with the amino acid sequence of PTP 1B [SEQ. ID NO:5]. The GAP alignment method is used (Needleman et al., supra).

FIGS. 5A–5B present the cDNA sequence [SEQ ID NO:8] and the deduced amino acid sequence [SEQ ID NO:9] of a PCR fragment obtained with oligonucleotides nos. 223 and 224.

FIGS. 6A–6D show the combined cDNA sequence [SEQ ID NO:10] and the deduced amino acid sequence [SEQ ID NO:11] of PTP-S31D. This cDNA sequence includes the cDNA sequence of the PCR fragment shown in FIGS. 5A–5B.

FIG. 7 shows a comparison of the amino acid sequence of PTP-S31D and the sequences of PTP 1B, the first PTP domain of CD45 [SEQ ID NO:12] (Ralph et al. *EMBO J.* 6:1251–1257 (1987)) and LAR [SEQ ID NO:13] (Streuli et al *J. Exp. Med.* 168:1523–1530 (1988)), respectively. The CLUSTAL program is used (Higgins, C. et al., *Multiple Sequence Alignment*; CABIOS (1991).

FIG. 8 shows the results of a PTP enzymatic assay using p-nitrophenyl phosphate (pNP-P) as a substrate. The activity of the glutathione-S-transferase(GST)/PTP-S31D fusion protein is compared with that of the GST/PTP-S31C fusion protein and glutathione-S-transferase (negative control).

FIGS. 9A–9E shows the cDNA sequence [SEQ ID NO:14] and the deduced amino acid sequence [SEQ ID NO:15] of the longest PTP-S31D cDNA clone (S31D-63) isolated from a cDNA library (#2) made from human skeletal muscle mRNA. The 5' end of this clone differs from that of the PTP-S31C clone isolated from an RD cDNA library (FIGS. 3A–3D). An arrow indicates the position where this clone differs from PTP-S31C.

FIG. 10 presents a schematic overview of the different types of PTP-S31 clones identified in human skeletal muscle cDNA libraries #2 and #3. Only the 5' ends which differ from the PTP-S31C cDNA clone (FIGS. 3A–3D) are depicted.

FIG. 11 shows the deduced amino acid sequences of PTP-S31 variants found in human skeletal muscle, including S31-14 [SEQ ID NO:16], S31-2 [SEQ ID NO:17], S31-5 [SEQ ID NO:18], S31-63 [SEQ ID NO:19] and S31-III [SEQ ID NO:20].

FIGS. 12A–12D show a partial cDNA sequence [SEQ ID NO:21] and the predicted amino acid sequence [SEQ ID NO:22] of a cDNA clone, PTPS31-RD#2, isolated from an RD λ ZAP II cDNA library (library #14). The putative transmembrane region is underlined.

FIG. 13 shows an alignment of a portion of the amino acid sequences of PTPS31-RD#2 and the interleukin 2 receptor β chain (SEQ ID NO:23). Only the parts of the extracellular domains adjacent to the transmembrane regions are shown.

Figure 8:
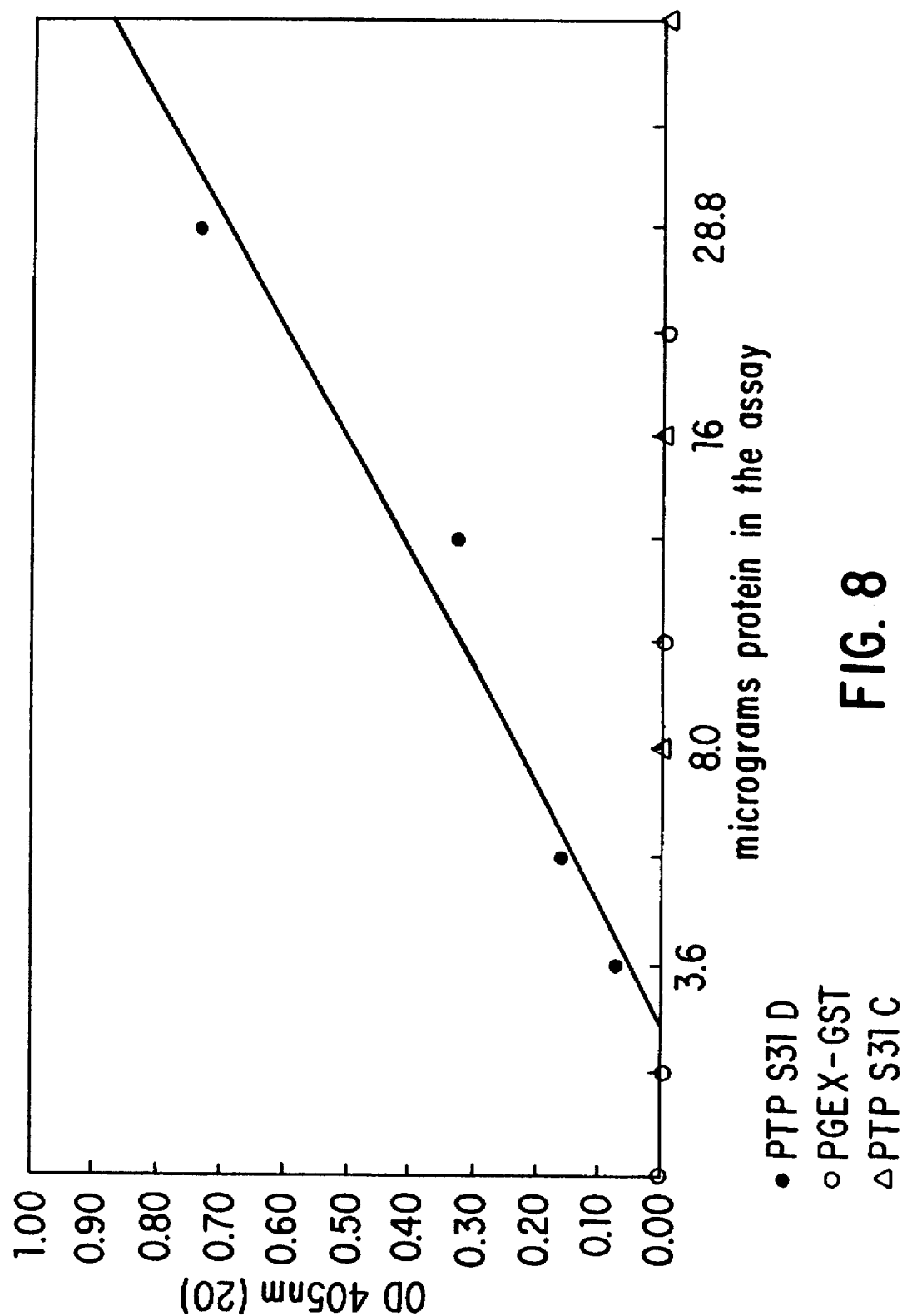

FIG. 14 shows fibronectin type III-like domains of the extracellular regions of PTP-S31 [SEQ ID NO:22]. The most C-terminal domain is denoted S31-FN-1 and the most N-terminal domain is S31-FN-4. The FN-like domains are aligned to a type III domain (labeled FN-III) (SEQ ID NO:24) of human fibronectin (Kornblihtt et al., *EMBO J.* 4:1755–1759 (1985)).

FIG. 15 shows an alignment of the amino acid sequence of part of the extacellular region of PTP-S31-RD#2 (designated PTPS31 in the Figure) with the human insulin receptor (IR) (SEQ ID NO:25), the human insulin-like growth factor 1 receptor (IGF1R) (SEQ ID NO:26) and the human insulin-related receptor (IRR) (SEQ ID NO:27).

5. DETAILED DESCRIPTION OF THE INVENTION

Through the use of recombinant DNA methods, the present inventors have identified a novel mammalian protein tyrosine phosphatases (PTP; EC 3.1.3.48), termed PTP-S31, of human origin, and several derivatives thereof. The present inventors have produced cDNA clones coding for the novel protein, and expressed the protein in *E. coli* and in eukaryotic 293 cells. Northern analysis has been used to identify the natural expression of the protein in various cells and tissues. They have further produced a polyclonal antibody to the protein by immunization with a recombinant fusion protein including the PTP-S31 variant, PTP-S31D.

5.1. IDENTIFICATION OF AGENTS WHICH MODULATE PTP ACTIVITY

The PTP-S31 protein or glycoprotein, or derivatives thereof having enzymatic activity, can be used for testing of compounds capable of enhancing or inhibiting the phosphatase activity. The ability of a compound under testing to modify phosphatase activity can be tested in an in vitro system wherein the test compound is added to a purified PTP-S31 protein or glycoprotein or enzymatically active derivatives thereof, and the affects on enzyme activity measured using standard enzymological procedures well known to those of skill in art.

Alternatively, the action of a compound on PTP activity can be measured in a whole cell preparation using live or fixed cells, or a fraction derived from live or fixed cells. This method is useful for screening compounds acting on the protein, in particular, on the enzymatic portion of the protein. A test compound is incubated with cells, or with a preparation derived therefrom, which express high amounts of the PTP of this invention, such as transfected COS or NIH-3T3 cells. The amount of cellular phosphotyrosine is measured, using methods well-known in the art (Honegger et al., *Cell* 51:199–209 (1987); Margolis et al., *Cell* 51:1101–1107 (1989)). The results are compared to results obtained in the absence of the test compound, or in the absence or presence of a known activator of PTP. In such studies, the action of the test compound in the presence of an activator tyrosine kinase can also be measured.

A compound which stimulates PTP activity will result in a net decrease in the amount of phosphotyrosine, whereas a compound which inhibits PTP activity will result in a net increase in the amount of phosphotyrosine.

5.2. TREATMENT OF DISEASES ASSOCIATED WITH PTP FUNCTION OR DYSFUNCTION

The invention also relates to the use of such identified antagonists or agonists in pharmaceutical compositions intended for treatment of diseases or conditions associated with abnormal expression of a PTP-S31 protein or glycoprotein. Alternatively, the pharmaceutical compositions may be used to treat a disease or condition associated with normal PTP-S31 but one or more deficiencies downstream in the signal transduction pathway or even a condition without any down stream deficiencies. The composition may typically be in a form for systemic or topical injection or infusion and may, as such, be formulated with a suitable carrier for injection or infusion.

The present invention also relates to a method for preventing or treating diseases or conditions involving the activation of PTP-S31, the method comprising administering, to a patient in need thereof, an effective dosage of a PTP-S31 protein or glycoprotein of the invention or an antibody of the invention or a molecule that stimulates or inhibits enzymatic activity of an PTP protein of the invention.

In the case of growth factor receptors which are tyrosine kinases, such as the receptors for epidermal growth (EGF) and for platelet-derived growth factor (PDGF), tyrosine phosphorylation is linked to cell growth and to oncogenic transformation. Activation of a PTP, leading to dephosphorylation would serve as a counterregulatory mechanism to prevent or inhibit growth, and might serve as an endogenous regulatory mechanism against cancer. Thus, mutation or regulation of this receptor/enzyme system may promote susceptibility to cancer.

The insulin receptor is also a tyrosine kinase, and phosphorylation of tyrosine in cells bearing insulin receptors would be associated with normal physiological function associated with insulin. Three specific tyrosine residues in the intracellular portion of the insulin receptor are phosphorylated when insulin binds to the extracellular domain. At the same time, the insulin receptor becomes an active enzyme which can phosphorylate itself or other proteins at tyrosine residues. Phosphorylation of all three specific intracellular tyrosines of the insulin receptor appears to be required for full tyrosine kinase activity. The fully active insulin receptor transmits the signal into the cell (such as skeletal muscle, liver, etc.) by phosphorylating intracellular proteins, which are thereby activated and convey the messages further downstream via the insulin signal transduction pathway. Thus, the well-known physiologic effects of insulin result from a cascade of phosphorylation events.

Insulin signal transduction is controlled tightly by enzymes of the PTP class, which can dephosphorylate, and in the case of the insulin receptor, deactivate, tyrosine kinases. The existence of PTPS with activity towards the insulin receptor can easily be demonstrated. In this setting, then, activation of a PTP would counteract insulin effects, whereas inhibition of the PTP should mimic insulin effects. In fact, treatment of whole cells such as skeletal muscle or adipocytes with pervanadate, which inhibits PTPs, induces an almost full insulin response (Fantus, I. G. et al., *Biochemistry* 28:8864–8871 (1989); Leighton, B. et al., *Biochem. J.* 276:289–292 (1989)). Once the PTP which specifically acts on the insulin receptor is identified, it can be employed in a high throughput screening system and for rational drug design, to identify compounds which, like pervanadate, inhibit the phosphatase and mimic the action of insulin.

Over-activity, or inappropriate activation, of a PTP would be expected to inhibit or totally prevent the action of insulin on cells, leading to diabetes (of an insulin-resistant variety). Thus, susceptibility to diabetes may be associated with PTP dysregulation, and may be diagnosed by measurement of PTP activity, including PTP-S31.

Therefore, the methods of the present invention for identifying normal or mutant PTP-S31 genes, or for measuring the amount or activity of PTP-S31 associated with a cell or tissue, can serve as methods for identifying susceptibility to cancer, diabetes, or other diseases associated with alterations in cellular phosphotyrosine metabolism. In addition, the PTP-S31 protein, functional derivatives thereof, and agents which modulate (activate or inhibit) PTP-S31 enzymatic activity may be used to treat or prevent the development of diseases such as cancer and diabetes.

5.3. DETECTION AND MEASUREMENT OF PTP-S31 PROTEIN OR NUCLEIC ACID

The present invention provides methods for evaluating the presence and the level of normal or mutant PTP-S31 in a subject. Absence, or more typically, low expression of the PTP-S31, or presence of a mutant PTP-S31, in an individual may serve as an important predictor of susceptibility to oncogenic transformation and the development of cancer. Alternatively, over-expression of PTP-S31 possibly due to a mutant receptor/enzyme system insensitive to negative regulation, or due to overabundance of a stimulatory factor present in the body, may serve as an important predictor of susceptibility to diabetes.

Oligonucleotide probes encoding various portions of the PTP-S31 (see below) are used to test cells from a subject for the presence of DNA or RNA sequences encoding the PTP. A preprobe would be one directed to the nucleic acid sequence encoding at least 4 amino acid residues, and preferably at least 5 amino acid residues, of the PTP-S31 protein or glycoprotein of the present invention. Qualitative or quantitative assays can be performed using such probes. For example, Northern analysis (see Examples, below) is used to measure expression of an PTP mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al., *MOLECULAR CLONING: A LABORATORY MANUAL*, Second Edition, Cold Spring Harbor Press, Cold Spring Harbor, N.Y. (1989), which references are herein incorporated by reference).

An in vitro enzymatic method which is capable of increasing the concentration of such desired nucleic acid molecules is referred to as the "polymerase chain reaction (PCR) (Mullis et al., *Cold Spring Harbor Symp. Quant. Biol.* 51:263–273 (1986); Erlich et al., EP 50,424; EP 84,796, EP 258,017, EP 237,362; Mullis, K. EP 201,184; Mullis et al., U.S. Pat. No. 4,683,202; Erlich, H., U.S. Pat. No. 4,582,788; and Saiki et al., U.S. Pat. No. 4,683,194). The PCR provides a method for selectively increasing the concentration of a particular nucleic sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'-3' linkage of the phosphate of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR are selected such that they contain sequences identical to, or complementary to, sequences which flank the particular nucleic acid sequence whose amplification is desired.

More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the PCR, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature double-stranded molecules which may be present. The "first" and "second" probes are then added to the sample at a concentration which greatly exceeds that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded "second" probes will be extended. The extension of the "first" probe will result synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold Spring Harbor Symp. Quant. Biol.* 51:263–273 (1986)); Saiki et al., *Bio/Technology* 3:1008–1012 (1985)); and Mullis et al., *Meth. Enzymol.* 155:335–350 (1987)).

5.4. PTP-S31 PROTEINS AND FUNCTIONAL DERIVATIVES

In one embodiment, the present invention is directed to a naturally occurring mammalian PTP-S31 protein or glycoprotein. In another embodiment, the invention is directed to a recombinant mammalian PTP-S31 protein or glycoprotein. The preferred PTP-S31 protein or glycoprotein of the present invention is of human origin. The invention provides the naturally occurring molecule substantially free of other proteins with which it is natively associated. "Substantially free of other proteins" indicates that the protein has been purified away from at least 90 percent (on a weight basis), and from even at least 99 percent if desired, of other proteins and glycoproteins with which it is natively associated, and is therefore substantially free of them. That can be achieved by subjecting the cells, tissue or fluids containing the RPTP to standard protein purification techniques such as immunoadsorbent columns bearing monoclonal antibodies reactive against the protein. Other forms of affinity purification can utilize solid-phase substrates which can bind the PTP domain, or a ligand that will bind to the receptor domain. Alternatively, the purification can be achieved by a combination of standard methods, such as ammonium sulfate precipitation, molecular sieve chromatography, and ion exchange chromatography.

In another embodiment, the present invention is directed to a peptide having an amino acid sequence corresponding to PTP-S31 or at least 9 contiguous amino acids thereof, more preferably at least 10, 15 20 or 30 contiguous amino acids thereof.

It will be understood that the mammalian PTP-S31 of the present invention can be biochemically purified from a variety of cell or tissue sources. For preparation of naturally occurring PTP-S31, such as mammalian skeletal muscle, especially of human origin, are preferred.

Alternatively, because the nucleic acid molecule encoding PTP-S31 can be isolated or synthesized, the polypeptide can be synthesized substantially free of other proteins or glycoproteins with which it is natively associated in a prokaryotic organism or in a non-mammalian eukaryotic organism, if desired. As intended by the present invention, a recombinant PTP-S31 molecule produced in mammalian cells, such as transfected COS, NIH-3T3, CHO, or 293 cells, etc., for example, is either a naturally occurring protein sequence or a functional derivative thereof. Where a naturally occurring protein is produced by recombinant means, it is provided substantially free of the other proteins and glycoproteins with which it is natively associated.

Alternatively, methods are well known for the synthesis polypeptides of desired sequence on solid phase supports and their subsequent separation from the support.

In a further embodiment, the invention provides "functional derivatives" of PTP-S31. By "functional derivative" is meant a "fragment," "variant," "analog," or "chemical derivative" of the PTP-S31, which terms are defined below. A functional derivative retains at least a portion of the function of the PTP-S31, such as binding to a specific antibody or phosphatase enzymatic activity which permits its utility in accordance with the present invention.

A "fragment" of PTP-S31 refers to any subset of the molecule, that is, a shorter peptide. The term "fragment" is used to indicate a polypeptide which is derived from a PTP-S31 protein having a naturally occurring protein sequence by appropriately modifying the DNA sequence encoding the PTP-S31 protein, resulting in deletion of one or more amino acids at one or more sites of the C-terminal, N-terminal, and within the native sequence. Fragments of a PTP-S31 protein or glycoprotein are useful for screening for compounds that are antagonists or agonists (as defined below). It is understood that such fragments of a PTP-S31 protein or glycoprotein may retain characterizing portion(s) of the native PTP-S31. In particular, such fragments should retain one or more biological activities or functions which are characteristic for the intact PTP-S31 protein or glycoprotein. Examples, which are not intended to be in any way limiting to the scope of the invention claimed, of PTP-S31 fragments are: a) the catalytic domain; b) regions of the PTP-S31 protein or glycoprotein which interacts with other molecules in the intact cell; c) regulatory parts of PTP0-S31.

A "variant" of PTP-S31 refers to a molecule substantially similar to either the entire peptide or a fragment thereof. Variant peptides may be conveniently prepared by direct chemical synthesis of the variant peptide, using methods well known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

In a further aspect, the invention provides a PTP-S31 protein or glycoprotein having additional amino acids that is derived from a naturally occurring PTP-S31 protein or glycoprotein by appropriately modifying the DNA sequence encoding the protein, resulting in addition of one or more amino acids at one or more sites of the C-terminal, N-terminal, and within the native sequence. It is understood that such a PTP-S31 protein or glycoprotein having additional amino acids may retain characterizing portion(s) of the native PTP-S31 protein or glycoprotein. In particular, such a PTP-S31 protein or glycoprotein with additional amino acids should retain one or more biological activities or functions which are characteristic of the PTP-S31 protein or glycoprotein, examples of which include: (a) the catalytic activity; (b) the substrate specificity; (c) interaction with other molecules in the intact cell; (d) regulatory functions. These examples are not intended to be in any way limiting to the scope of the invention claimed.

In a further aspect, the invention provides a PTP-S31 protein or glycoprotein having substituted amino acids that is derived from a naturally occurring PTP-S31 protein or glycoprotein by appropriately modifying or mutating the DNA sequence encoding the protein, resulting in substitution of one or more amino acids at one or more sites of the C-terminal, N-terminal, and within the native amino acid sequence. It is understood that such a protein or having substituted amino acids may retain characterizing portion(s) of PTP-S31, and should preferably retain one or more biological activities or functions which are characteristic for the intact PTP-S31 protein or glycoprotein, for example: (a) the catalytic activity; (b) the substrate specificity; (c) interaction with other molecules in the intact cell; d) regulatory functions. These examples are not intended to be in any way limiting to the scope of the invention claimed.

Any combination of deletion, insertion, and substitution may also be made to arrive at the final construct of a PTP-S31 functional derivative, provided that the final construct possesses the desired activity or function present in the intact PTP-S31 protein or glycoprotein, for example: (a) the catalytic activity; (b) substrate specificity; (c) interaction with other molecules in vitro and in vivo; (d) regulatory functions. Only one of such activities or functions needs to be retained after any combination of deletion, insertion, and substitution. These examples are not intended to be in any way limiting to the scope of the invention claimed. Obviously, the modifications or mutations that will be made in the DNA encoding the PTP-S31 protein must not alter the reading frame and preferably will not create complementary regions that could produce secondary mRNA structure (see European Patent Publication No. EP 75,444). At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture (see below). The variants typically exhibit the same qualitative biological activity as the nonvariant peptide.

An "analog" of PTP-S31 refers to a non-natural molecule substantially similar to either the entire molecule or a fragment thereof.

A "chemical derivative" of PTP-S31 contains additional chemical moieties not normally a part of the peptide. Covalent modifications o the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with α-haloacetates (and corresponding amines) such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

Tyrosyl residues are well-known sites for chemical modification, in particular for introduction of spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or other macromolecular carriers. Commonly used cross-linking agents include, e.g., 1-1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3"dithiobis(succinimidyl-propionate), and bifunctional maleimides such as bis-N-maleimido-1,8-octane. Derivatizing agents such as methyl-3-[(p-azidophenyl)dithio]propioimidate intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642, 4,229, 537; and 4,330,440 are employed for protein immobilization.

Other modifications include hydroxylation of proline lysine, phosphorylation of hydroxyl groups of seryl or threonyl residues, methylation of the α-amino groups of lysine, arginine, and histidine side chains (T. E. Creighton, *Proteins: Structure and Molecule Properties*, W. H. Freeman & Co., Francisco, pp. 79–86 (1983)), acetylation of the N-terminal and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Hack Publishing Co., Easton, Pa. (1980).

5.5. CHIMERIC PTP-S31 MOLECULES

In a further aspect, the invention provides so-called chimeric molecules which are made up of other PTPs in which one or more specific amino acid sequences are replaced with homologous sequence(s) from another PTP protein or glycoprotein. Chimeric molecules may include, for example, a receptor-type PTP (RPTP) protein or glycoprotein having a ligand-binding extracellular domain that is grafted onto a portion of a PTP-S31 protein or glycoprotein. Other chimeric molecules included within the scope of the present invention include PTPs in which the catalytic phosphatase domain has been replaced with the phosphatase domain from PTP-S31. In this case, the preferred number of amino acids is between 220 and 260.

"Homologous sequences" are defined as sequences in two or more PTPs which are similarly positioned in the primary sequence and which may exhibit sequence homology. It should be emphasized that "homologous sequences" should not be limited to cases with high degree of homology. Chimeric molecules are important tools for elucidating structure-function relationships and for identifying specific compounds (drugs). Therefore, the most useful chimeras are often, but not always, molecules in which a certain portion of one molecule has been replaced with the similarly positioned, but divergent, sequence from another, otherwise homologous, molecule. Thus, the exchanged portions will quite often represent the parts of the molecules where they differ the most.

5.6. ANTIBODIES SPECIFIC FOR PTP-S31 AND THEIR USES IN DETECTING OR MEASURING PTP-s31

This invention is also directed to an antibody specific for an epitope of a PTP-S31 protein or glycoprotein, most preferably of human PTP-S31, and the use of such antibody to detect the presence of, or measure the quantity or concentration of, the PTP-S31 protein or glycoprotein in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein *Nature* 256:495–497 (1975) and U.S. Pat. No. 4,376,110. Such antibodies may be of any immunoglobulin class including IgG, IgM, IgE, IgA, and IgD, and any subclass thereof. The hybridoma producing the mAbs of this invention may be cultivated in vitro or in vivo. Production of the high titers of mAbs in vivo production makes this the presently preferred method of production. Briefly, cells from the individual hybridomas are injected intraperitoneally into pristane-primed BALB/c mice to produce ascites fluid high concentrations of the desired mAbs. MAbs of isotype IgM or IgG may be purified from such ascites fluids, or from culture supernatants, using column chromatography methods well known to hose of skill in the art.

Chimeric antibodies are molecules, different portions of which are derived from different animal species, such as those having variable region derived from a murine mAb and a human immunoglobulin constant region. Chimeric antibodies and methods for their production are known in the art (Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Neuberger et al., *Nature* 314:268–270 (1985); Taniguchi et al., European Patent Application 171496 (Feb. 19, 1985); Morrison et al., European Patent Application 173494 (Mar. 5, 1986); Neuberger et al., PCT Application WO86/01533 (Mar. 13, 1986); Kudo et al., European Patent Application 184187 published Jun. 11, 1986); Morrison et al., European Patent Application 173494 (published Mar. 5, 1986); Sahagan et al., *J. Immunol.* 137:1066–1074 (1986); Robinson et al., International Patent Publication #PCT/US86/02269 (published 7 May 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can prepared by immunizing an animal of the same species and genetic type (e.g., mouse strain) as the source of the mAb with the mAb to which an anti-Id is being prepared. The immunized animal will recognize and respond to the idiotypic determinants the immunizing antibody by producing an antibody to these idiotypic determinants (the anti-Id antibody).

The anti-Id antibody may also be used as an "immunogen" induce an immune response in yet another animal, producing a so-called anti-anti-Id antibody. The anti-anti-Id may be epitopically identical to the original mAb which induced the anti-Id. Thus, by using antibodies to the idiotypic determinants a mAb, it is possible to identify other clones expressing antibodies of identical specificity.

Accordingly, mAbs generated against PTP-S31 may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the final mAb specific for a PTP-S31 epitope.

The anti-Id mAbs thus have their idiotypic epitopes, or "idiotopes" structurally similar to the epitope being evaluated, such as PTP-S31.

The term "antibody" is also meant to include both intact molecules as well as fragments thereof, such as, for example, Fab and F(ab')$_2$, which are capable of binding antigen. Fab and F(ab')₂ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')₂ and other fragments of the antibodies useful in the present invention may be used for the detection and quantitation of PTP-S31 according to the methods disclosed herein for intact antibody molecules. Such fragments are typically produced by proteolytic cleavage, using enzymes such as papain (to produce Fab fragments) or pepsin (to produce F(ab')₂ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively detect the presence of cells which express PTP-S31. This can be accomplished by immunofluorescence techniques employing a fluorescently labeled antibody (see below) coupled with light microscopic, flow cytometric, of fluorimetric detection.

The antibodies (or fragments thereof) useful in the present invention may be employed histologically, as in immunofluorescence of immunoelectron microscopy, for in situ detection of PTP-S31. In situ detection may be accomplished by removing a histological specimen from a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of the PTP but also its distribution on the examined tissue. Using the present invention, those of ordinary skill will readily perceive that any of a wide variety of histological methods (such as staining procedures) can be modified in order to achieve such in situ detection. Such assays for PTP-S31 typically comprises incubating a biological sample, such as a biological fluid, a tissue extract, freshly harvested cells such a lymphocytes or leucocytes, or cells which have been incubated in tissue culture, in the presence of a detectably labeled antibody capable of identifying PTP-S31, and detecting the antibody by any of a number of techniques well-known in the art.

The biological sample may be treated with a solid phase support such as nitrocellulose, or other solid support which is capable of immobilizing cells, cell particles or soluble proteins. The support may then be washed with suitable buffers followed by treatment with the detectably labeled PTP-S31-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-PTP-S31 antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the PTP-S31-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect RPTP through the use of a radioimmunoassay (RIA) (see, for example, Work, T. S. et al., *Laboratory Techniques and Biochemistry in Molecular Biology*, North Holland Publishing Company, New York, 1978, which is incorporated by reference herein). The radioactive isotope can be detected by such means as the use of a gamma counter, or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{125}$Eu or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning PTP-S31 in a subject can also be tested using direct enzymatic assays, preferably for the tyrosine phosphatase activity. Such biochemical measurements can be performed in vitro, using purified enzymes, allowing precise measurements of enzyme activity, or with membrane preparations, or whole cells, where the net phosphotyrosine level is determined.

5.7. NUCLEIC ACID MOLECULES ENCODING PTP-S31

In additional embodiments of the present invention, a DNA sequence encoding a PTP-S31 molecule and methods for expressing the DNA sequence are provided. One of ordinary skill in the art will know how to identify and clone additional PTP molecules, of human or other mammalian species, which have sequence homology to the PTP-S31 protein and functional derivatives described herein, using the genetic sequences and oligonucleotides of the present invention without undue experimentation.

In one embodiment, the present invention is directed to an isolated nucleic acid molecule encoding a polypeptide having the amino acid sequence of PTP-S31, or having at least 9 contiguous amino acids thereof, preferably at least 10, 15, 20 or 30 contiguous amino acids. In a preferred embodiment, the isolated nucleic acid encodes a polypeptide having the amino acid sequence SEQ ID NO:4 or a mutant or species variant thereof. In another preferred embodiment, the isolated nucleic acid sequence comprises SEQ ID NO:3, or at least 27 contiguous nucleotides thereof, preferably at least 30, 35, 40 or 50 nucleotides thereof.

Manipulation of the genetic constructs of the present invention allow the grafting of a particular ligand-binding receptor domain and a transmembrane domain of an RPTP to a catalytic portions of PTP-S31 resulting in chimeric molecules. Non-limiting examples of such chimeric molecules include a PTP wherein the receptor is an epidermal growth factor receptor, a fibroblast growth factor receptor, and the like. Also contemplated are PTP-PTP chimeras, for example, between PTP-S31 and PTPα or PTPε. Genetically engineered chimeric receptors are known in the art (see, for example, Riedel, H. et al., *Nature* 324:628–670 (1986)).

Genetic constructs encoding PTP-S31, functional derivatives thereof, and chimeric molecules such as those described above, can be used in gene therapy. An abnormal or dysfunctional PTP-S31, which results in disease, may be replaced by infusion of cells of the desired lineage (such as hemopoietic cells, for example) transfected with DNA encoding normal PTP-S31. Alternatively, or additionally, cells carrying a chimeric RPTP having a receptor to a ligand of choice (e.g. EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)). Procedures for constructing recombinant molecules in accordance with the above-described method are disclosed by Sambrook et al. (supra).

The 3' terminus of the recombinant molecule of this invention is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support may be of any form (i.e. a sheet, rod, sphere, ovoid, etc.). Procedures for such immobilization are well known to those of ordinary skill. In the most preferred embodiment, the 3' end of the recombinant molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, and preferably, a large number of such recombinant molecule to the support.

Oligonucleotides representing a portion of PTP-S31 are useful for screening for the presence of genes encoding such proteins and for the cloning of PTP-S31 genes. Techniques for synthesizing such oligonucleotides are disclosed by, for example, Wu, R., et al., *Prog. Nucl. Acid. Res. Molec. Biol.* 21:101–141 (1978)).

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *Molecular Biology of the Gene*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lethe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding an PTP-S31 sequence is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding a PTP-S31 fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the PTP-S31 gene (Sambrook et al., supra).

A suitable oligonucleotide, or set of oligonucleotides, which is capable of encoding a fragment of an PTP-S31 gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the PTP-S31 gene. Single stranded oligonucleotide molecules complementary to the "most probable" PTP-S31 peptide-encoding sequences can be synthesized using procedures which are well known to those of ordinary skill in the art (Belagaje et al., *J. Biol. chem. Mechanisms in the Control of Gene Expression*; Nierlich et al., Eds., Acad. Press, New York (1976); Wu et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al. (supra), and by Hames et al. (In: *Nucleic Acid Hybridization, A Practical Approach*, IRL Press, Washington, D.C. (1985)), which references are herein incorporated by reference. Techniques such as, or similar to, those described above have successfully enabled the cloning of genes for human aldehyde dehydrogenases (Hsu et al., *Proc. Natl. Acad. Sci. USA* 82:3771–3775 (1985), fibronectin (Suzuki et al. *EMBO J.* 4:2519–2524 (1985), the human estrogen receptor gene (Walter et al., *Proc. Natl. Acad. Sci. USA* 82:7889–7893 (1985)), tissue-type plasminogen activator (Pennica et al., *Nature* 301:214–221 (1983)), and human term placental alkaline phosphatase complementary DNA (Dam et al., *Proc. Natl. Acad. Sci. USA* 82:715–8719 (1985)).

In an alternative way of cloning the PTP-S31 gene, a library of expression vectors is prepared by cloning DNA or, more preferably, cDNA (from a cell capable of expressing PTP-S31) into an expression vector. The library is then screened for members capable of expressing a protein which binds to an anti-PTP-S31 antibody, and which has a nucleotide sequence that is capable of encoding polypeptides that have the same amino acid sequence as PTP-S31, or fragments thereof. In this embodiment, DNA, or more preferably cDNA, is extracted and purified from a cell which is capable of expressing PTP-S31 protein. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translation control sequences) is capable of expression a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing PTP-S31 in order to produce a prokaryotic genomic expression vector library. Procedures for preparing cDNA and for producing a genomic library are disclosed by Sambrook et al. (supra).

A DNA sequence encoding PTP-S31 or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a PTP-S31-encoding sequence) are said to be operably linked if the nature of the linkage between the two DNA sequences does not (1) result in the introduction of a frame-shift mutation, (2) interfere with the ability of the promoter region sequence to direct the transcription of the R-PTP gene sequence, or (3) interfere with the ability of the R-PTP gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA sequence which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or of a "promoter sequence," a double-stranded molecule is created which will contain a functional promoter, if that extension proceeds towards the "promoter sequence" or the "promoter sequence complement." This functional promoter will direct the transcription of a nucleic acid sequence which is operably linked to that strand of the double-stranded molecule which contains the "promoter sequence".

Certain RNA polymerases exhibit a high specificity for such promoters. The RNA polymerases of the bacteriophages T7, T3 and SP-6 are especially well characterized, and exhibit high promoter specificity. The promoter sequences which are specific for each of these RNA polymerases also direct the polymerase to transcribe only one strand of the two strands of a duplex DNA template. The selection for which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S., et al., *J. Biol. Chem.* 263:1174–1181 (1984); Rosenberg, A. H., et al., *Gene* 59:191–200 (1987); Shinedling, S., et al., *J. Molec. Biol.* 195:471–480 (1987); Hu, M., et al., *Gene* 42:21–30 (1986)), T3, Sp6, and T7 (Chamberlin, M., et al., *Nature* 228:227–231 (1970); Bailey, J. N., et al., *Proc. Natl. Acad. Sci. USA* 80:2814–2818 (1983); Davanloo, P., et al., *Proc. Natl. Acad. Sci. USA* 81:2035–2039 (1984)) polymerases; the $P_R$ and $P_L$ promoters of bacteriophage lambda (*The Bacteriophage Lambda*, Hershey, A. D., ed., Cold Spring Harbor Press, Cold Spring Harbor, N.Y. (1973); *Lambda II*, Hendrix, R. W., ed., Cold Spring Harbor Press, Cold Spring Harbor, N.Y. (1980)); the trp, recA, heat shock, and lacZ promoters of *E. coli*; the α-amylase (Ulmanen, I., et al., *J. Bacteriol.* 162:176–182 (1985)) and the σ-28-Specific promoters of *B. subtilis* (Gilman, M. Z., et al., *Gene* 32:11–20 (1984)); the promoters of the bacteriophages of Bacillus (Gryczan, T. J., in: *The Molecular Biology of the Bacilli*, Academic Press, Inc., New York (1982)); Streptomyces promoters (Ward, J. M., et al., *Mol. Gen. Genet.* 203:468–478 (1986)); the int promoter of bacteriophage lambda; the bla promoter of the γ-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277–282 (1987)); Cenatiempo, Y. (*Biochimie* 68:505–516 (1986)); Watson, J. D., et al., in *Molecular Biology of the Gene*, Fourth Edition, Benjamin Cummins, Menlo Park, Calif. (1987)); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal4 gene promoter (Johnston, S. A., et al., *Proc. Natl. Acad. Sci. USA* 79:6971–6975 (1982); Silver, P. A., et al., *Proc. Natl. Acad.*

Sci. USA 81:5951–5955 (1984)). All of the above listed references are incorporated by reference herein.

Strong promoters are preferred. Examples of such preferred promoters are those which recognize the T3, SP6 and T7 polymerases, the $P_L$ promoter and the promoter of the mouse metallothionein I gene. A most preferred promoter for eukaryotic expression of PTP-S31 is an SV40 promoter such as that driving transcription in the pLSV vector (Livneh, E., et al., *J. Biol. Chem.* 261:12490–12497 (1986)). The sequences of such polymerase recognition sites are disclosed by Watson, J. D., et al. (in: *Molecular Biology of the Gene*, 4th ed., Benjamin/Cummings Publishing Co., Inc., Menlo Park, Calif. (1987)).

Having now generally described the invention, the same will be more readily understood through reference to the following example which is provided by way of illustration, and is not intended to be limiting of the present invention, unless specified.

6. EXAMPLE

IDENTIFICATION OF A NOVEL PTP USING THE POLYMERASE CHAIN REACTION

To identify novel PTPs in insulin-sensitive tissues, the present inventors employed the PCR technique. First strand cDNA from skeletal muscle was used as template and degenerate oligonucleotides corresponding to highly conserved regions were used as primers. A number of already characterized PTPs were identified (such as RPTPα, RPTPβ, RPTPγ, PTP 1B, T cell PTP, MEG1) using the approach described below. In addition, a novel PTP, named PTP-S31, was discovered.

Total RNA was isolated from human skeletal muscle by the guanidinium thiocyanate/CsCl procedure (Chirgwin et al., *Biochem.* 18:5293–5299 (1979)). Poly(A)$^+$ RNA was isolated on an oligo(dT) cellulose column (Aviv et al., *Proc. Natl. Acad. Sci. USA* 58:1408–1412 (1972)). First strand cDNA was synthesized from 2 µg poly(A)$^+$ RNA using oligo(dT) priming and Moloney Murine Leukemia Virus RNase H$^-$ Reverse Transcriptase from GIBCO BRL (Gaithersburg, Md. U.S.A.) in accordance with the manufacturer's recommendations.

cDNA corresponding to PTPs expressed in skeletal muscle were isolated after PCR (Saiki et al., *Science* 239:487–491 (1988)). The human skeletal muscle first strand cDNA from above (corresponding to about 50 ng) was amplified with the following set of mixed degenerative oligonucleotide primers using the Gene Amp kit (Perkin Elmer Cetus, Norwalk, Conn., U.S.A.).

Sense primer (oligonucleotide no. 58):

5' A(CT)TT(CT)TGG(ACG)(AG)(AG)ATG(AG)-
T(TCGA)TGG 3'                    [SEQ ID NO:28]

which corresponds to the PTP amino acid consensus sequence: F W X M X W

Anti-sense primer (oligonucleotide no. 57):

5' CC (TCGA)A(CT)(AGT)CC(ATC)GC(AG)C-
T(GA)CAGTG 3'                    [SEQ ID NO:29]

which corresponds to the PTP amino acid consensus sequence:

H C S A G ( S / I / V ) G/    (SEQ ID NO:41).

Each PCR cycle comprised a denaturation step at 94° C. for 1 minute, an annealing step at 37° C. for 2 minutes, and an extension step at 72° C. for 2 minutes. Thirty to 40 cycles were carried out. The reaction products were subjected to agarose gel electrophoresis. The fragments of the expected size (based on the structure of already described PTPs) were isolated, subcloned using the TA cloning system (Invitrogen, San Diego, Calif.) and sequenced by the enzymatic chain termination method described by Sanger et al., *Proc. Natl. Acad. Sci. USA* 74:5463–5467 (1977)), (Sequenase, U.S. Biochemicals) using standard techniques (Ausubel et al., eds., *Current Protocols in Molecular Biology*, John Wiley & Sons, New York, 1988).

The partial DNA sequence and the deduced amino acid sequence of a PCR fragment, termed PTP-S31, is shown in FIG. 1.

The deduced amino acid sequence of PTP-S31 is compared with PTP 1B (Chernoff et al., supra) in FIG. 2 using the GAP alignment method (Needleman et al., supra).

PTP-S31 is clearly homologous to other known PTPs, but, surprisingly, has a feature not yet described for this class of enzymes, as analyzed by the University of Wisconsin, Genetics Computer Group program. This unique feature of PTP-S31 is shown below in comparison with the consensus sequences of the previously described known PTPs (the difference is underlined):

PTP-S31: <u>R</u> C X X Y W P [SEQ ID NO:30]

Consensus: K C X X Y W P [SEQ ID NO:1]

7. EXAMPLE cDNA CLONING OF A MEMBER OF THE PTP-S31 SUBFAMILY mRNA was prepared from the rhabdomyosarcoma cell line RD (ATCC #CCL 136) as described above in Section 6. A cDNA library (library #1) was constructed using the methods described by Okayama and Berg (*Mol. Cell. Biol.* 2:161–170 (1982); *Mol. Cell. Biol.* 3:280–289 (1983)).

The pCDVI-PL vector was used for preparation of the primer fragment (Noma et al., *Nature* 319:640–646 (1986). A short synthetic adapter was used as second strand primer (Boel et al., *BioTechniques* 11:26–28 (1991)). *E. coli* DH5α (Gibco BRL, Gaithersburg, Md., U.S.A.) was used for transformation (Inuoue, H. et al., *Gene* 96:23–28 (1990)). After transformation, the cells were plated onto LB plates (containing 50 µg ampicillin/ml) at a density of 15,000–20,000 colonies per plate.

Nitrocellulose replica filters (Schleicher & Schuell, BA85) were screened with standard colony hybridization technique (Sambrook, J. et al., *Molecular Cloning: A Laboratory Manual*, 2nd Edition, Cold Spring Harbor Press, Cold Spring Harbor, N.Y. (1989)). The following oligonucleotide (#185) was synthesized, labeled at the 5' end using $T_4$ polynucleotide kinase and [γ-$^{32}$P]ATP (Amersham) and used for screening of the cDNA library:

5' CCA TCA GTA TTG GCC AGA GG 3'    [SEQ ID NO:31]

This oligonucleotide corresponds to the amino acid sequence His-Gln-Tyr-Trp-Pro-Glu [SEQ ID NO:42] of the PTP-S31 PCR fragment described in Section 6. Ten pmoles of the labeled oligonucleotide in 50 ml of hybridization solution (6×SSC, 5× Denhardt's solution, 0.05% SDS (Ausubel et al., supra) were added to replica nitrocellulose filters and allowed to hybridize at 42° C. for 3 hours. Then the filters were washed in 6×SSC, 0.05% SDS three times at room temperature, once at 42° C. and finally once at 48° C. One positive colony (clone 1.20.4) was identified by autoradiography, isolated and sequenced by standard techniques ((Sambrook et al., supra).

The nucleotide sequence of this clone, now denoted PTP-S31C [SEQ ID NO:6] and the deduced amino acid sequence [SEQ ID NO:7] are shown in FIGS. 3A–3D. This sequence includes the sequence of the PCR fragment from above and thus confirms the identity of the isolated cDNA clone. The size of this clone PTP-S31C is about 2300 bp. It contains two in-frame, putative methionine initiator codons followed by an open reading frame encoding a protein of about 39 kDa. The first ATG conforms with a consensus translation initiation sequence (Kozak, M. *Nucleic Acids Research* 15:8125–8148 (1984)). Furthermore, the distance from the 5' end of the PTP domain (N(K/R)XXXNR) [SEQ ID NO:43] to the initiator codon is similar to that of other PTPs, e.g., PTP 1B (Chernoff et al., supra) and PEP (Matthews et al., supra). However, there is no in-frame stop codon 5' of the first ATG. It is, therefore, possible that PTP-S31C is not a full-length clone.

PTP-S31C contains most of the conserved amino acid residues found in other PTPs; the amino acid sequence is about 45% identical to previously described PTPs. PTP-S31 lacks a signal peptide and a transmembrane region and might therefore belong to the class of small, intracellular PTPs. Unexpectedly, however, the deduced amino acid sequence around the catalytically essential cysteine residue differed markedly from the consensus sequence: H CSXGXGRXG [SEQ ID NO:32]. It is especially noteworthy that the arginine in position 6 C-terminal from the active site cysteine in other PTPs is replaced with phenylalanine in PTP-S31C. This arginine residue has been found to be conserved in all PTPs described, including PTPs which lack many other features common to most PTPs, for example, cdc25 (Sahdu et al., supra) and the tyrosine/serine phosphatase encoded by vaccinia virus (Guan et al., supra).

In addition, the remainder of the C terminus aligns only poorly with known PTPs. An alignment of PTP 1B (Chernoff et al., supra) and PTP-S31C is shown in FIGS. 4A–4B.

8. EXAMPLE

IDENTIFICATION OF PTP-S31D, AN ALTERNATIVE FORM OF THE NOVEL PTP

The findings disclosed in Section 7, which appeared somewhat puzzling at first to the present inventors, were subjected to a careful inspection of the sequence around the active site cysteine. This analysis revealed, in a different reading frame, a motif which is commonly seen in the C-terminal part of PTP domains: QYIFXXXXXXD [SEQ ID NO:44] (Krueger et al., *EMBO J.* 9: 241–3252 (1990)).

To analyze if this was a cloning artifact or a very unusual form of alternative splicing, two sets of PCR primers were designed (two primers on each side of the active site cysteine) as follows:
Primer set #1
  Sense primer (oligonucleotide no. 223)

5' GACGGATCCGATGCCATCAGTATTGG 3'   [SEQ ID NO:33]

Anti-sense primer (oligonucleotide no. 224)

5' TGGTCTAGATATTTACATAGTGGTT 3'   [SEQ ID NO:34]

Primer set #2

Sense primer (oligonucleotide no. 185)

5' CCATCAGTATTGGCCAGAGG 3'   [SEQ ID NO:35]

Anti-sense primer (oligonucleotide no. 225)

5' CAAGCTCAACATCACCTTCCA 3'   [SEQ ID NO:36]

PCR on PTP-S31C cDNA yielded a band of around 450 bp with primer set #1 and about 430 bp with primer set #2. If a deletion or an alternative splicing event had taken place it should be possible to detect an additional band by PCR directly on first strand cDNA from the RD cell line and/or skeletal muscle. The expected size of this band would be 430/450 bp plus the distance normally seen in PTPs between the active site cysteine and the QYIF-motif, i.e., around 130 bp.

mRNA and 1st strand cDNA was prepared from the rhabdomyosarcoma cell line RD (American Tissue Type Collection CCL 136) and human skeletal muscle as described in Section 6. About 50 ng of first strand cDNA were used with the above primers. Each PCR cycle comprised a denaturation step at 94° C. for 1 minute, an annealing step at 37° C. for 2 minutes, and an extension step at 72° C. for 2 minutes. Thirty to 40 cycles were carried out. The PCR fragments were analyzed by standard agarose gel electrophoresis (Ausubel et al., supra). Primer set #1 gave rise to two bands of the predicted sizes using cDNA from the RD cell line as template. Primer set #2 gave rise to two bands of the predicted sizes in the RD cell line as wells as in skeletal muscle cDNA.

Both bands from the RD cell line obtained with primer set #1 were cloned and sequenced. As expected, it was found that the lower band corresponds to the PTP S31C sequence. The upper band also has a sequence identical to the PTP S31C sequence but with a 133 bp insertion FIGS. 5A–5B. The upper band obtained with primer set #2 using skeletal muscle cDNA was sequenced directly using the anti-sense primer oligonucleotide no. 225. Identical sequences were found in the RD cell line and skeletal muscle. The deduced amino acid sequence of this region now shows the usual features of PTPs including the HCSXGXGR [SEQ ID NO:45] sequence and is in frame with the 5' end of PTP S31C. This novel form of PTP was designated PTP S31D. The combined sequence of PTP-S31C and PTP-S31D is shown in FIGS. 6A–6D.

FIG. 7 shows an alignment of PTP S31D with the first PTP domains of CD45 (Ralph et al., supra) and LAR (Streuli et al., supra), respectively, and with the PTP domain of PTP 1B (Chernoff et al., supra). The CLUSTAL program was used (Higgins et al., supra).

9. EXAMPLE

INSERTION OF THE S31D FRAGMENT INTO THE PTP-S31C

The following three basic steps were employed:
1. A BspHI site was introduced at the first ATG in PTP-S31C.
2. This BspHI site was used to transfer the coding region of PTP-S31C into the vector pSP72 (Promega).
3. The S31D sequence was introduced into the PTP-S31 sequence.

Step 1

To facilitate the introduction of the PTP-S31 sequence into different cloning vectors we introduced a BamHI and a BspHI site (using PCR) upstream of the first Met in the sequence of PTP-S31C:

Sense primer (oligonucleotide no. 202: BamHI/BspHI):

5' CGGGATCCATCATGAGAATGAGGCCAAT-
AAGC 3    [SEQ ID NO:37]

Anti-sense primer (oligonucleotide no. 203: XbaI):

5' GCTCTAGAGCTTGTAATCACTATATCTCCA[SEQ ID NO:38]

About 100ng of plasmid DNA from PTP-S31C (clone 1.20.4) were used as template. Each PCR cycle comprise a denaturation step at 94° C. for 1 minute, an annealing step at 50° C. for 2 minutes, and an extension step at 72° C. for 2 minutes. Ten cycles were performed. The PCR fragments were analyzed by agarose gel electrophoresis, digested with BamHI and AlwNI and a 470 bp fragment was isolated using standard techniques (Ausubel et al., supra). This fragment corresponds to the 5' end of PTP-S31C and contains the coding region of PTP-S31 starting with the first methionine.

Step 2

Using standard techniques a 940bp fragment was isolated from the original PTP-S31C clone (1.20.4) by digesting with AlwNI and EcoRV. This fragment is combined with the PCR fragment isolated in Step 1 and ligated into the pSP72 vector (Promega) which is digested with BamHI and EcoRV. The resulting plasmid is termed pSP-S31C.

Step 3

The upper band (about 580 bp including the S31D sequence) from the PCR described in Section 8 (Primer set #1) was cloned into the pBluescript KS+ vector (Stratagene, La Jolla, Calif.) using convenient restriction sites (BamHI/XbaI) which were included in the primers (oligonucleotides no. 223 and 224, respectively). The resulting plasmid was in turn digested with DraIII and NcoI giving rise to a 330 bp fragment spanning the S31D sequence which was inserted in the plasmid pSP-S31 C (Step 2) digested with the same enzymes (DraIII/NcoI). The resulting plasmid is termed pSP-S31D.

10. EXAMPLE

ANALYSIS OF PTP ENZYMATIC ACTIVITY OF PTP-S31D

10.1. CHANGE OF THE PROKARYOTIC EXPRESSION VECTOR pGEX

To accommodate a cDNA fragment from PTP S31D (see below) the cloning sites of the pGEX2T vector (Pharmacia, Uppsala, Sweden) were changed using standard techniques (*Current Protocols in Molecular Biology*, eds. F. M. Ausubel et al., John Wiley & Sons, New York, 1988). The pGEX2T vector was digested with the restriction enzymes BamHI and EcoRI and isolated. The following oligonucleotides were ligated into the digested pGEX2T vector.

5' GATCTCCGAATTCCATGGATCCAGGC-
CTCTAGAAGCTTAC 3'    [SEQ ID NO:39]

3' AGGCTTAAGGTACCTAGGTCCG-
GAGATCTTCGAATGTTAA 5'    [SEQ ID NO:40]

thereby giving rise to the vector pGEX-AK2 with the following cloning sites:

5' EcoRI, NcoI, BamHI, StuI, XbaI, HindIII 3'

10.2. INTRODUCTION OF THE PTP-S31D CODING REGION INTO pGEX-AK2

The plasmid pSP-S31D (Section 9) was digested with BamHI and EcoRV and inserted in the pcDNA I vector (Invitrogen) which was digested with the same enzymes. The resulting plasmid, pc-S31D, was in turn digested with BspHI and XbaI, giving rise to a fragment of about 1500 bp. The PTP-S31D fragment was subsequently ligated into the pGEX-AK2 (cut with NcoI and XbaI). The resulting plasmid was termed p16 (pGEX-AK2/PTP-S31D) and used in the expression studies described below. p16 encodes a fusion protein of glutathione-S-transferase and PTP-S31D (starting with the first methionine) and contains further about 500 bp of the 3' untranslated region of PTP-S31C (and PTP-S31D).

An identical strategy was used to introduce the PTP-S31C into pGEX-AK2, except that pSP-S31C was used to produce the pcDNA I based plasmid: pc-S31C. The resulting plasmid was termed p17 (pGEX-AK2/PTP-S31C).

10.3. EXPRESSION OF GST-PTP S31 FUSION PROTEIN IN *E. COLI*

The pGEX-AK2/PTP-S31D vector construct, p16, and the pGEX-AK2/PTP-S31C vector construct, p17, which encode fusion proteins of glutathione S-transferase (GST) and PTP-S31D or PTP-S31C, respectively (Smith et al., *Proc. Natl. Acad. Sci. USA* 83:87-3-8707 (1988)) were introduced into the *E. coli*, strain DH5α (Cat. No. 8263SA, Bethesda Research Laboratories, Gaithersburg, Md.) and SURE™ (Cat. No. 200294, Stratagene, La Jolla, Calif. 92037).

Overnight cultures of the transformed *E. coli* were grown in LB medium and diluted 1:10 in fresh medium (45 ml overnight culture plus 405 ml LB medium with ampicillin) and grown for 1 hour at 37° C. Isopropyl-1-thio-β-D-galactopyranoside (IPTG) was added to a final concentration of 0.2 mM (DH5α) and 5 mM (SURE) and the cultures were incubated for a further 4 hours. A volume of 400 ml from each culture was centrifuged at 4° C. for 10 minutes at 5000 rpm in a Sorvall GS3 rotor. The pellets were frozen in liquid nitrogen, then thawed in 3 ml of lysis buffer (0.03M Tris HCl, pH 8.0, 2.5 mM EDTA, 10 µg/ml aprotinin, 1 mM phenylmethylsulfonyl fluoride (PMSF), 1% (v/v) 2-mercaptoethanol) and sonicated on ice (M.S.E. Ultrasonic Disintegrator—100 W Model (cat. no. 7100): 3 cycles of 30 seconds, maximum setting). After sonication, the lysates were centrifuged and the supernatant filtered through a 0.45 µm filter (Millipore). Controls were: (1) pGEX-AK2 with and without IPTG; and (2) p16 and p17 without addition of IPTG. The GST-PTP-S31D and GST-PTP-S31C fusion proteins as well as GST were isolated as soluble proteins by glutathione-Sepharose 4B affinity chromatography (Cat. No. 17-0756-01, Pharmacia, Uppsala, Sweden) according to the manufacturer's instructions using 150 µl glutathione-Sepharose 4B per milliliter of the sonicated and sterile-filtered bacterial lysates and incubating with slow rotation for 1 hour at 4° C. The Sepharose beads were washed 3 times in phosphate buffered saline (PBS) and finally resuspended in 250 µl lysis buffer (see above). Expression of the GST/PTP-S31D and GST/PTP-S31C fusion proteins, respectively, as well as the glutathione-S-transferase was verified by sodium dodecylsulfate (SDS) polyacrylamide gel electrophoresis (PAGE) using standard techniques (Ausubel et al., supra). Various amounts of the suspension of glutathione-Sepharose beads with GST-PTP-S31D, GST-PTP-S31C, and GST (control) were analyzed for enzymatic activity as described below.

10.4. ANALYSIS OF ENZYMATIC ACTIVITY OF THE GST-PTP-S31D FUSION PROTEIN

The activity of PTP-S31D towards the substrate p-nitrophenyl phosphate (pNP-P) was measured essentially as described by Tonks et al., *J. Biol. Chem.* 263:6731–6737 (1988)). Increasing amounts of the glutathione-Sepharose beads with GST/PTP-S31D, GST/PTP-S31C and GST, respectively, from above were incubated with 25 mM pNP-P at room temperature in a reaction mixture containing 50 mM 2-(N-morpholino)ethane sulfonic acid (MES) pH 5.5, 10 mM dithiothreitol, and 5 mM ethylenediamine tetraacetic acid (EDTA). The reaction was stopped by addition of equal volumes of 0.4M NaOH. After centrifugation, the supernatants were transferred to microtiter plates and the absorbance at 405 nm was read with a Dynatech MR5000 reader.

In this phosphatase assay only the GST/PTP-S31D fusion protein showed activity (FIG. 8).

11. EXAMPLE

NORTHERN BLOT ANALYSIS OF PTP-S31

Total RNA was isolated from several human tissues (spleen, placenta, lung, kidney, colon, liver and from two sources of normal skeletal muscle as well as diabetic skeletal muscle) and cell lines (KG1 (ATCC CCL 246); MOLT-4 (ATCC CRL 1582); Raji (ATCC CCL86); K-562 (ATCC CCL 243); MEG01; Hep G2 (HB 8065); Ea.hy (obtained from Dr. Cora-Jean S. Edgell, University of North Carolina, Chapel Hill, N.C.); A673 (ATCC CRL 1598); and RD (ATCC CCL 136)) by the acid guanidium thiocyanate-phenol-chloroform extraction procedure as described by Puissant et al., *BioTechniques* 8:148–149 (1990)).

Poly(A)$^+$ RNA was isolated on an oligo(dT) column (Aviv et al., *Proc. Natl. Acad. Sci. USA* 69:1408–1412 (1972)). Two µg poly(A)$^+$ RNA were loaded in the lanes, separated in an agarose-formaldehyde gel and blotted onto nylon filters (Stratagene, La Jolla) using standard techniques (Ausubel et al., supra). The filters were hybridized with the PTP-S31 PCR fragment (described in Section 6) labeled with [α $^{32}$P]dATP. The $^{32}$P-labeling was done with the Random Primers DNA Labeling System (Cat. no. 8187SA, Bethesda Research Laboratories, Gaithersburg, Md. 20877, U.S.A.) according to the manufacturer's instructions. Subsequently, the filters were washed under stringent conditions and applied to X-ray films.

Analysis of the Northern blots showed a broad range of transcripts of PTP-S31 (from about 2.1 to 2.8 kb) in one of the sources of skeletal muscle poly(A)$^+$ RNA, whereas the expression was barely detectable in the other sample of normal skeletal muscle. The broad band in this Northern blot might indicate the existence of several forms of mRNA (e.g., alternative splicing) derived from the same gene. Expression of PTP-S31 was also demonstrated in skeletal muscle of a patient with type II diabetes.

Surprisingly, the size of the major transcript in the RD cell line is about 4.4 kb. Additionally, a relatively broad but weaker band (2.1–2.4 kb), as well as a weak band of around 6 kb, are found in the RD cell line. A long exposure of the Northern blot with skeletal muscle RNA shows that there is a minor transcript of about 4.4 kb, as in the RD cell line. In lung tissue, a weak signal is found at about 8 kb. Using Northern blotting, none of the other tissues or cell lines showed measurable expression levels of PTP-S31. However, with the sensitive PCR technique, PTP-S31 was found to be expressed in the following tissues and cell lines: liver (pregnancy); placenta; skeletal muscle; kidney; peripheral blood lymphocytes; HepG2 cells (ATCC CCL 86) (almost exclusively in the PTP S31C form), RD cells (ATCC CCL 136); A673 cells (ATCC CRL 1598); IM9 cells (ATCC CCL 159); CEM cells (ATCC CCL 119); U937 cells (ATCC CRL 1593); A549 cells (ATCC CCL 185); and KLE cells (ATCC CRL 1622).

12. EXAMPLE

CLONING OF ADDITIONAL SUBTYPES OF PTP-S31

Due to the observed size difference between the major transcripts of PTP-S31 in the RD cell line and skeletal muscle, further experiments were conducted involving cDNA cloning of PTP-S31 from the two sources of normal skeletal muscle showing low and high expression levels, respectively (based on the Northern blot analysis described in Section 11).

Poly (A)$^+$ RNA was isolated from the two sources of normal human skeletal muscle as described in Section 11, above. Using 5 µg of these poly (A)$^+$ RNA preparations, two λ ZAP II cDNA libraries were prepared according to the manufacturer's instructions (Stratagene, La Jolla, Calif.). The library constructed from the RNA with low expression levels of PTP-S31 was termed library #2. The library constructed from RNA with high expression levels of PTP-S31 was termed library #3. A total of 2×10$^6$ plaques were screened from each library using standard filter hybridization techniques (Ausubel et al., supra). Duplicate Hybond N+ (Amersham) filters were hybridized with the same $^{32}$P-labeled PCR fragment as that used in Section 11, above.

The $^{32}$P-labeling was done with the Random Primers DNA Labeling System (Cat. no. 8187SA, Bethesda Research Laboratories, Gaithersburg, Md. 20877, U.S.A.) according to the manufacturer's instructions. The filters were washed at high stringency (0.1×SSC, 0.05% SDS). Subsequently, the filters were applied to X-ray films.

Three positive clones were identified from library #2, isolated, subjected to in vivo excision according to the manufacturer's instructions and analyzed by sequencing. From library #3 a total of nine positive clones were isolated and analyzed.

Figure 10:
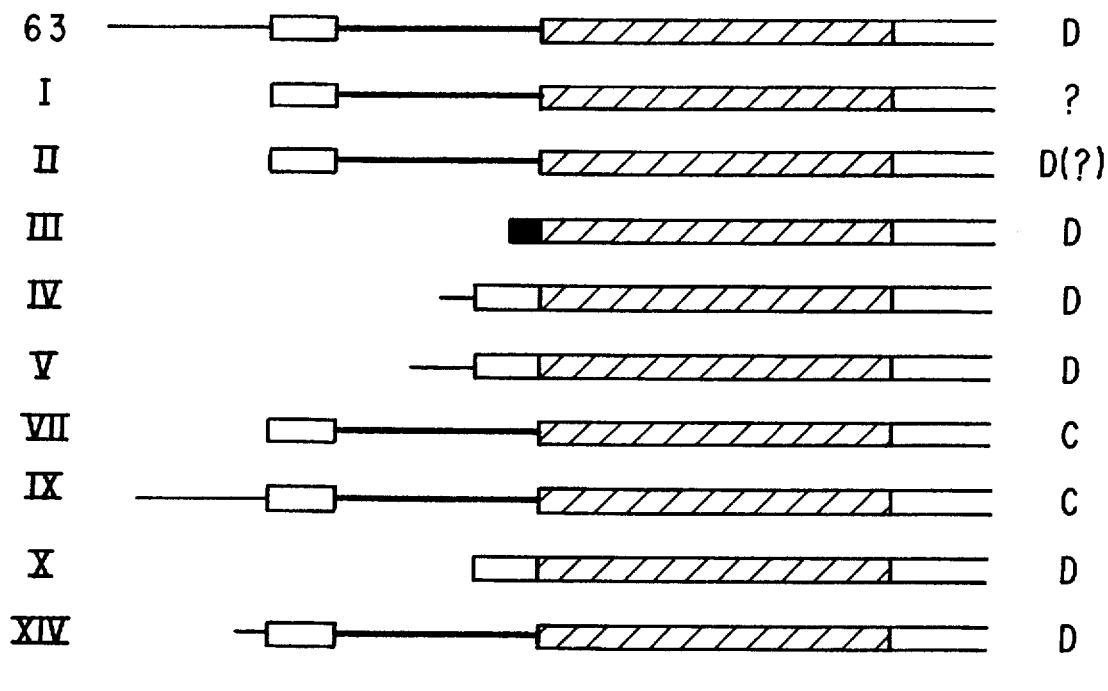

The longest clone (S31D-63) was isolated from cDNA library #2; its nucleotide sequence and predicted amino acid sequence is shown in FIGS. 9A–9E. Surprisingly, neither this clone nor any of the other clones analyzed contained the 5' end of the PTP-S31C clone (clone 1.20.4) isolated from the RD cDNA library (library #1). Instead, all clones from the skeletal muscle cDNA libraries contained 5' ends which are not similar to any known sequence. None of the clones appeared to be full-length since there was no in-frame ATG triplet upstream from the nucleotide where these clones differ from clone 1.20.4. The various forms identified are schematically shown in FIG. 10.

Isolation of additional, partial clones from library #3 showed further variants of PTP-S31 which most likely resulted from alternative splicing. The deduced amino acid sequences of these variants are shown in FIG. 11.

A new cDNA library (library #14) was constructed from poly(A)$^+$ RNA from the RD cell line using the λ ZAP II cDNA cloning procedure (Stratagene, La, Jolla, Calif.) as described above. A total of 1×10$^6$ plaques were screened using standard filter hybridization techniques (Ausubel et al., supra). Duplicate Hybond N (Amersham) filters were hybridized with the same $^{32}$P-labeled PCR fragment as that used in Section 11, above. The 32P labeling was done with the Random Primers DNA Labeling System (Cat. No. 8187SA, Bethesda Research Laboratories, Gaithersburg, Md.) according to the manufacturer's instructions. The filters were washed at high stringency (0.1×SSC, 0.05% SDS) and subsequently applied to X-ray films. From library #14, a total of 7 positive clones were isolated, subjected to in vivo excision according to manufacturer's instructions and analyzed.

Two of the clones from library #14 are identical to clone 1.20.4, except that they are a few bases shorter at the 5' end (i.e., both are PTP-S31C). Five clones were found to be similar to clone S31D-63 from above, but they differed at the 5' ends. The longest two of these clones were characterized by sequencing. Clone S31-RD#2 corresponds to the D form of PTP S31, whereas clone S31-RD#6, which is about 250 base pairs shorter than clone S31-RD#2 at the 5' end, corresponds to the C form. Otherwise both clones are identical. Partial nucleotide (SEQ ID NO:21) and predicted amino acid sequences (SEQ ID NO:22) of PTP-S31 RD#2 are shown in FIGS. 12A–12D. Surprisingly, this form of PTP-S31 contained a transmembrane domain. Therefore, PTP-S31 may exist both as an intracellular and as a receptor-type PTP.

It is noteworthy that, until now, only one mammalian transmembrane PTP, RPTPβ, has been found to contain a single PTPase domain (Krueger et al., supra). Like RPTPβ, PTPS31-RD#2 has only. one PTPase domain.

Furthermore, the amino acid sequence of PTPS31-RD#2 adjacent to the putative transmembrane region shares similarity with the interleukin 2 receptor β chain and other cytokine receptors (Miyajama et al., Annu. Rev. Immunol. 10:295–3331 (1992). This region also shares some homology with fibronectin type III (FN-III) domains (Patthy, L., Cell 61:13–14 (1990)).

Some of the structural features common to fibronectin type III-like domains can be seen in the extracellular domain of PTPS31-RD#2. In the amino acid sequence (SEQ ID NO:22) presented in FIG. 12a; a total of four FN-III like domains can be identified (see FIG. 14). The domains are designated S31-FN-1 (the most C-terminal and therefore adjacent to the transmembrane region) to S31-FN-4 (the most N-terminal). These FN-III-like domains contain a relatively high number of cysteine residues. This is in contrast to the FN-III-like domains of LAR (Streuli et al., supra) and cytokine receptors (Patthy, supra). Also, an otherwise highly conserved tryptophan residue is replaced in S31-FN-2 with a phenylalanine residue. Further, the demarcations between individual FN-III domains are not nearly as well-conserved as in RPTPβ.

There are several potential sites for N-linked glycosylation in the extracellular domain of PTP-S31.

Surprisingly, a stretch of about 100 amino acids or PTPS31-RD#2 shows a relatively high sequence similarity to a portion of the α subunit of the insulin receptor (FIG. 15). The similarity of PTPS31-RD#2 to the insulin receptor as well as to cytokine receptors indicates that the transmembrane form of PTP-S31 may be regulated by hormones or cytokines. Alternatively, the FN-III-like domains may indicate that PTP-S31 is involved in cell-cell interactions.

13. EXAMPLE

DETECTION AND MEASUREMENT OF PTP-S31 PROTEIN IN A CELL

13.1. PRODUCTION OF ANTIBODIES WITH SPECIFICITY FOR PTP-S31D

Antiserum with specificity for PTP-S31D was produced by standard techniques (Hudson, L. et al., Practical Immunology, 3rd Edition, Blackwell, Oxford, 1989). In brief, 200 µg the GST-PTP S31D fusion protein (see Section 10) in 200 µl phosphate buffered saline were combined with an equal volume of Freund's complete adjuvant (Sigma, Cat. No. F5881) and injected intracutaneously into two New Zealand rabbits. Each rabbit received 100 µg of the fusion protein. Two weeks after the first injection, booster injections without Freund's adjuvant were administered. After 2 more weeks, 20 ml of blood were obtained from each rabbit and allowed to clot at room temperature for 1 hour in glass tubes. The clots were centrifuged after loosening from the tube, and aliquots of the serum were transferred to fresh tubes and stored at −20° C. until use.

To remove the antibodies which are specific for glutathione S-transferase (GST), the serum was passed over a glutathione-Sepharose 4B column which has been saturated with glutathione S-transferase using the procedure described in Section 10. The pGEX-AK2 construct was used to produce the GST protein. The serum was passed over the column three times to ensure complete removal of the anti-GST antibodies. The efficiency of the removal was assessed by Western blotting as described below.

13.2. DETECTION AND MEASUREMENT OF PTP-S31D IN A CELL LINE

The anti-PTP-S31D antibody can be used to detect the expression of PTP-S31 in mammalian cells. Standard immunofluorescence techniques provide information about expression of this protein in specific cell lines and tissues. Even more importantly, this antibody preparation can be used to determine the quantity of the protein in cell lines and tissues. As an example of the latter application of the anti-PTP S31 antibody, the detection of PTP-S31 in the RD cell line (ATCC CCL 136) is described below. It should be emphasized that this Example is not in any way intended to be limiting as to the use of the antibody, which can be used for detection of PTP-S31 in other cells and tissues as well. Likewise, the antibody preparation can be useful in purification of naturally occurring or recombinant PTP S31 and for establishing other types of detection assays.

Using standard techniques, the RD cell line is cultured in Eagle's minimal essential medium (Cat. No. 041-022570, GIBCO Life Technologies Ltd., Paisley, Scotland) with twice the normal concentrations of amino acids and vitamins with Hanks' balanced salt solution and 10% fetal calf serum (FCS) (GIBCO-BRL).

The cells are washed twice in phosphate buffered saline (PBS) and the supernatant removed. The cells from one tissue culture plate (10 cm diameter) are lysed in 800 µl of a Triton X-100 lysis buffer (20 mM HEPES pH 7.5, 50 mM NaCl, 10% glycerol, 1.0% Triton X-100, 1.5 mM MgCl$_2$, 4 mM ethylene glycol-bis(β-aminoethylethyl ether)N,N,N', N'-tetraacetate (EGTA; Sigma ED2SS), 10 µg/ml aprotinin, 1 mM phenylmethylsulfonyl fluoride (PMSF)). The lysate is centrifuged and the supernatant transferred to fresh tubes in aliquots for storage at −80° C. until use.

For testing, 1–50 μl of this lysate is mixed with 25 μl SDS sample buffer (62.5 mM Tris HCl, pH 7.0, 3.0% (v/v) SDS, 10% (v/v) glycerol, 10% 2-mercaptoethanol, and 0.05% (w/v) bromophenol blue), boiled for 5 minutes, separated by 7.5% SDS-polyacrylamide gel electrophoresis and blotted onto nitrocellulose using standard techniques (Burnette, W. N., *Anal. Biochem.* 112:195–201 (1981)).

A standard curve for the quantitative determination of PTP-S31D is generated by using defined amounts of purified *E. coli*-produced GST-PTP-S31D fusion protein from above in parallel with the RD cell lysates.

The nitrocellulose filters are incubated for 30 minutes with 2 grams milk powder (Carnation, Non-Fat Dry Milk, Carnation, Los Angeles, Calif.) per liter PBS to block nonspecific binding, washed once in PBS containing 0.02% (v/v) Tween-20 (Sigma, P1379) (PBS-Tween) and 0.2% (w/v) gelatin (BioRad Cat. No. 170-6537, Richmond, Calif.), washed 3 times in PBS-Tween and finally incubated for 4 hr with a 1:200 dilution (in PBS-Tween) of the anti-PTP-S31D antiserum preparation described above. After three washings in PBS-Tween, the filters are incubated with horseradish peroxidase-conjugated goat antirabbit IgG (Cat. No. 170-6525, BioRad). The filters are washed three times in PBS-Tween and the amount of rabbit antibody bound, which indicates the amount of PTP-S31D, is determined by the enhanced chemiluminescence (ECL) technique according to the manufacturer's instructions (Cat. No. RPN 2106, Amersham, UK). Comparison of the signals obtained from the RD cell line with the standard curve obtained with the *E. coli*-produced GST-PTP S31D fusion protein allows determination of the amount of PTP-S31D produced by the RD cell line.

14. EXAMPLE

IDENTIFICATION OF AN AGENT THAT STIMULATES OR INHIBITS ENZYMATIC ACTIVITY OF PTP-S31

Two different sources of PTP-S31 protein are used for the evaluation of potential modulators of the enzymatic activity:

1. The GST-PTP-S31D (and C) fusion proteins as described in Section 10;
2. PTP-S31 transiently expressed in 293 cells as described below.

The cDNA containing the entire coding region of PTP-S31 (C or D) or a functional portion thereof, is inserted into the mammalian expression vector pcDNA I (Cat. No. V490-20, Invitrogen, San Diego) using standard techniques (Ausubel et al., supra). The 293 cell transient expression system described by Gorman et al., *Virology* 171:377–385 (1989) is used to produce enzymatically active PTP-S31D. Using standard techniques, the 293 cells are cultured in Dulbecco's Modified Eagle Medium (Cat. No. a041-02430, GIBCO, Life Technologies Ltd., Paisley, Scotland) supplemented with 10% FCS in an atmosphere of 5% $CO_2$ at 37° C.

Ten μg of the plasmid construct PTP-S31D/pcDNA I (or PTP-S31C/pcDNA I) are mixed with 0.5 ml 0.25M $CaCl_2$ and 0.5 ml 2xBBS (50 mM N,N-bis(2-hydroxyethyl)-2-aminoethane-sulfonic acid (BES), 280 mM NaCl, 1.5 mM $Na_2HPO_4$) and used for transfection of $1.5 \times 10^6$ 293 cells in a 10 cm Petri dish as described by Chen et al., *Mol. Cell. Biol.* 7:2745–2752 (1987). The cells are incubated 24 hr at 37° C. under 3% $CO_2$ after the addition of the Ca-phosphate-DNA precipitate, then washed once in DMEM supplemented with 10% FCS and incubated in fresh medium for additional 24 hours at 37° C. under 5% $CO_2$. The medium is removed and the cells lysed in 1.0 ml of lysis buffer (20 mM HEPES, pH 7.5, 150 mM NaCl, 10% glycerol, 1.0% Triton X-100, 1.5 mM $MgCl_2$, 4 mM EGTA, 10 μg/ml aprotinin, 1 mM PMSF). The cell lysates are centrifuged at 2500×g for 2 minutes at 4° C. The supernatant is removed and 100 μl aliquots are quick-frozen in liquid nitrogen and stored at −70° C. until use.

The PTP-S31 in the lysate may be partially purified using conventional chromatographic techniques such as anion exchange chromatography and gel filtrations.

Three different substrates are used for the evaluation of potential modulators of the PTP-S31 phosphatase activity:

(1) p-nitrophenyl phosphate (pNP-P; Sigma 104-0);

(2) $^{32}$P-labeled Raytide (Oncogene Science Inc., Manhasset, N.Y.);

(3) $^{32}$P-labeled bovine myelin basic protein (MBP). Substances which either decrease or increase the activity of PTP-S31 against one or more of these substrates are analyzed further.

14.1. LABELING OF RAYTIDE AND MYELIN BASIC PROTEIN WITH $^{32}$P

The activity towards $^{32}$P-labeled Raytide™ of the GST/PTP-S31D (and C) fusion proteins (Section 10) as well as of the complete and preferably, functional part thereof expressed in 293 cells, is measured essentially as described by Krueger et al. (*EMBO J.* 9:3241–3252 (1990)). The synthetic peptide Raytide is labeled with $^{32}$P using the tyrosine kinase $p60^{c-src}$ according to the manufacturer's instructions (Oncogene Science) with minor modifications. In brief, 2 μl of $p60^{c-src}$ are mixed with 20 μl Raytide (1 mg/ml) and 108 μl of kinase buffer (50 mM HEPES, pH 7.5 containing 10 mM $MgCl_2$, 0.2% (v/v) β-mercaptoethanol, 30 μM ATP and 50 μCi [γ-$^{32}$P]ATP). The mixture is incubated at 37° C. for 16 hours, and the reaction is stopped by addition of 500 μl of 20% (w/v) trichloroacetic acid (TCA) in 20 mM $NaH_2PO_4$ and 100 μl of 5 mg/ml of acetylated bovine serum albumin. The mixture is centrifuged, the precipitate is washed three times in 20% TCA/20 mM $NaH_2PO_4$ and is finally redissolved in 0.2M Tris-HCl pH 8.0.

Myelin basic protein (Sigma) is labeled using a procedure similar to that used for Raytide (Guan et al., *Nature* 350:359–362 (1991)). Thirty μg of MBP is labeled in a 60 μl reaction volume containing the following components: 50 mM HEPES buffer, pH 7.5, 10 mM $MgCl_2$, 0.067% β-mercaptoethanol, 0.05 mM ATP including 150 μCi [γ-$^{32}$P]ATP and 4 Units $p43^{v-abl}$ kinase (Oncogene Science). The mixture is incubated for 60 minutes at 30° C., and the reaction is stopped by addition of ice-cold TCA to a final concentration of 20%. After 30 minutes on ice, the precipitate is washed three times in 20% TCA and redissolved in 100 μl $H_2O$.

14.2. ASSESSMENT OF PTP ACTIVITY USING THE SUBSTRATE pNP-P

The activity of the GST/PTP-S31D fusion protein towards pNP-P is measured as described in Section 10, above. The substances to be analyzed for their ability to stimulate or inhibit phosphatase activity are added to the GST/PTP-S31D fusion protein 5 minutes prior to the addition of pNP-P. A similar procedure is used for PTP-S31D expressed in 293 cells, where the PTP-S31D/293 cell lysate is used directly.

Table I, below, shows the effect of several agents on PTP activity of the GST/PTP-S31 fusion protein bound to glutathione-Sepharose beads as described in Section 10. The indicated concentrations of the agents are the final concentrations in the reaction mixture after addition of the substrate, pNP-P. The phosphatase assay mixture contained 50 mM 2-(N-Morpholino)ethane sulfonic acid (MES) pH 5.5, 10 mM dithiothreitol, 25 mM pNP-P and 2 µl of the GST/PTP-S31-Sepharose suspension. When testing orthovanadate, poly(Glu/Tyr)4:1 and poly-L-lysine, 5 mM EDTA was included in the assay mixture. The reaction was carried out at room temperature and stopped after 30 minutes by addition of equal volumes of 0.4M NaOH. After centrifugation, the supernatants were transferred to microtiter plates and the absorbance at 405 nm read with a Dynatech MR5000 plate reader. For comparison, Table I includes published data of the activity of PTPβ and LAR using Raytide as a substrate (Itoh et al (*J. Biol. Chem.* 267: 12356–2363 (1992)).

TABLE I

EFFECTS OF VARIOUS AGENTS ON PTP ACTIVITY

| Agent | Conc | PTP Activity (% of control) | | |
|---|---|---|---|---|
| | | S31D | PTPβ | LAR |
| | (mM) | | | |
| MgCl$_2$ | 1 | 123 | 90 | 119 |
| | 10 | 140 | 141 | 56 |
| MnCl$_2$ | 1 | 110 | 85 | 72 |
| | 10 | 140 | 64 | 30 |
| ZnCl$_2$ | 0.1 | 68 | 18 | 90 |
| | 1 | 13 | 3 | 120 |
| | 10 | 9 | 0 | 6 |
| Ortho-vanadate | 0.1 | 64 | 33 | 59 |
| | 1 | 23 | 6 | 25 |
| | (µg/ml) | | | |
| Poly (Glu/Tyr) | 1 | 84 | 97 | 103 |
| | 10 | 85 | 85 | 97 |
| | 100 | 77 | 61 | 96 |
| Poly-L-Lysine | 1 | 156 | 239 | 123 |
| | 10 | 172 | 653 | 230 |
| | 100 | 192 | 125 | 247 |

It should be emphasized that the above Example is not intended in any way limit the scope of the invention.

14.3. ASSESSMENT OF PTP ACTIVITY USING THE SUBSTRATES RAYTIDE OR MBP

Five µl 10× PTP buffer (250 mM HEPES, pH 7.3, 50 mM EDTA, 100 mM dithiothreitol) are mixed with (a) 5 µl $^{32}$P-labeled Raytide or MBP (corresponding to 10–20×10$^4$ cpm), b) 5, 10 and 25 µl, respectively, of the PTP-S31D/293 cell lysate, or 0.5, 1 and 5 µl of the suspension of the GST-PTPS31D fusion protein bound to glutathione-Sepharose beads (see Section 10) and (c) H$_2$O to a final volume of 50 µl. The reaction is stopped after 30 minutes at 37° C. When using Raytide, the reaction is stopped by addition of 0.75 ml acidic charcoal mixture (Krueger et al., *EMBO J.* 9:3241–3252 (1990)): 0.9M HCl, 90 mM sodium pyrophosphate, 2 mM NaH$_2$PO$_4$, 4% (v/v) Norit A (Sigma)). After mixing and centrifugation, 400 µl of the supernatant are removed and the amount of radioactivity measured. When using MBP, the reaction is stopped with 20% TCA (final volume). The amount of $^{32}$P in the supernatant is then measured.

The substances to be analyzed for modulatory activities are added to the PTP-S31/293 cell lysate 5 minutes prior to initiation of the assays.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

---

What is claimed is:

1. A method for detecting the presence of a nucleic acid molecule encoding a normal or mutant PTP-S31 protein in a sample containing nucleic acid molecules, comprising:

(a) contacting the sample, with a nucleic acid probe encoding amino acid sequence SEQ ID No: 7, 15, 16, 17, 18, 20 or 22 under hybridizing conditions; and (b) measuring the hybridization of the probe to nucleic acid molecules in the sample, thereby detecting the presence of the nucleic acid molecule encoding said normal or mutant PTP-S31 Protein.

2. The method of claim 1, additionally comprising before step (a):

(c) selectively amplifying the amount of the nucleic acid molecule encoding said normal or mutant PTP-S31 protein.

3. An isolated nucleic acid molecule having a nucleotide sequence that (a) encodes the amino acid sequence SEQ ID No: 7, or (b) is the complement of the nucleotide sequence of (a).

4. The nucleic acid molecule of claim 3 having the nucleotide sequence SEQ ID No: 6.

5. An isolated nucleic acid molecule having a nucleotide sequence that (a) encodes the amino acid sequence from residue 85 to residue 402 of SEQ ID No: 15, (b) is the complement of the nucleotide sequence of (a).

6. The nucleic acid molecule of claim 5 having the nucleotide sequence SEQ ID No: 14.

7. The nucleic acid molecule of claim 5 having a nucleotide sequence which encodes additionally at the amino terminus an amino acid sequence selected from the group consisting of a) residue 1 to 44 of SEQ ID No: 16; b) residue 1 to 52 of SEQ ID No: 17; c) residue 1 to 67 of SEQ ID No: 18; d) residue 1 to 84 of SEQ ID No: 15; e) residue 1 to 73 of SEQ ID No: 20; and f) residue 1 to 4 of SEQ ID No: 11.

8. An isolated nucleic acid molecule having a nucleotide sequence that (a) encodes the amino acid sequence SEQ ID No: 22, or (b) is the complement of the nucleotide sequence of (a).

9. The nucleic acid molecule of claim 8 having the nucleotide sequence SEQ ID No: 21.

10. A recombinant vector comprising the nucleotide sequence of the nucleic acid molecule of claims 3, 5, or 8.

11. The recombinant vector of claim 10 wherein the nucleotide sequence is operatively linked with an element that controls expression of the nucleotide sequence in a host cell.

12. A host cell transformed or transfected with the nucleic acid molecule of claims 3, 5, or 8.

13. A host cell transformed or transfected with the recombinant vector of claim 10.

14. A host cell transformed or transfected with the recombinant vector of claim 11.

15. A method for preparing PTP-S31 proteins or fragments thereof comprising:

(a) culturing the host cell of claim 14 so that the protein is expressed by the host cell; and (b) recovering the protein from the culture.

* * * * *